United States Patent
Wiyatno et al.

(10) Patent No.: US 10,450,604 B2
(45) Date of Patent: Oct. 22, 2019

(54) DEVICE AND METHOD FOR MAKING DISCRETE VOLUMES OF A FIRST FLUID IN CONTACT WITH A SECOND FLUID, WHICH ARE IMMISCIBLE WITH EACH OTHER

(71) Applicant: APPLIED BIOSYSTEMS, LLC, Carlsbad, CA (US)

(72) Inventors: Willy Wiyatno, Union City, CA (US); Linda Lee, Palo Alto, CA (US); David Cox, Foster City, CA (US); James Nurse, Westport, WA (US); Douglas Greiner, Fremont, CA (US); Dennis Lehto, Santa Clara, CA (US); Janusz Wojtowicz, Sunnyvale, CA (US); Sam Woo, Redwood City, CA (US); Richard Reel, Hayward, CA (US)

(73) Assignee: Applied Biosystems, LLC, Foster City, CA (US)

( * ) Notice: Subject to any disclaimer, the term of this patent is extended or adjusted under 35 U.S.C. 154(b) by 194 days.

(21) Appl. No.: 14/844,279

(22) Filed: Sep. 3, 2015

(65) Prior Publication Data
US 2016/0097087 A1    Apr. 7, 2016

Related U.S. Application Data

(60) Continuation of application No. 13/724,079, filed on Dec. 21, 2012, now Pat. No. 9,140,630, which is a
(Continued)

(51) Int. Cl.
*C12Q 1/68*    (2018.01)
*C12Q 1/6869*    (2018.01)
(Continued)

(52) U.S. Cl.
CPC ...... *C12Q 1/6869* (2013.01); *B01L 3/502715* (2013.01); *B01L 3/502784* (2013.01);
(Continued)

(58) Field of Classification Search
CPC ......... B01L 3/50278; B01L 2200/0673; B01L 2200/0605; B01L 2300/0861; B01L 2300/0864; B01L 2300/0867; G01N 35/08
See application file for complete search history.

(56) References Cited

U.S. PATENT DOCUMENTS 3,960,020 A    6/1976 Gordon et al.
4,253,846 A    3/1981 Smythe et al.
(Continued)

FOREIGN PATENT DOCUMENTS

WO    20040002627    1/2004

OTHER PUBLICATIONS

"Microchip Device for Cell Lysis, Multiplex PCR Amplification, and Electrophoretic Sizing," Analytical Chemistry, 1998, 158-162, Waters, L. C.., et al., USA.
(Continued)

*Primary Examiner* — Brian R Gordon
(74) *Attorney, Agent, or Firm* — Jones Robb, PLLC

(57) ABSTRACT

A method for generating, within a conduit, discrete volumes of one or more fluids that are immiscible with a second fluid. The discrete volumes can be used for biochemical or molecular biology procedures involving small volumes, for example, microliter-sized volumes, nanoliter-sized volumes, or smaller. The discrete volumes are separated from one another by a liquid that is immiscible with the fluid(s) of the discrete volumes, for example, aqueous immiscible-fluid-discrete volumes separated by an oil.

6 Claims, 46 Drawing Sheets

Related U.S. Application Data continuation of application No. 13/069,213, filed on Mar. 22, 2011, now Pat. No. 8,361,807, which is a division of application No. 11/508,044, filed on Aug. 22, 2006, now Pat. No. 7,955,864.

(60) Provisional application No. 60/818,197, filed on Jun. 30, 2006, provisional application No. 60/731,133, filed on Oct. 28, 2005, provisional application No. 60/710,167, filed on Aug. 22, 2005.

(51) Int. Cl.
| | | |
|---|---|---|
| B01L 3/00 | (2006.01) | |
| F15C 5/00 | (2006.01) | |
| F16K 99/00 | (2006.01) | |
| G01N 35/08 | (2006.01) | |
| G01N 1/14 | (2006.01) | |
| C12Q 1/6806 | (2018.01) | |
| C12Q 1/6874 | (2018.01) | |
| G01N 27/447 | (2006.01) | |
| B01L 3/02 | (2006.01) | |
| B01L 7/00 | (2006.01) | |

(52) U.S. Cl.
CPC ......... *C12Q 1/6806* (2013.01); *C12Q 1/6874* (2013.01); *F15C 5/00* (2013.01); *F16K 99/0001* (2013.01); *F16K 99/0011* (2013.01); *F16K 99/0013* (2013.01); *G01N 1/14* (2013.01); *G01N 27/44743* (2013.01); *G01N 27/44769* (2013.01); *G01N 35/08* (2013.01); *B01J 2219/0036* (2013.01); *B01J 2219/0061* (2013.01); *B01J 2219/00353* (2013.01); *B01J 2219/00364* (2013.01); *B01J 2219/00608* (2013.01); *B01J 2219/00612* (2013.01); *B01J 2219/00619* (2013.01); *B01J 2219/00626* (2013.01); *B01J 2219/00637* (2013.01); *B01J 2219/00653* (2013.01); *B01J 2219/00657* (2013.01); *B01J 2219/00659* (2013.01); *B01L 3/0293* (2013.01); *B01L 7/52* (2013.01); *B01L 2200/0673* (2013.01); *B01L 2200/10* (2013.01); *B01L 2300/0864* (2013.01); *B01L 2300/0867* (2013.01); *B01L 2400/0421* (2013.01); *B01L 2400/0487* (2013.01); *C12Q 2535/101* (2013.01); *F16K 2099/0084* (2013.01); *Y10T 137/0318* (2015.04); *Y10T 137/4259* (2015.04); *Y10T 137/85978* (2015.04); *Y10T 137/85986* (2015.04); *Y10T 137/86863* (2015.04); *Y10T 436/2575* (2015.01)

(56) References Cited

U.S. PATENT DOCUMENTS

| | | |
|---|---|---|
| 4,271,123 A | 6/1981 | Curry et al. |
| 4,528,158 A | 7/1985 | Gilles et al. |
| 4,574,850 A | 3/1986 | Davis et al. |
| 4,610,170 A | 9/1986 | Ekholm et al. |
| 4,908,112 A | 3/1990 | Pace |
| 5,092,972 A | 3/1992 | Ghowsi |
| 5,484,107 A | 1/1996 | Holmes |
| 5,843,767 A | 12/1998 | Beattie et al. |
| 5,961,800 A | 10/1999 | McBride et al. |
| 6,258,324 B1 | 7/2001 | Yiu |
| 6,348,354 B1 * | 2/2002 | Adolfsen ............... G01N 35/08 422/105 |
| 6,432,814 B1 | 8/2002 | Steiner et al. |
| 6,485,905 B2 | 11/2002 | Hefti |
| 6,508,273 B1 | 1/2003 | Van Den Berg |
| 6,626,416 B2 | 9/2003 | Sharma et al. |
| 6,719,535 B2 | 4/2004 | Rakestraw et al. |
| 6,895,964 B2 | 5/2005 | McAuliffe et al. |
| 6,908,770 B1 | 6/2005 | McDevitt et al. |
| 7,041,481 B2 | 5/2006 | Anderson |
| 7,955,864 B2 | 6/2011 | Cox et al. |
| 8,361,807 B2 | 1/2013 | Wiyatno et al. |
| 8,765,485 B2 * | 7/2014 | Link ................ B01F 5/0655 436/180 |
| 9,140,630 B2 | 9/2015 | Wiyatno et al. |
| 2001/0049148 A1 | 12/2001 | Wolk et al. |
| 2002/0159919 A1 | 10/2002 | Churchill |
| 2003/0006140 A1 | 1/2003 | Vacca et al. |
| 2003/0013200 A1 | 1/2003 | Pai et al. |
| 2003/0145894 A1 | 8/2003 | Burns |
| 2003/0162213 A1 | 8/2003 | Fuller et al. |
| 2003/0194709 A1 | 10/2003 | Yang |
| 2003/0199081 A1 | 10/2003 | Wilding et al. |
| 2003/0213905 A1 | 11/2003 | Lennon et al. |
| 2004/0014239 A1 | 1/2004 | Wolk et al. |
| 2004/0058450 A1 | 3/2004 | Pamula et al. |
| 2004/0180346 A1 * | 9/2004 | Anderson ............ C12Q 1/6806 435/6.18 |
| 2004/0194562 A1 | 10/2004 | Brockman et al. |
| 2004/0234966 A1 | 11/2004 | Bryning et al. |
| 2004/0241721 A1 | 12/2004 | Gjerde et al. |
| 2004/0248144 A1 | 12/2004 | Mir |
| 2005/0087122 A1 * | 4/2005 | Ismagliov ............ B01F 5/0646 117/2 |
| 2005/0130173 A1 | 6/2005 | Leaman et al. |
| 2005/0172476 A1 | 8/2005 | Stone et al. |
| 2005/0223822 A1 | 10/2005 | Ozbal |
| 2006/0037657 A1 | 2/2006 | Shibata et al. |
| 2006/0056904 A1 | 3/2006 | Haselton et al. |
| 2006/0163385 A1 | 7/2006 | Link et al. |
| 2007/0039866 A1 | 2/2007 | Schroeder |
| 2007/0054266 A1 | 3/2007 | Sato et al. |
| 2007/0068573 A1 | 3/2007 | Cox |
| 2007/0117212 A1 * | 5/2007 | Kautz ............... B01L 3/502784 436/137 |
| 2007/0122314 A1 | 5/2007 | Strand et al. |
| 2007/0141593 A1 | 6/2007 | Lee |
| 2007/0195127 A1 | 8/2007 | Ahn et al. |
| 2008/0023330 A1 | 1/2008 | Viovy et al. |
| 2010/0209916 A1 | 8/2010 | Zon |
| 2011/0171748 A1 | 7/2011 | Cox et al. |
| 2017/0361318 A1 * | 12/2017 | Weitz ................. B01F 13/0074 |

OTHER PUBLICATIONS

"Droplet Control for Microfluidics," Science vol. 309, Aug. 2005, 887-888, Ajdari, et al., USA.

"Miniaturised nucleic acid analysis," Lab on a Chip Royal Society of Chemistry Cambridge, 2004, 534-546, Auroux, Pierre-Alain, et al., European Patent Office.

"Microfabricated Structures for Integrated DNA Analysis," Proc. Natl. Acad. Sci., May 1996, 5556-5561, Burns, et al., USA.

"A Closed-Cycle Capillary Polymerase Chain Reaction Machine," Analytical Chemistry American Chemical Society vol. 73 No. 9, 2001, 2018-2021, Chiou J., et al.

"Continuous segmented-Flow Polymerase Chain Reaction for High-Throughput Miniaturized DNA Amplification," Anal. Chem vol. 75(1), 2003, 1-7, Curcio, Mario, et al., USA.

"On-line integration of PCR and cycle sequencing in capillaries: from human genomic DNA directly to called bases," Nucleic Acids Research; vol. 31 No. 8, 2003, 1-7, Hashimoto, et al., USA.

"Microfabricated systems for nucleic acid analysis," Critical Reviews in Clinical Laboratory Sciences CRC Press, Jan. 2004, 429-465, Obeid, P. J., et al., Boca Raton, FL USA.

International Search Report dated Jan. 17, 2008, from PCTUS0632640.

Written Opinion of International Searching Authority dated Jan. 17, 2008 from PCTUS0632640.

"Miniaturized flow-through PCR with different template types in a silicon chip thermocycler," Lab on a Chip; vol. (1), 2001, 42-49, Schneegass, et al., USA.

(56) References Cited

OTHER PUBLICATIONS

"Dynamic Pattern Formation in a Vesicle-Generating Microfluidic Device," Physical Review Letters vol. 86 No. 18, Apr. 2001, 4163-4166, Thorsen, et al., USA.

* cited by examiner

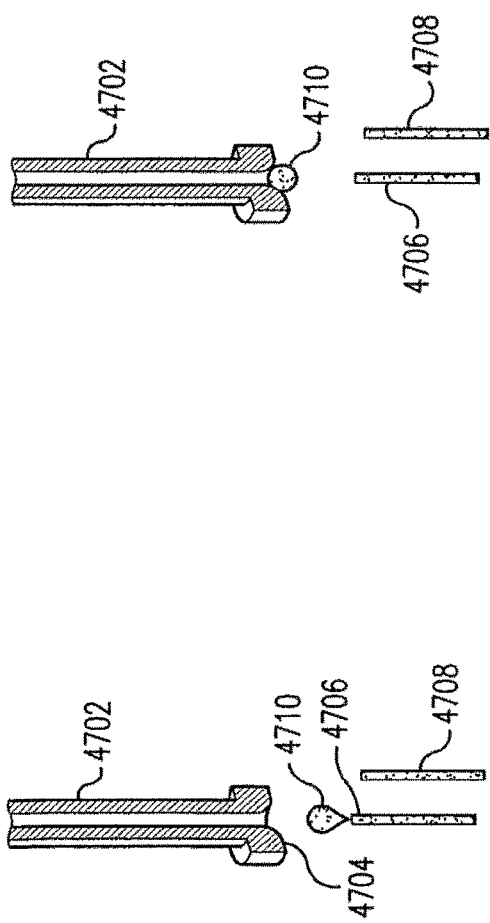
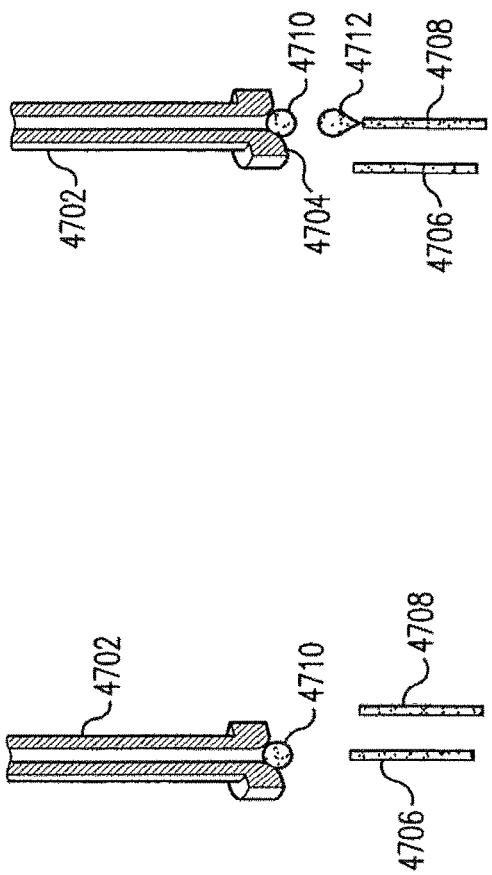
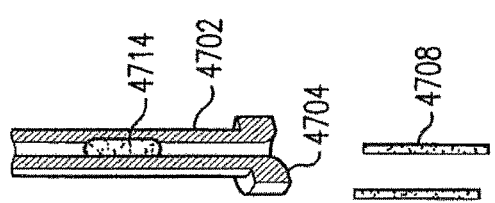
FIG. 47A
FIG. 47B
FIG. 47C
FIG. 47D
FIG. 47E

DEVICE AND METHOD FOR MAKING DISCRETE VOLUMES OF A FIRST FLUID IN CONTACT WITH A SECOND FLUID, WHICH ARE IMMISCIBLE WITH EACH OTHER

CROSS-REFERENCE TO RELATED APPLICATIONS

The present application is a continuation of U.S. application Ser. No. 13/724,079, filed Dec. 21, 2012, which is a continuation of U.S. application Ser. No. 13/069,213, filed Mar. 22, 2011, now U.S. Pat. No. 8,361,807, which is a divisional of U.S. application Ser. No. 11/508,044, filed Aug. 22, 2006, now U.S. Pat. No. 7,955,864, and claims the benefit of earlier filed U.S. Provisional Patent Application No. 60/710,167, filed Aug. 22, 2005, U.S. Provisional Patent Application No. 60/731,133, filed Oct. 28, 2005, and U.S. Provisional Patent Application No. 60/818,197, filed Jun. 30, 2006, which are incorporated herein in their entireties by reference.

The present application claims the benefit of earlier filed U.S. Provisional Patent Application No. 60/710,167, filed Aug. 22, 2005, U.S. Provisional Patent Application No. 60/731,133, filed Oct. 28, 2005, and U.S. Provisional Patent Application No. 60/818,197, filed Jun. 30, 2006, which are incorporated herein in their entireties by reference.

INTRODUCTION

The section headings used herein are solely for organization purposes and are not to be construed as limiting the subject matter described in any way.

Large scale sequencing projects can involve cloning DNA fragments in bacteria, picking and amplifying those fragments, and performing individual sequencing reactions on each clone. Standard sequencing reactions can often be performed in 5 µl to 20 µl reaction volumes, even though only a small fraction of the sequencing product can be analyzed. Such cloning and sequencing protocols can be time consuming and can use relatively large sample and reagent volumes. The relatively large volumes can be wasteful in terms of expensive consumable reagents, and input sample quantity.

SUMMARY

Various embodiments of the present teachings relate to systems, apparatus, and/or methods for sample preparation that can be used for biochemical or molecular biology procedures involving different volumes, for example, small volumes such as micro-liter sized volumes or smaller.

According to the present teachings, the system can comprise an apparatus for generating discrete volumes of at least a first fluid in contact with a second fluid, wherein the first and second fluids are immiscible with each other, for example, discrete volumes of an aqueous liquid (herein "aqueous immiscible-fluid-discrete-volumes"), spaced-apart from one another by a spacing fluid that is immiscible with the immiscible-fluid-discrete-volumes. An immiscible-fluid-discrete-volume can be a partitioned segment in which molecular biology procedures can be performed. As used herein, an immiscible-fluid-discrete-volume can be one of many structures, three of which are: a fluid segment, a slug, and an emulsified droplet. In some embodiments, immiscible-fluid-discrete-conduits are formed and/or processed in a conduit.

This paragraph defines a conduit as it is used herein. A conduit can be any device in which an immiscible-fluid-discrete-volume can be generated, conveyed, and/or flowed. For example, a conduit as defined herein can comprise any of a duct, a tube, a pipe, a channel, an open top channel, a closed channel, a capillary, a hole or another passageway in a solid structure, or a combination of two or more of these, as long as the spaces defined by the respective solid structures are in fluid communication with one another. A conduit can comprise two or more tubes or other passageways connected together, or an entire system of different passageways connected together. An exemplary conduit can comprise an immiscible-fluid-discrete-volume-forming tube, thermal spirals, valve passageways, a processing conduit, junctions, and the like components all connected together to form one or more fluid communications therethrough, which system is also referred to herein as a main processing conduit. Examples of solid structures with holes or passageways therein that can function as conduits are manifolds, T-junctions, Y-junctions, rotary valves, and other valves. Thus, when connected to conduits, such structures can be considered part of a conduit as defined herein.

This paragraph defines a fluid segment, as it is used herein. A fluid segment is a discrete volume that has significant contact with one or more conduit wall(s), such that a cross-sectional area of the fluid segment is the same size and shape as the cross-sectional area of the conduit it contacts. At least a portion of a fluid segment fully fills the cross-sectional area of the conduit, such that the immiscible fluid adjacent it in the conduit can not flow past the fluid segment. The entire longitudinal length of the fluid segment may not contact the conduit walls.

This paragraph defines a slug as used herein. A slug is a discrete volume that has at least a portion of which has approximately the same cross-sectional shape as the conduit in which it exists, but a smaller size. The smaller size is due to the insignificant contact, if any, of the slug with the conduit wall(s). A slug can have a cross-sectional dimension between approximately 0.5 and approximately 1.0 times the maximum dimension of a cross sectional area of the conduit. If the conduit has a circular cross section, the cross-sectional area of a slug can be concentric with the conduit's cross-sectional area, but it does not have to be, such as, for example, when the conduit is horizontal and, due to different specific gravities, one fluid rises toward the top of the cross-sectional area of the conduit under the influence of gravity. A slug can be free of contact with the conduit walls. When not moving relative to the conduit, a slug can have "feet" that appear as nibs or bumps along an otherwise smoothly appearing round surface. It is theorized that the feet at the bottom of the slug may have contact with the conduit wall. In contrast to a fluid segment, the contact a slug can have with the conduit wall(s) still permits the immiscible fluid adjacent it in the conduit to flow past the slug.

The "slugs" formed by the teachings herein, separated by spacing fluid, can merge together to form larger slugs of liquid, if contacted together. The ability of the slugs, for example, aqueous slugs, described and taught herein, to merge together with each other, facilitates the downstream addition of aqueous reagents to the slugs.

This paragraph defines an emulsified droplet, as used herein. An emulsified droplet is a discrete volume that has no contact with the walls of the conduit. The size of an emulsified droplet is not necessarily constrained by the conduit, and examples of emulsified droplets described in the prior art range in size from about 1 femtoliter to about 1 nanoliter. The shape of an emulsified droplet is not constrained by the conduit, and due to the difference in surface-energies between it and the continuous phase liquid in which it is dispersed, it is generally spherical. It can have a maximum dimension that is not equal to, nor approximately equal to, but much less than the maximum dimension of the cross-sectional area of the conduit, for example, 20%, 10%, 5% or less. An emulsified droplet will not merge upon contact with another emulsified droplet to form a single, larger discrete volume, without external control. Put another way, an emulsified droplet is a stable discontinuous phase in a continuous phase.

A conduit can contain more than one emulsified droplet, but not more than one slug or fluid segment, at any cross-sectional location. Thus, a first emulsified droplet does not necessarily impede the movement of a second emulsified droplet past it, where as a fluid segment and a slug necessarily do not permit the passage of another fluid segment or slug past them, respectively. If two fluid segments are separated by a fluid with which the first and second of the two fluids is each immiscible, then the immiscible fluid also forms a discrete volume. It is likely that it has significant contact with the conduit walls and thus is another fluid segment.

Whether two immiscible fluids, when present in a conduit, form fluid segments of the first and second of the two immiscible fluids, slugs of the first immiscible fluid, or emulsified droplets of the first immiscible fluid depends on at least the method of introduction of each fluid into the conduit, the relative surface energies of the first immiscible fluid, the second immiscible fluid, the conduit material, and the contact angle each forms with the other two materials, respectively, and the volume of the discrete volume of first immiscible fluid. Thus, it is recognized that these definitions are merely reference points on a continuum, the continuum of the shape and size of discrete volumes of a first immiscible fluid in a conduit, and discrete volumes will exist that, when described, fall between these definitions.

The molecular biology procedures can, for example, utilize proteins or nucleic acids. Procedures with nucleic acids can comprise, for example, a PCR amplification and/or nucleic acid analysis of an amplification product. The PCR amplification and/or nucleic acid analysis of an amplification product can comprise an integrated DNA amplification/DNA sequencing method.

Using the apparatus, methods, and/or systems provided in this application, a polymerase chain reaction (PCR) amplification of single DNA molecules can be performed, for example, to obtain amplicons. The amplified DNA or amplicons can then be used in a sequencing reaction and then be sequenced in small volumes. Other manipulations of nucleic acids or proteins can also be accomplished, for example, DNA hybridization reactions or antibody-antigen binding assays.

The apparatus, system and/or methods described herein can also be used in conjunction with U.S. Provisional Patent Application No. 60/710,167 entitled "Sample Preparation for Sequencing" to Lee et al., filed Aug. 22, 2005, U.S. Provisional Patent Application No. 60/731,133 entitled "Method and System for Spot Loading a Sample" to Schroeder et al., filed Oct. 28, 2005, and systems described in U.S. Provisional Patent Application No. 60/818,197 filed Jun. 30, 2006, each of which are incorporated herein in their entireties by reference.

An exemplary type of sample preparation can be used for genotyping, gene-expression, methylation analysis, and/or directed medical sequencing (Variant SEQr™, for example, an Applied Biosystems product comprising primers for resequencing genes and detecting variations) that requires multiple liquids to be brought together in an aqueous discrete volume. For example, in a gene-expression application, each aqueous discrete volume can contain individual primer sets. The sample to be analyzed, for example, complementary DNA (cDNA), can be added to each aqueous discrete volume. In the VariantSEQr™ application, for example, an aqueous discrete volume can comprise a primer set and genomic DNA can be added to that discrete volume. According to various embodiments, a system and method are provided that are able to generate discrete volumes with unique content. According to various embodiments of the present teachings, sipping, other aspirating, or other techniques to generate immiscible-liquid, discrete volumes can be used. According to various embodiments, an immiscible-liquid, discrete volume of at least an aqueous sample fluid can be generated in a tube by alternately drawing into the tube the aqueous sample fluid and spacing fluid, with which the aqueous sample fluid is immiscible, from a single container or well containing both fluids or from different containers or wells each containing one of the two fluids.

According to various embodiments, the distal tip or introduction end of an immiscible-fluid-discrete-volume-forming tube can be brought into contact with an oil layer disposed on top of an aqueous sample fluid in a well as the tip is removed from the aqueous sample fluid, such that the action can be used to rinse off the tip and avoid tip contamination as the tube is transferred to a different well.

According to various embodiments, the present teachings provide an apparatus that can comprise a first conduit, a second conduit, a first pump, and a second pump, operatively connected together. The first conduit can have an outer perimeter and a length. The second conduit can have an inner perimeter, wherein at least a portion of the length of the first conduit is inside of the second conduit, thereby defining a space between the outer perimeter of the first conduit and the inner perimeter of the second conduit. The first pump can be operatively connected to the first conduit and configured to flow fluids through the first conduit in a first direction. The second pump can be operatively connected to the second conduit and configured to flow a second fluid through the second conduit in a second direction that is opposite the first direction.

According to various embodiments, the apparatus can comprise a control unit configured to synchronize actuation of the first pump and the second pump. In some embodiments, the apparatus can comprise a conduit positioner configured to axially move one of the first conduit and the second conduit with respect to the other, and can further comprise a control unit configured to synchronize actuation of the first pump, the second pump, and the conduit positioner.

In some embodiments, the first conduit has an end surface, the second conduit has an end surface, and the end surface of the first conduit can be beyond the end surface of the second conduit. In some embodiments, the second conduit can comprise a block having a through-hole. In some embodiments, the first conduit can comprise an end surface and the end surface can be disposed within the through-hole of the block. If the second conduit comprises a block, the block can comprise a passageway formed therein and having a first end at the through-hole and extending away from the through-hole. In such embodiments, the apparatus can further comprise a third pump operatively connected to the passageway and configured to draw fluid from the through-hole into the passageway.

In some embodiments, the first conduit can have an inner diameter, and the inner diameter can be from about 10 microns to about 2000 microns. The second conduit can have an inner diameter, and the inner diameter can be from about 20 microns to about 5000 microns, and can be large enough to accommodate the outer periphery of the first conduit.

According to various embodiments, a system is provided that can comprise an apparatus as described herein and a supply of oil, wherein the second pump can be operatively connected to the supply of oil. In some embodiments, the system can comprise a sample liquid disposed in a sample container, and a conduit positioner can be provided that is configured to move the first conduit into the sample container and into contact with the sample liquid.

According to various embodiments, a method is provided that comprises pumping a first fluid in a first direction in a space between an outer perimeter of a first conduit and an inner perimeter of a second conduit, and drawing the first fluid past an end surface of the first conduit, and into the first conduit in a second direction that is opposite the first direction. The method can comprise positioning the first conduit into a receptacle containing a second fluid and contacting the second fluid with the tip of the first conduit, and drawing at least a portion of the second fluid into the first conduit. In some embodiments, the method can comprise causing a reaction of the second fluid within the first conduit.

According to various embodiments, the method can comprise positioning at least one of an end surface of the first conduit and an end surface of the second conduit such that the end surface of the first conduit extends past the end surface of the second conduit. In some embodiments, the method can involve positioning at least one of the end surface of the first conduit and the end surface of the second conduit such that the end surface of the first conduit is flush with the end surface of the second conduit, or such that the end surface of the first conduit is inside the second conduit.

Various embodiments of the present teachings relate to an apparatus, system, or method for sample preparation and/or sample deposition. The sample preparation can be used for biochemical or molecular biology procedures involving small volumes, for example, microliter-sized volumes or smaller. The system can comprise an apparatus comprising at least a first tube inside a second tube, wherein both tubes are in fluid communication with pump(s) for providing immiscible-fluid-discrete-volumes of a first liquid separated by a second fluid, for example, immiscible-fluid-discrete-volumes of water or an aqueous-based liquid, separated by oil. The immiscible-fluid-discrete-volumes can form small partitioned segments to be used in molecular biology procedures. The molecular biology procedures can comprise, for example, a PCR amplification and/or nucleic acid analysis of the amplification product. The PCR amplification and/or nucleic acid analysis of the amplification product can comprise an integrated DNA amplification/DNA sequencing method.

According to various embodiments, the present teachings provide a method that generates discrete, small volumes of a target or sample liquid, for example, 1 µl or less, in spacing fluid. The present teachings provide an apparatus that can generate aqueous immiscible-fluid-discrete-volumes separated by oil, or other non-aqueous liquid that is immiscible with water, in capillaries, channels, and other conduits.

Interfacing or otherwise integrating the apparatus, methods, and/or systems provided in this application that generate immiscible-fluid-discrete-volumes with downstream processing of the contents in the immiscible-fluid, discrete volumes, microbiological processes can be performed in the immiscible-fluid-discrete-volumes. These downstream processes can include, for example, polymerase chain reaction (PCR) amplification of single DNA molecules to obtain, for example, amplicons. The amplified DNA or amplicons can then be used in a sequencing reaction and be sequenced using small volumes. Other manipulations of nucleic acids or proteins can also be accomplished, for example, DNA hybridization reactions or antibody-antigen binding assays.

An apparatus is provided that can be used, for example, 1) to prepare spaced-apart aqueous immiscible-fluid-discrete-volumes separated by an immiscible spacing fluid, for example, oil, for carrying out reactions in microliter-sized or smaller volumes, and 2) for rinsing a conduit tip between drawing a first sample fluid and a second sample fluid to avoid contamination of the second sample fluid with the first sample fluid.

According to various embodiments, an apparatus is provided comprising an inner tube, an outer tube, a first pump and a second pump. The inner tube comprises an inner surface, an outer surface, an outer diameter, and a first open end, and the outer tube comprises an inner surface, an inner diameter, an outer surface, and a second open end, where the inner tube is positioned within the outer tube and the inner diameter of the outer tube is greater than the outer diameter of the inner tube such that a fluid can be flowed between the outer surface of the inner tube and the inner surface of the outer tube. The first pump is in fluid communication with the inner tube, wherein the first pump is configured to flow fluids the inner tube in a first direction; and the second pump is in fluid communication with the outer tube, wherein the second pump is configured to flow a fluid the outer tube in a second direction opposite the first direction.

According to various embodiments, a method is provided comprising: pumping a first fluid in a first direction in a space between the outer diameter of an inner tube and the inner diameter of an outer tube; drawing the first fluid through a tip of the inner tube and in the inner tube in a second direction, wherein the second direction is opposite the first direction; and, positioning the open end of the inner tube beyond the open end of the outer tube.

According to various embodiments, the present teachings provide a system for aspirating liquids, including at least one differential pressure source. In some embodiments, the system can comprise an aspirating tube in communication with the at least one differential pressure source, and comprising an intake tip. In some embodiments, the system can comprise at least one fluid container in communication with the intake tip, the at least one fluid container containing at least a first fluid and a second fluid, the first fluid and the second fluid being immiscible with each other. In some embodiments, the system can comprise at least one intake tip positioning unit configured to alternately aspirate the first fluid and the second fluid by raising and lowering one of the at least one fluid container and the intake tip relative to the other, and using differential pressure delivered by the at least one differential pressure source.

According to various embodiments, the present teachings provide a method comprising disposing an intake tip of an aspirating conduit in a fluid container comprising at least first and second fluids that are immiscible with one another and form layers in the fluid container. In some embodiments, the method can comprise aspirating the first fluid through the intake tip and into the aspirating conduit. In some embodiments, the method can comprise moving one of the intake tip and the fluid container up or down relative to the other until the intake tip is immersed in the second fluid in the fluid container. In some embodiments, the method can comprise aspirating the second fluid through the intake tip and into the aspirating conduit.

According to various embodiments, the present teachings provide a method comprising flowing a first fluid into a through-hole of a slider housed in a slider housing and positioned at a first position. In some embodiments, the method can comprise shifting the slider from the first position to a second position relative to the slider housing, to align the through-hole of the slider with an output conduit containing a second fluid that is immiscible with the first fluid. In some embodiments, the method can comprise moving the first fluid from inside the through-hole out of the through-hole and into the output conduit, with a source of additional second fluid to form a discrete volume of the first fluid in contact with the second fluid.

According to various embodiments, the present teachings provide a system comprising a housing, a slider arranged in the housing for sliding movement therein between at least a first position and a second position. In some embodiments, the slider can comprise a through hole, and a first fluid supply conduit operatively connected to a first end of the through-hole when the slider is in the first position. In some embodiments, the system can comprise waste conduit operatively connected to a second, opposite end of the through-hole when the slider is in the first position. In some embodiments, the system can comprise a second fluid supply conduit operatively connected to the first end of the through-hole when the slider is in the second position. In some embodiments, the system can comprise an immiscible-fluid-discrete-volume-forming conduit operatively connected to the second, opposite end of the through-hole when the slider is in the second position. In some embodiments, the system can comprise a supply of a first fluid operatively connected to the first fluid supply conduit. In some embodiments, the system can comprise a supply of a second fluid operatively connected to the second fluid supply conduit, wherein the second fluid and the first fluid are immiscible with respect to one another.

According to various embodiments, the present teachings provide a method comprising merging together at an junction of a first pair of conduits and a second pair of conduits a first fluid and a second fluid. In some embodiments, the first fluid can comprise a spacing fluid and the second fluid can comprise an immiscible-discrete-volume-forming fluid that is immiscible with the first fluid, such that a set of immiscible-fluid-discrete-volumes of the second fluid are formed that are spaced apart from one another by the first fluid, wherein at least one of the first fluid, the second fluid, and the set of immiscible-fluid-discrete-volumes flows through a rotary valve comprising a stator and a rotor. In some embodiments, the first pair of conduits can comprise a first conduit and a second conduit that each pass through the stator. In some embodiments, the second pair of conduits can comprise a third conduit and a fourth conduit that each pass through the stator. In some embodiments, the rotor can comprise a through-hole that, in a first position, fluidly communicates the first conduit with the second conduit, and in a second position fluidly communicates the third conduit with the fourth conduit. In some embodiments, the method can further comprise rotating the rotor from the first position to the second position.

According to various embodiments, the present teachings provide a system comprising a rotary valve comprising a stator and a rotor. In some embodiments, the system can comprise a first conduit in operatively connected to the rotary valve. In some embodiments, the system can comprise a second conduit operatively connected to the rotary valve. In some embodiments, the system can comprise a junction of the first conduit and the second conduit in the rotor of the rotary valve. In some embodiments, the system can comprise a first fluid comprising a spacing fluid in fluid communication with the first conduit. In some embodiments, the system can comprise a second fluid comprising an immiscible-discrete-volume-forming fluid, that is immiscible with the first fluid, in fluid communication with the second conduit. In some embodiments, the system can comprise a third conduit operatively connected to the rotary valve and in fluid communication with the intersection. In some embodiments, the system can comprise a fourth conduit operatively connected to the rotary valve and in fluid communication with the intersection, wherein the rotor comprises a through-hole that, in a first position, fluidly communicates the first conduit with the second conduit, and in a second position fluidly communicates the third conduit with the fourth conduit.

According to various embodiments, the present teachings provide a system comprising an immiscible-fluid-discrete-volume-forming conduit comprising an intake end. In some embodiments, the system can comprise an electro-wetting device comprising one or more electro-wetting pathways for transporting one or more droplets, and an output site along at least one of the one or more electro-wetting pathways. In some embodiments, the system can comprise a positioning unit for positioning the intake tip adjacent or at the output site.

According to various embodiments, the present teachings provide a method comprising transporting a first droplet of a first fluid along an electro-wetting pathway of an electro-wetting device. In some embodiments, the method can comprise merging the first droplet with a second droplet of a second fluid that is miscible with the first fluid, to form a third droplet. In some embodiments, the method can comprise drawing the third droplet into an immiscible-fluid-discrete-volume-forming conduit.

According to various embodiments, the present teachings provide a device comprising a substrate and an elastically deformable bottom cover. In some embodiments, the substrate can comprise a bottom wall having a central axis of rotation and a lower surface, an annular wall extending upward from the bottom wall and defining a central reservoir radially inward with respect to the annular wall, a plurality of through-holes in the bottom wall in the central reservoir, a plurality of radial reservoirs formed in the substrate and disposed radially outward with respect to the annular wall, each radial reservoir comprising at least one sidewall and a bottom, and a plurality of through-holes, at least one in the bottom of each radial reservoir. In some embodiments, the elastically deformable bottom cover can be attached to the lower surface of the bottom wall and spaced-apart from portions of the lower surface of the bottom wall, such that a respective radial fluid channel is provided between each through-hole in the central reservoir and a respective through-hole of the plurality of through-holes in the radial reservoirs. According to various embodiments, the present teachings provide a system comprising a device comprising a substrate as described in the foregoing, a rotatable support comprising a holder for holding the device, a drive unit for rotating the rotatable support, while holding the device, about the central axis of rotation, and a plunger configured to press against the bottom cover.

According to various embodiments, the present teachings provide a method comprising forming a first droplet of a second fluid in a first fluid, wherein the first fluid and the second fluid are immiscible with respect to one another and have different densities. In some embodiments, the method can comprise moving at least one of the first droplet and an intake tip of a conduit relative to one another such that the first droplet is disposed adjacent the intake tip. In some embodiments, the method can comprise drawing the first droplet and an amount of the first fluid through the intake tip and into the conduit.

According to various embodiments, the present teachings provide a method comprising providing a device, the device comprising a substrate, the substrate comprising a bottom wall having a central axis of rotation and a lower surface, an annular wall extending upward from the bottom wall and defining a central reservoir radially inward with respect to the annular wall, a first through-hole extending through the bottom wall in the central reservoir, a radial reservoir formed in the substrate and disposed radially outward with respect to the annular wall, the radial reservoir comprising at least one sidewall and a bottom, and a second through-hole extending through the bottom of the radial reservoir. In some embodiments, the provided device can further comprise an elastically deformable bottom cover attached to the lower surface of the bottom wall and spaced-apart from a portion of the lower surface of the bottom wall such that a respective radial fluid channel is provided between the first through-hole and the second through hole, wherein the central reservoir contains a first fluid, the radial fluid channel comprises a second fluid, the second fluid is less dense than the first fluid, the first fluid and the second fluid are immiscible with respect to one another. In some embodiments, the method can comprise forcing the elastically deformable bottom cover upwardly toward the lower surface of the bottom wall to create positive pressure in the respective radial fluid channel that forces a droplet of the second fluid to exit the first through-hole and enter the central reservoir.

According to various embodiments, the present teachings provide a system comprising an immiscible-fluid-discrete-volume-forming conduit. In some embodiments, the system can comprise a magnetohydrodynamic pump device comprising one or more magnetohydrodynamic pumps configured to transport one or more immiscible-fluid-discrete-volumes to the immiscible-fluid-discrete-volume-forming conduit. In some embodiments, the system can comprise a supply of a first fluid operatively connected to the one or more magnetohydrodynamic pumps. In some embodiments, the system can comprise a supply of a second fluid operatively connected to the one or more magnetohydrodynamic pumps, wherein the second fluid is immiscible with the first fluid.

According to various embodiments, the present teachings provide a method comprising actuating a magnetohydrodynamic pump to transport a first droplet of a first fluid along a pathway of a device. In some embodiments, the method can comprise merging the first droplet with a second droplet of a second fluid that is miscible with the first fluid, to form an immiscible-fluid-discrete-volume. In some embodiments, the method can comprise forcing the immiscible-fluid-discrete-volume into an immiscible-fluid-discrete-volume-forming conduit.

According to various embodiments, the present teachings provide a conduit rinsing system comprising a tubular conduit including a tip and an outer surface. In some embodiments, the system can comprise a cleaning vessel comprising a top, a bottom, an outer annular wall, an inner annular wall having a top rim and an inner surface, a space provided between the outer annular wall and the inner annular wall, and at least one port formed in the bottom and communicating with the space, wherein the tip is disposed in the cleaning vessel between the top and the bottom. In some embodiments, the system can comprise a closure flap disposed between the top of the cleaning vessel and the top rim of the inner annular wall, the closure flap being spaced from the top rim, wherein a rinse space is provided between the inner surface of the inner annular wall and the outer surface of the conduit, and an opening is provided in the bottom and in fluid communication with the rinse space.

According to various embodiments, the present teachings provide a method comprising applying a negative pressure to a conduit system comprising an intake tip. In some embodiments, the method can comprise contacting the intake tip with a first fluid and a second fluid that is immiscible with the first fluid, while applying the negative pressure, to draw the first fluid and the second fluid into the conduit system and form a set of discrete volumes of the first fluid spaced apart from one another by the second fluid, the set moving in a first direction in the conduit system. In some embodiments, the method can comprise thereafter applying a positive pressure to the conduit system to push the set of discrete volumes in the conduit system.

According to various embodiments, flow rates for preparing aqueous immiscible-fluid-discrete-volumes can comprise rates of from about 1 picoliter/sec. to about 200 microliters/sec., and can be selected based on the inner diameter of the conduits through which the liquids are to be pumped. Tubing that can be used with this flow rate can comprise an inner diameter of from about 250 microns to about 1000 microns. In other embodiments, the inner diameter of the inner tube can be from about 10 microns to about 2000 microns, while the inner diameter of the outer tube can be from about 20 microns to about 5000 microns, for example, from about 35 microns to about 500 microns. Other diameters, however, can be used based on the characteristics of the immiscible-fluid-discrete-volume formation or rinsing system desired. In some embodiments, a tube having a 10 micron inner diameter is used with a flow rate of from about 8 to about 10 picoliters/second. In some embodiments, a tube having a 5000 micron inner diameter is used with a flow rate of from about 25 to about 200 microliters/second. In some embodiments, a tube having a 500 micron inner diameter is used with a flow rate of from about 0.25 to about 2.0 microliters/second.

In other embodiments, for example, when an apparatus of the present teachings is used for rinsing the tip of, for example, the inner tube of an apparatus, the flow rate can comprise a rate from about 0.1 microliter/sec. to about 1.0 microliter/sec.

According to various embodiments, a method is provided that uses an apparatus comprising a first tube arranged inside a second tube. The method comprises contacting an aqueous sample liquid with a non-aqueous spacing fluid that is immiscible with the aqueous sample to form a plurality of discrete volumes of the aqueous sample in a conduit separated from one another by the non-aqueous spacing fluid. The aqueous sample liquid can comprise a plurality of target nucleic acid sequences, wherein at least one of the discrete volumes comprises at least one target nucleic acid sequence. In some embodiments, at least 50% of the plurality of the discrete volumes in the inner conduit can each comprise a single target nucleic acid sequence. In various other embodiments, less than about 50% of the plurality of discrete volumes in the conduit can each comprise a single target nucleic acid sequence. In other embodiments, at least 1% or more, 5% or more, 10% or more, or 20% or more can have a single target nucleic acid sequence, for example, upon formation of the discrete volumes.

According to various embodiments, each of the plurality of discrete volumes in the inner conduit can comprise one or more respective oligonucleotide primers. Oligonucleotide primers can be chosen as determined by one of skill in the art to accomplish the desired objective. For example, universal primers can be used.

In some embodiments, further downstream processing of the prepared immiscible-fluid-discrete-volumes can be integrated with the system, of which embodiments are described herein. Such downstream processing can include amplifying the at least one target nucleic acid sequence in the first discrete volume in the conduit to form an amplicon, and thereafter subjecting the amplicon to a nucleic acid sequencing reaction. For such purposes, and in some embodiments, the discrete volumes or immiscible-fluid-discrete-volumes can comprise reaction components, for example, oligonucleotide primers. Various embodiments of downstream processing can include universal PCR, or can comprise up-front multiplexed PCR followed by decoding, for example, see WO 2004/051218 to Andersen et al., U.S. Pat. No. 6,605,451 to Marmaro et al., U.S. patent application Ser. No. 11/090,830 to Andersen et al., and U.S. patent application Ser. No. 11/090,468 to Lao et al., all of which are incorporated herein in their entireties by reference. Details of real time PCR can be found in Higuchi et al., U.S. Pat. No. 6,814,934 B1, which is incorporated herein by reference in its entirety.

Further devices, systems, and methods that can be used with or otherwise implement the present teachings include those described, for example, in U.S. patent application Ser. No. 11/507,735, filed Aug. 22, 2006, entitled "Apparatus, System, and Method Using Immiscible-Fluid-Discrete-Volumes," to Lee et al., in U.S. patent application Ser. No. 14/508,756, filed Aug. 22, 2006, entitled "Apparatus and Method of Microfluidic Control of Discrete Volumes of a First Fluid in Contact With a Second Fluid, Wherein the First and Second Fluids are Immiscible," to Cox et al., and in U.S. patent application Ser. No. 11/507,733 filed Aug. 22, 2006, entitled "Apparatus and Method for Depositing Processed Immiscible-Fluid-Discrete-Volumes," to Schroeder et al., which are herein incorporated in their entireties by reference.

DRAWINGS

The skilled artisan will understand that the drawings described below, are for illustration purposes only. The drawings are not intended to limit the scope of the present teachings in any way. In the drawings.

Figure 7:
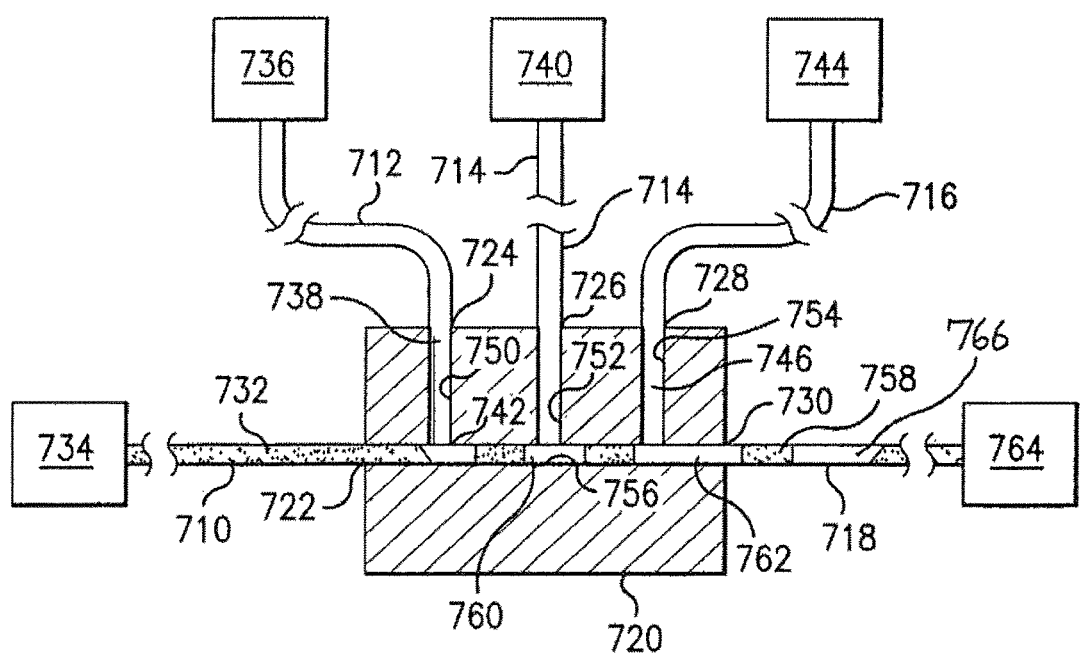
Figure 8:
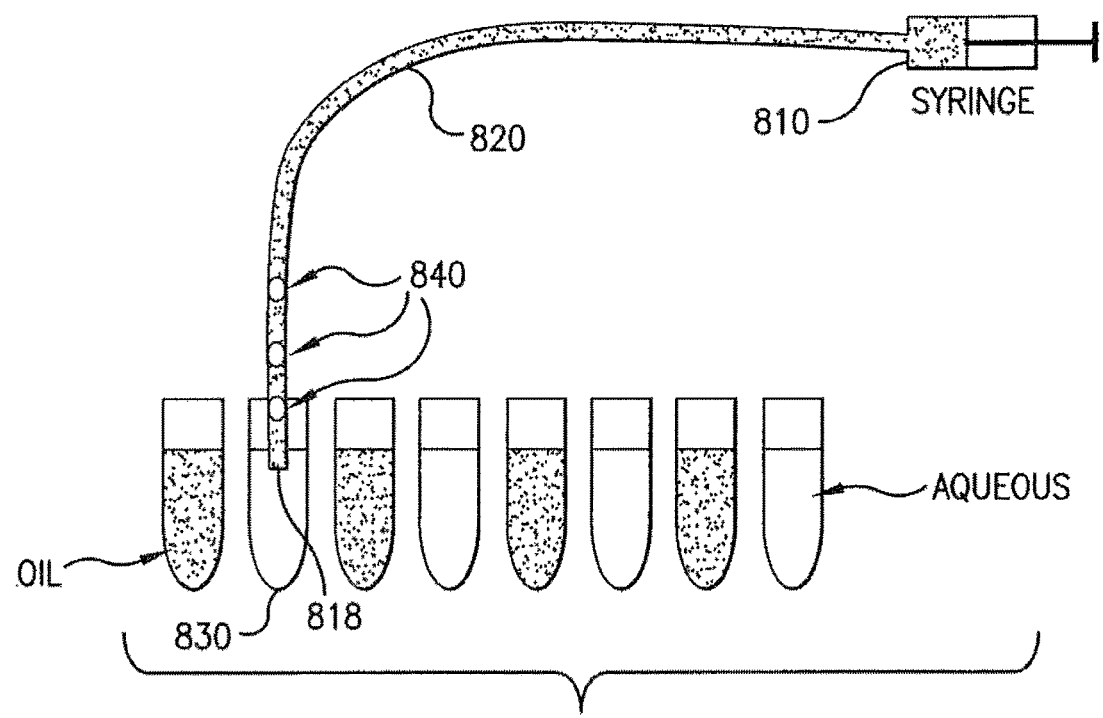
Figure 9A:
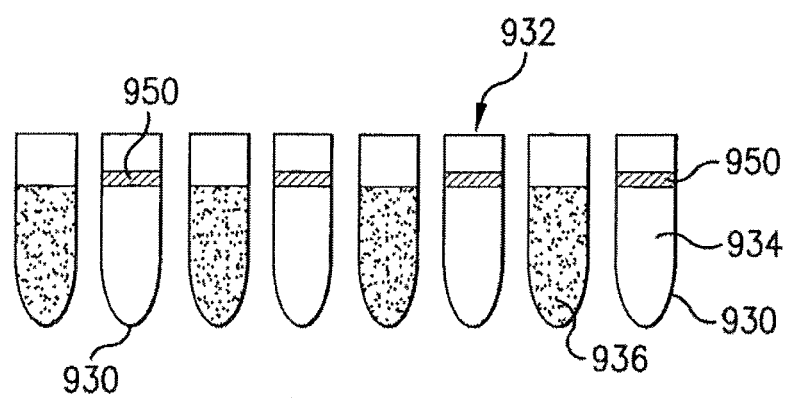
Figure 9B:
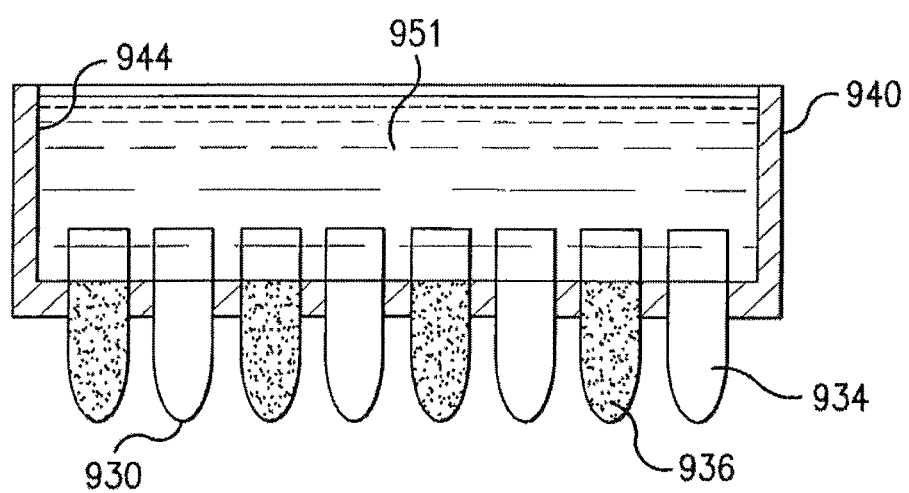
Figure 10A:
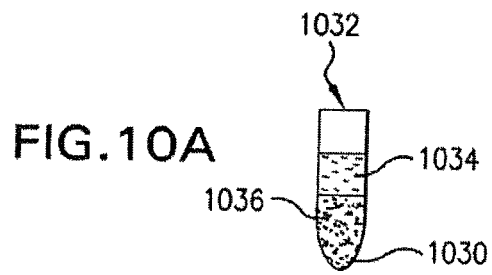
Figure 10B:
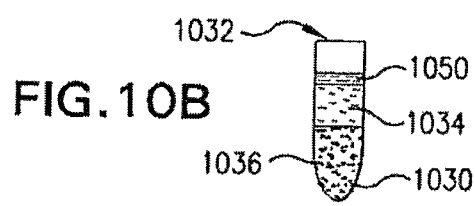
Figure 10C:
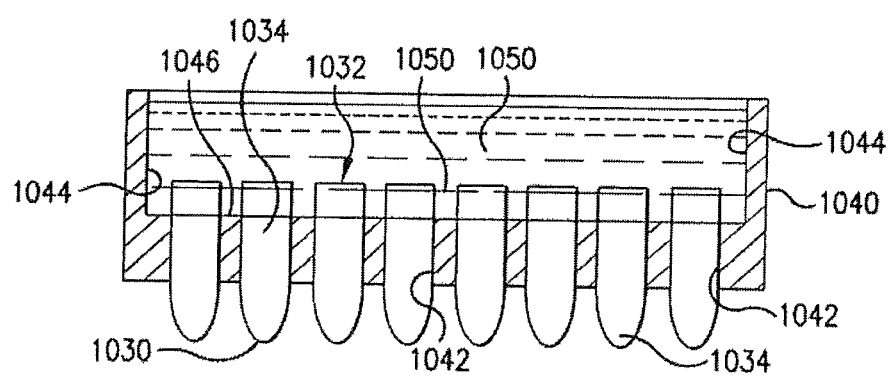
Figure 10D:
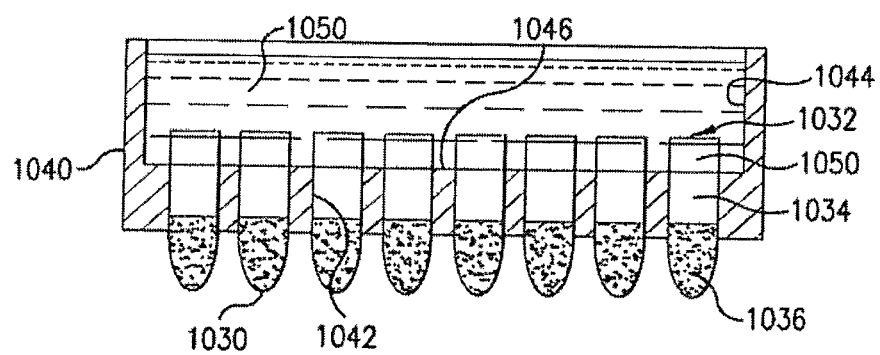
Figure 11:
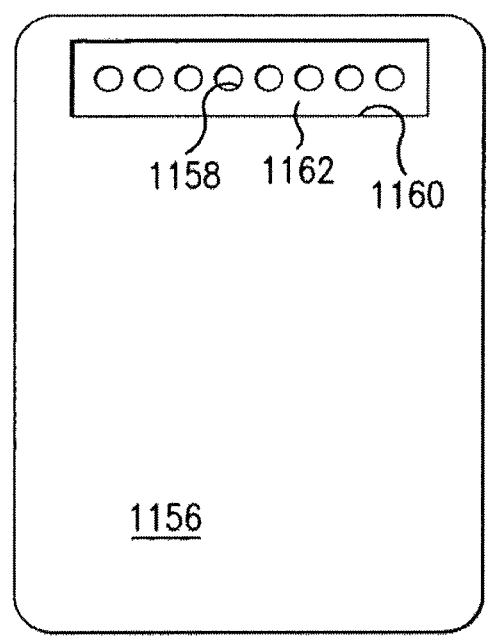
Figure 12A:
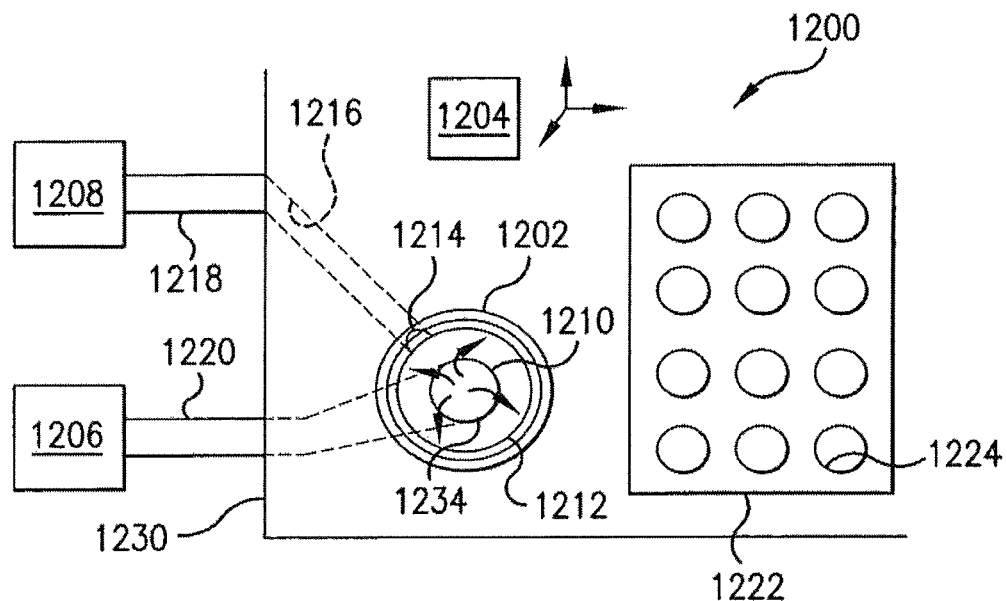
Figure 12B:
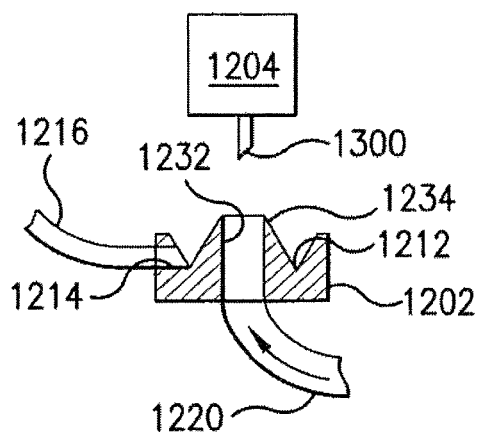
Figure 13:
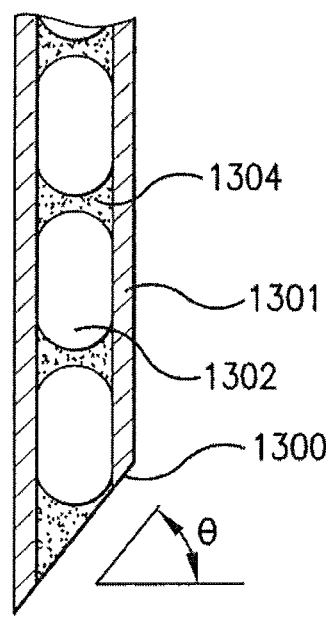
Figure 14:
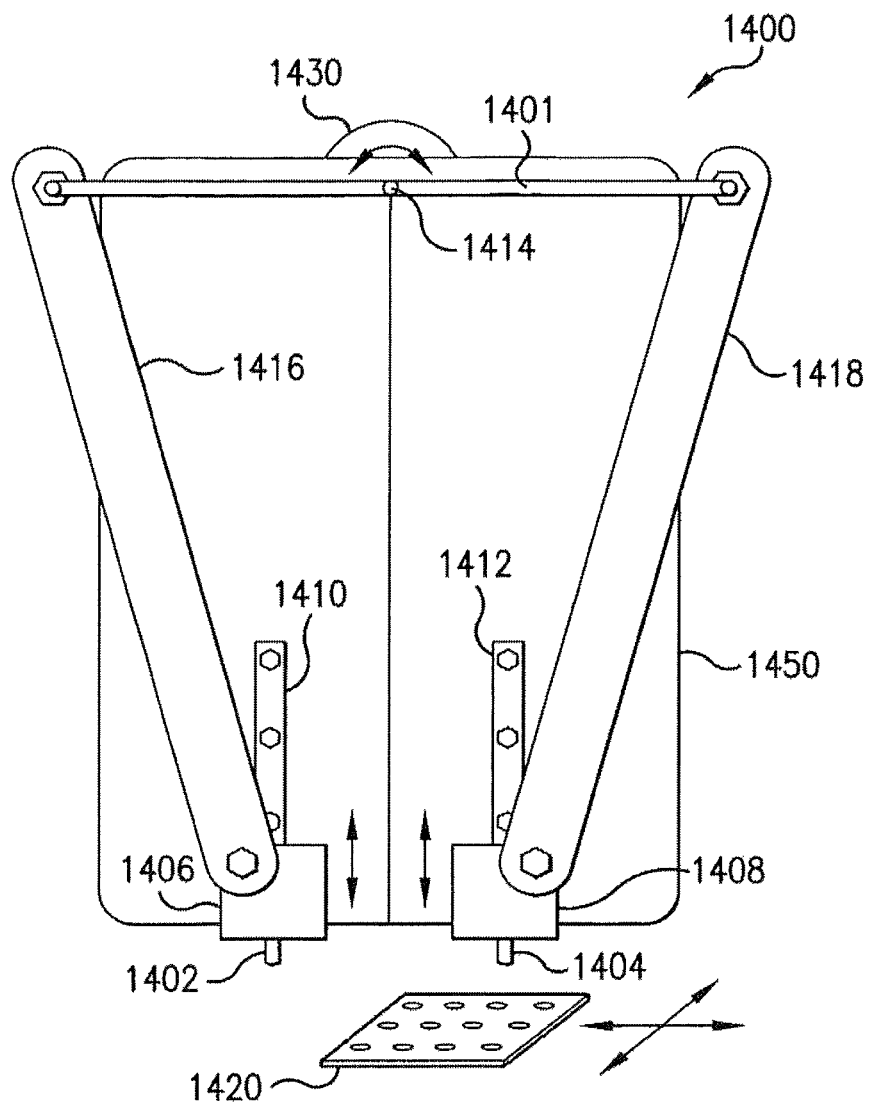
Figure 15:
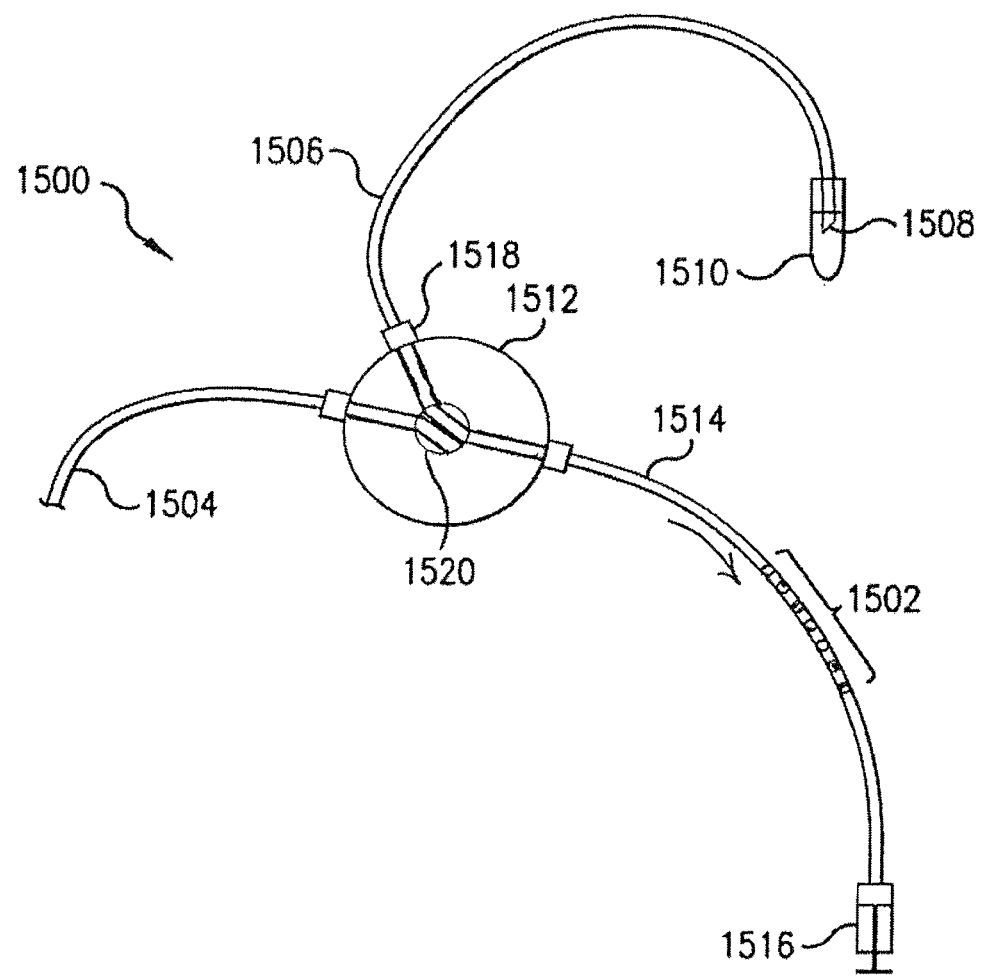
Figure 16:
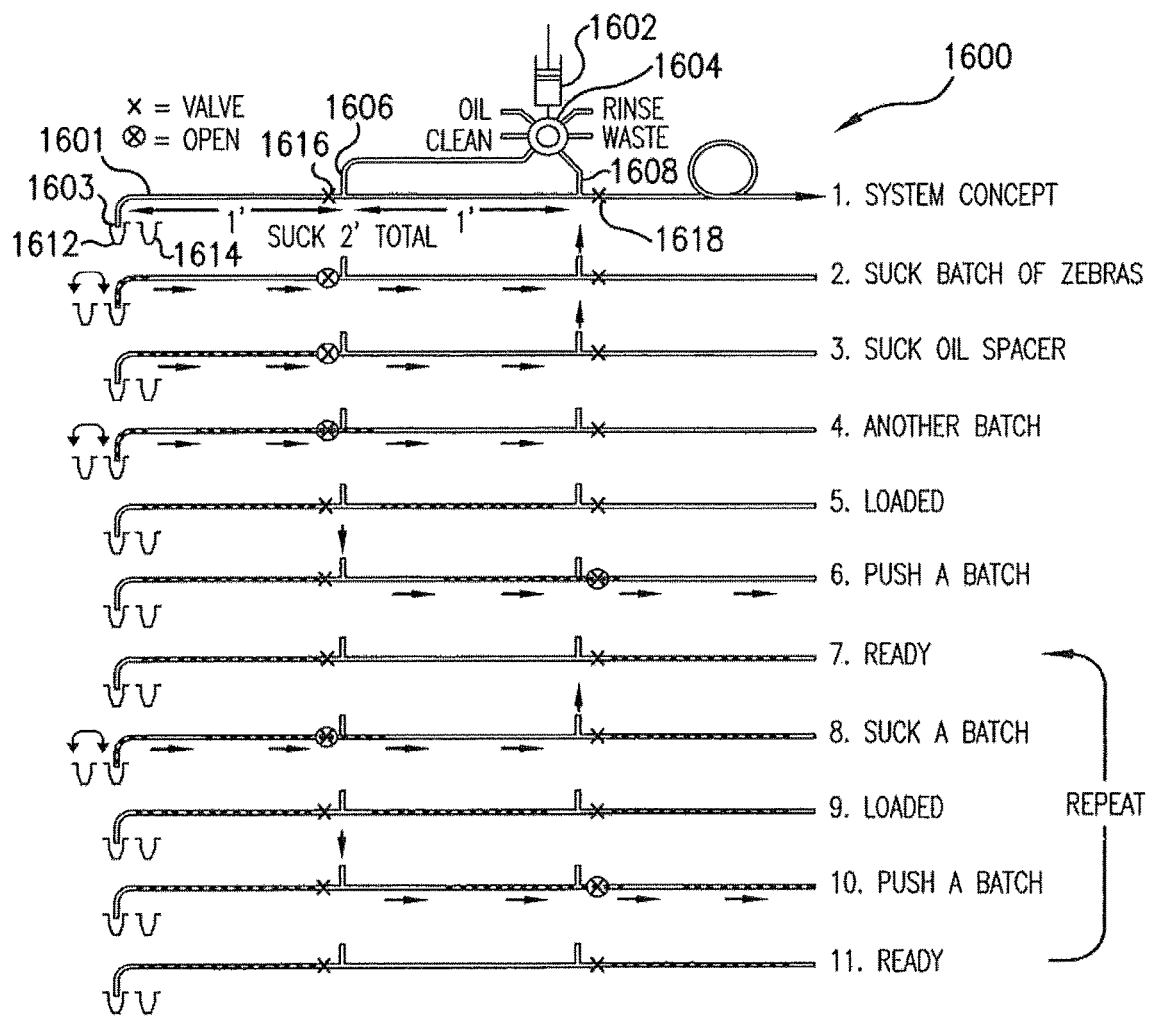
Figure 17:
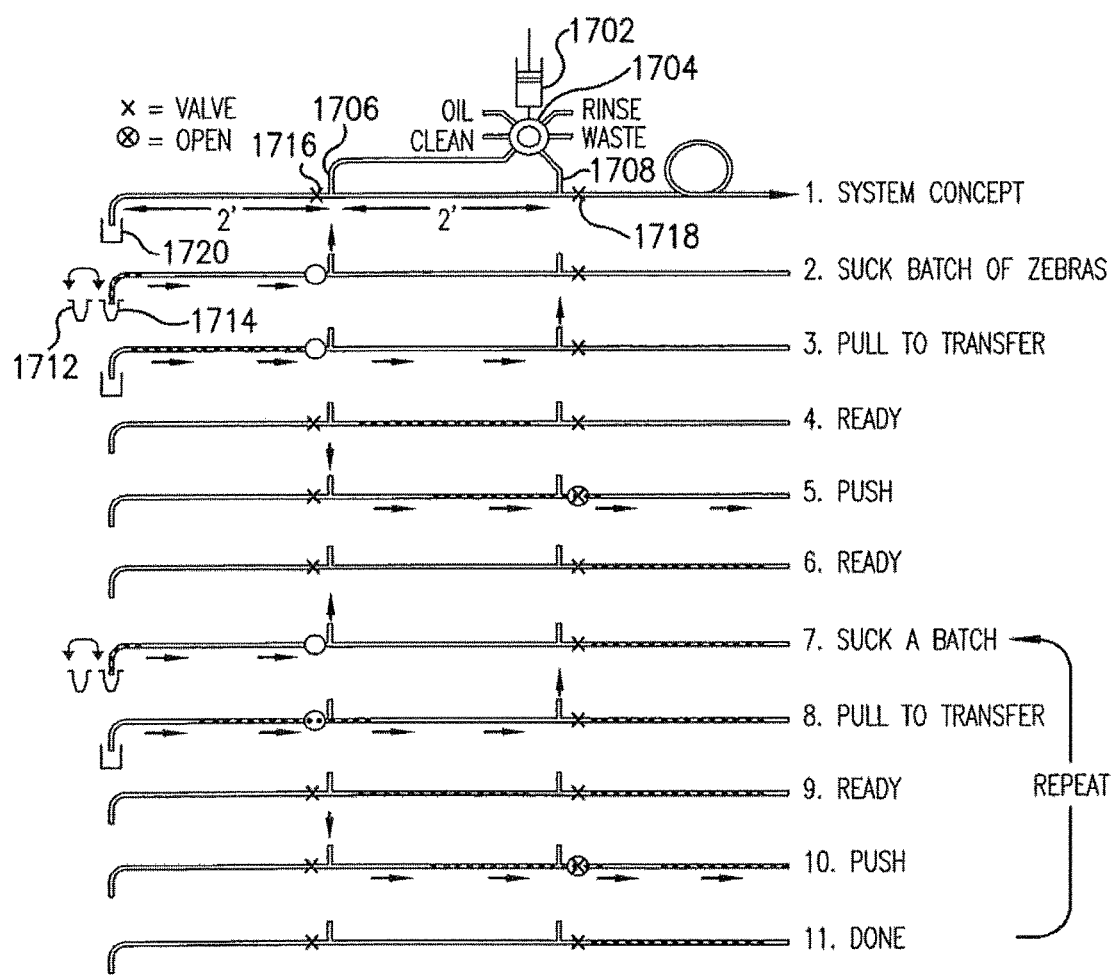
Figure 18:
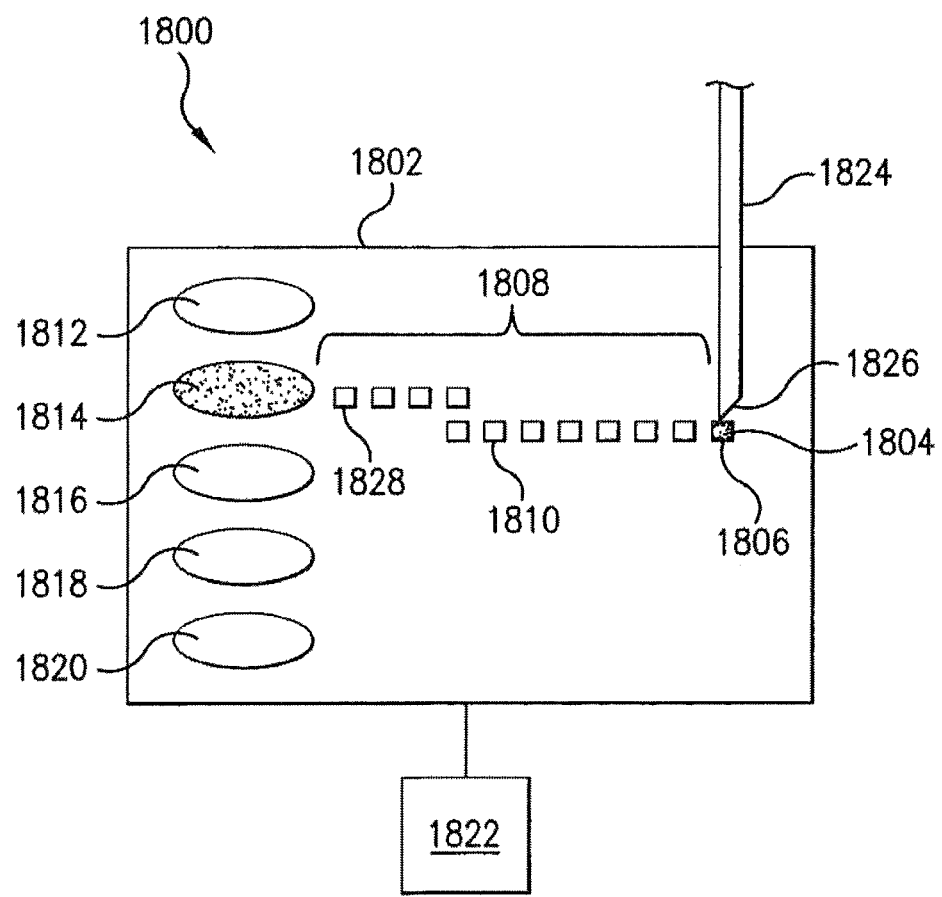
Figure 19:
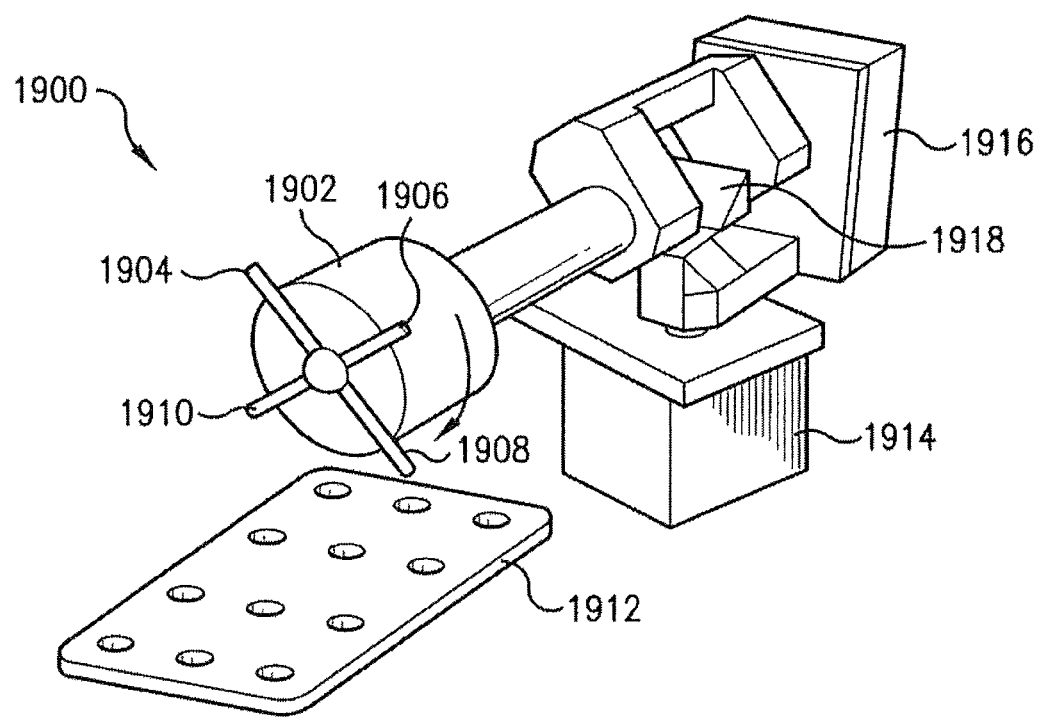
Figure 20:
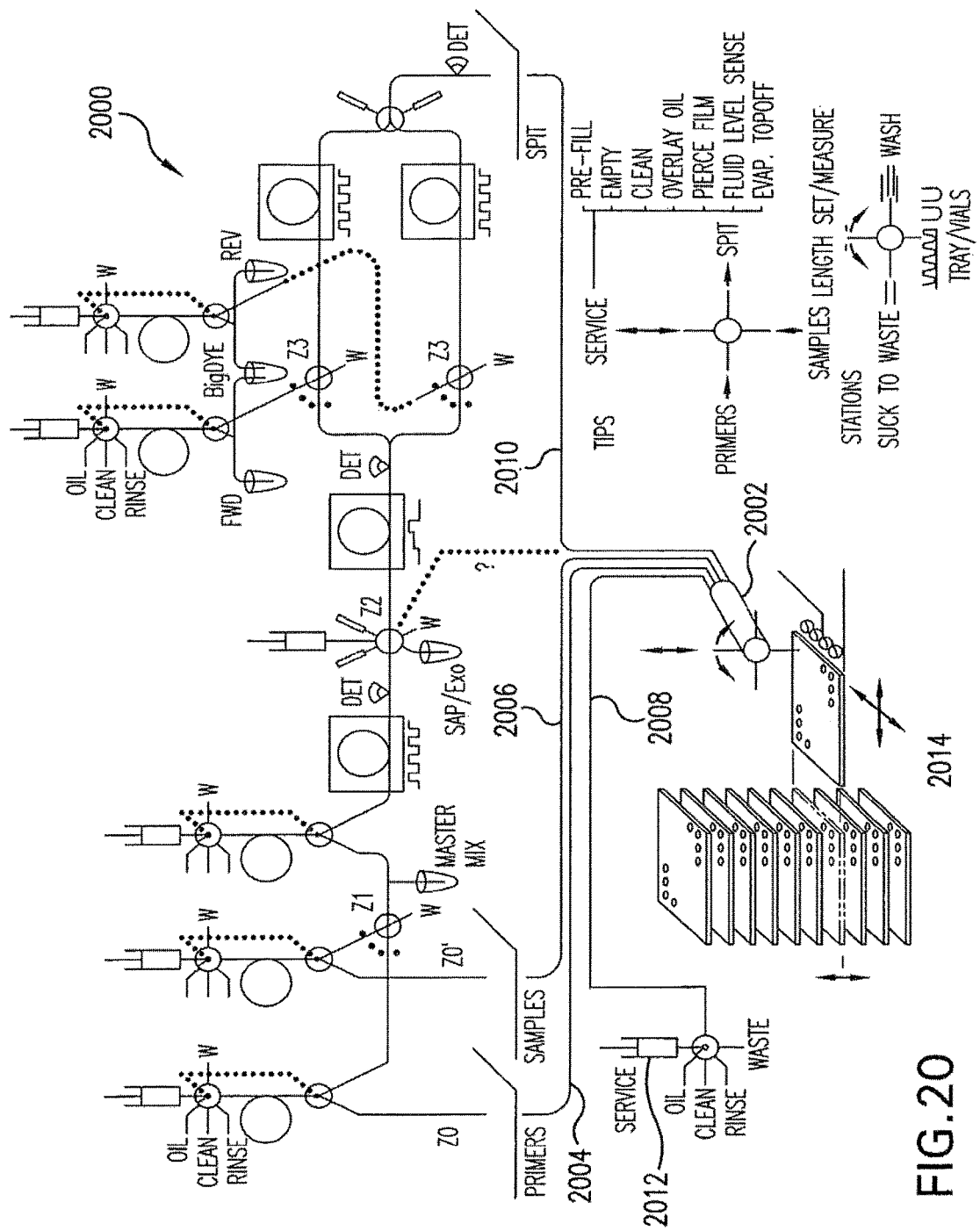
Figure 22A:
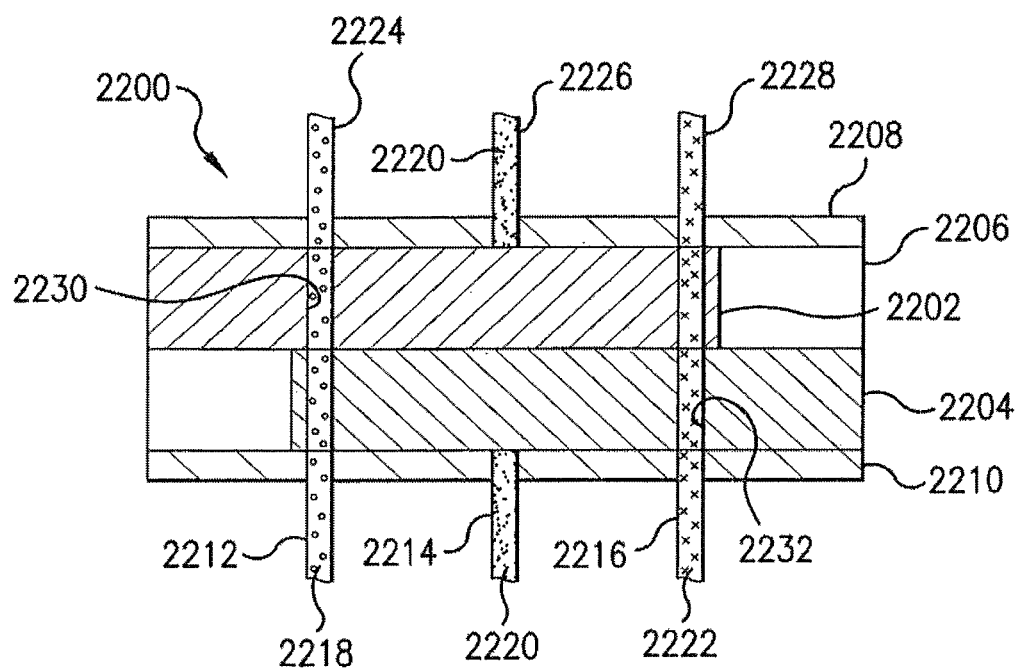
Figure 22B:
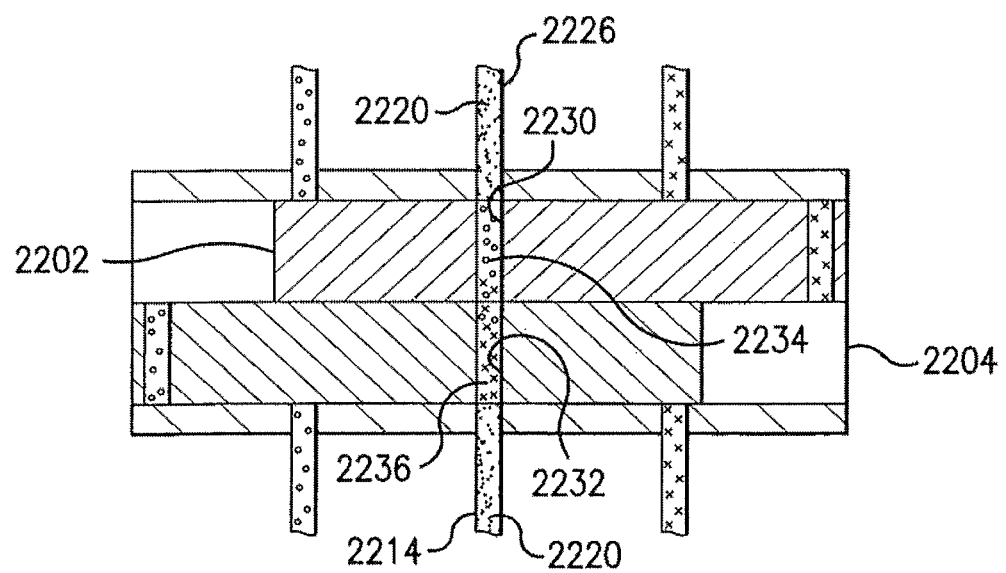
Figure 29:
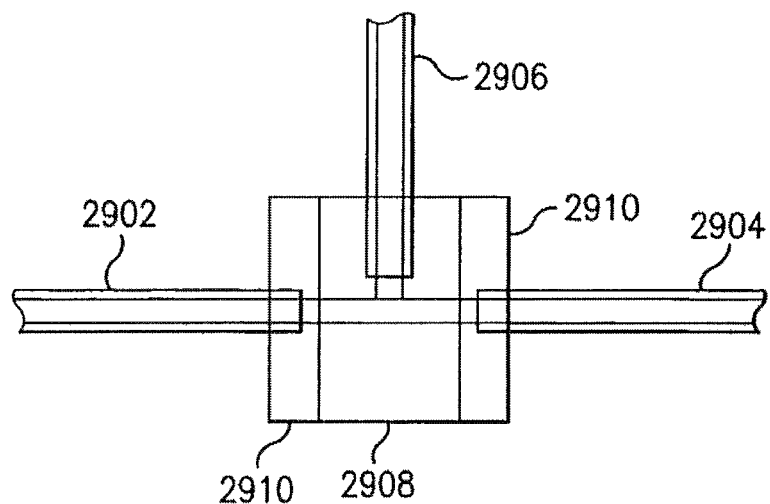
Figure 30:
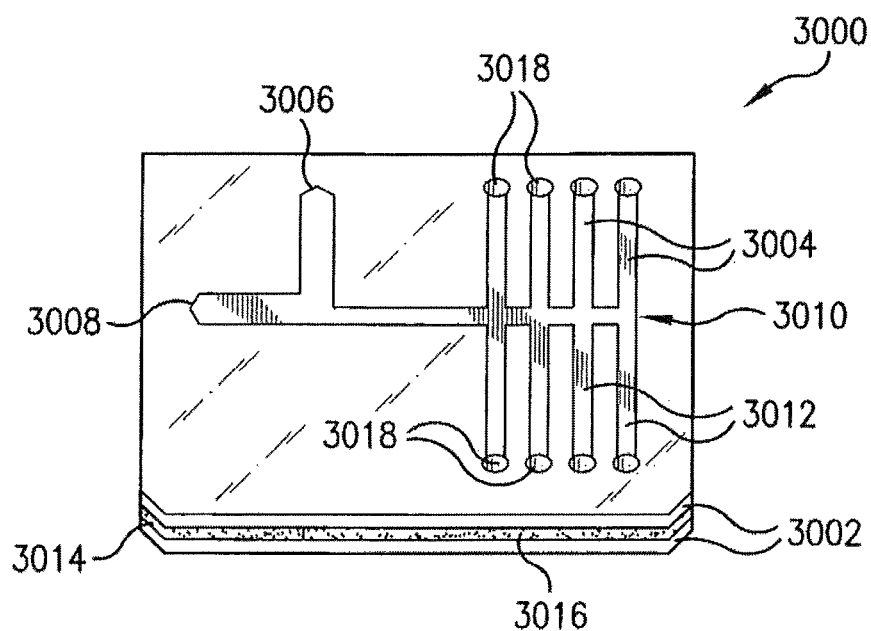
Figure 31:
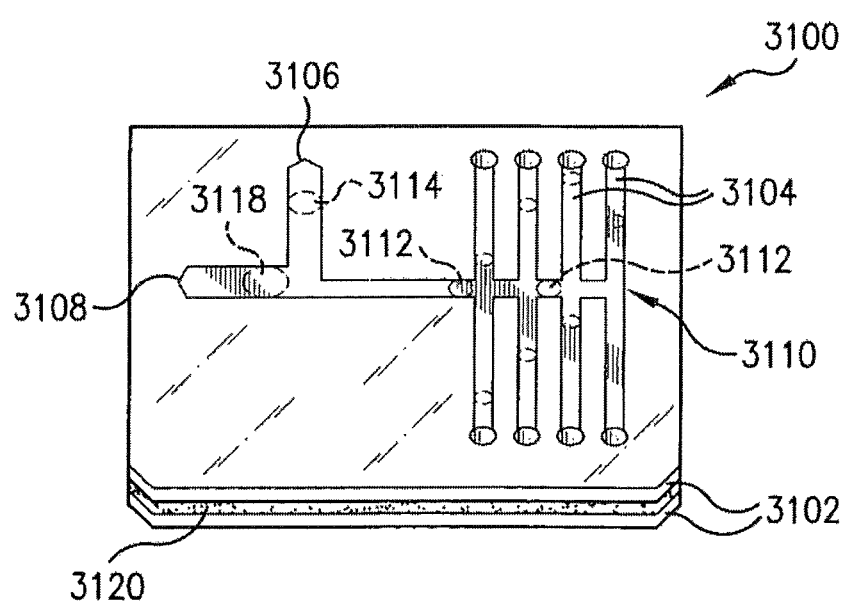
Figure 32:
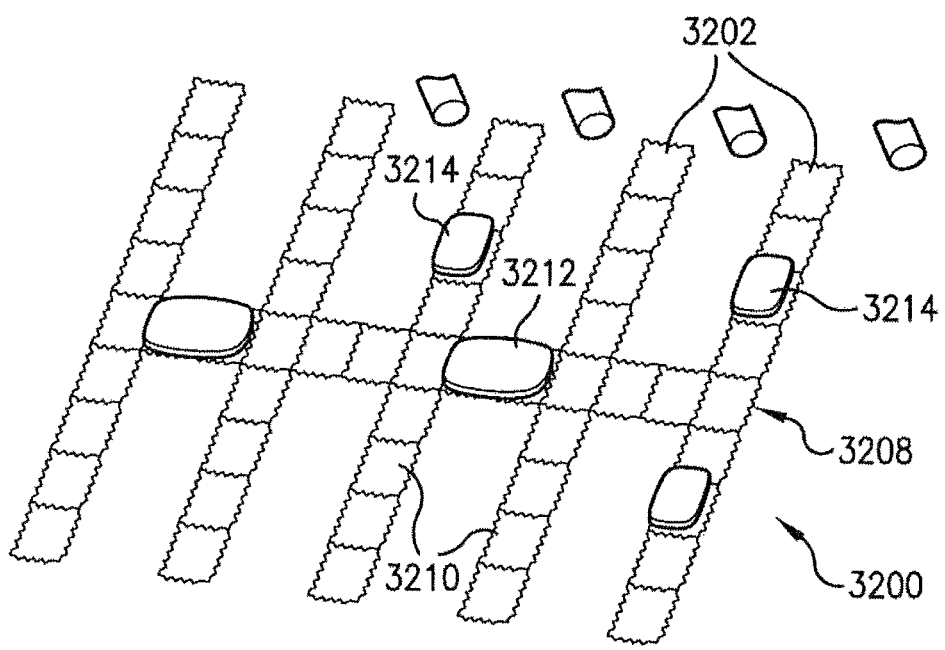
Figure 33:
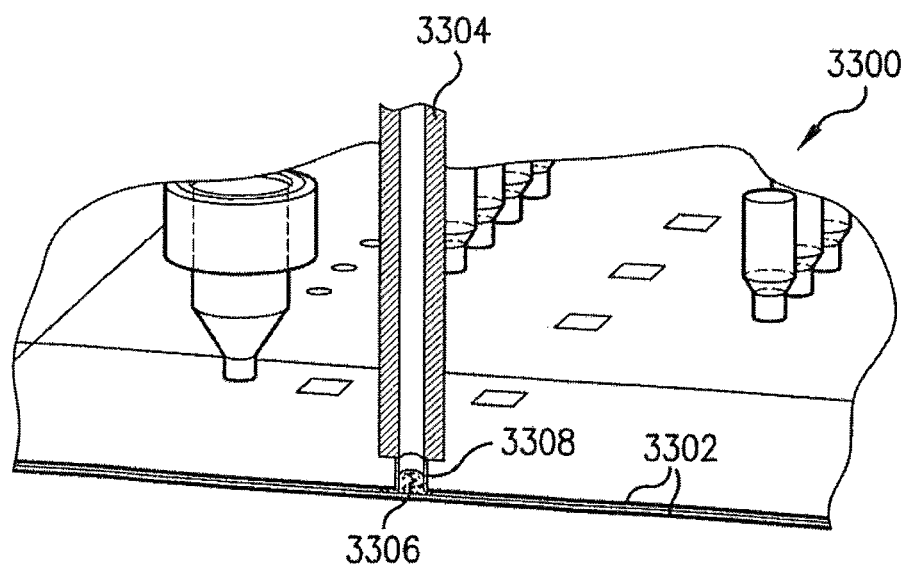
Figure 34:
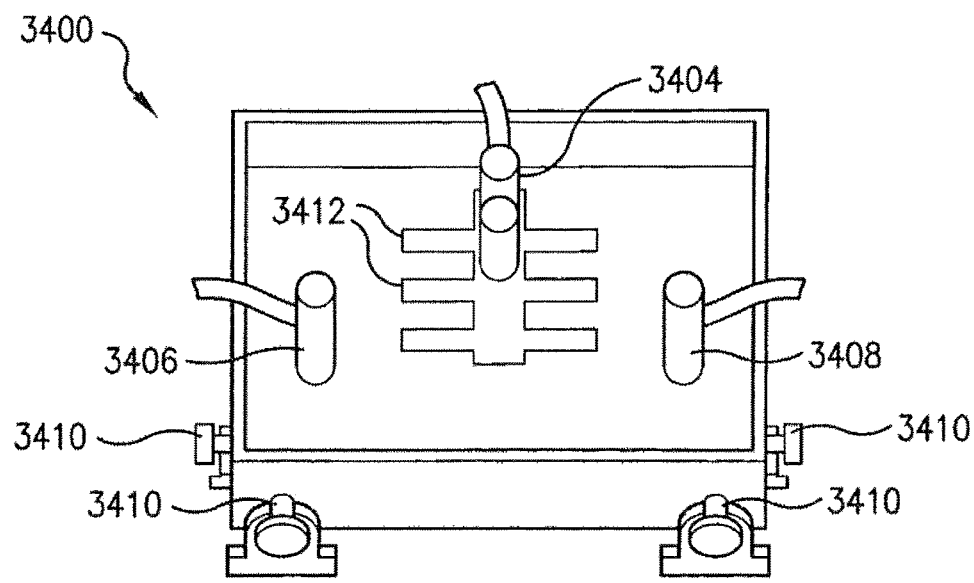
Figure 35:
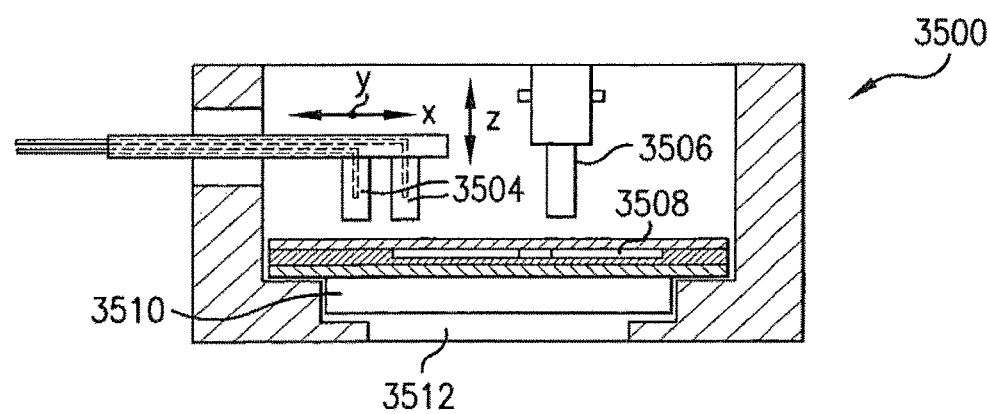
Figure 36:
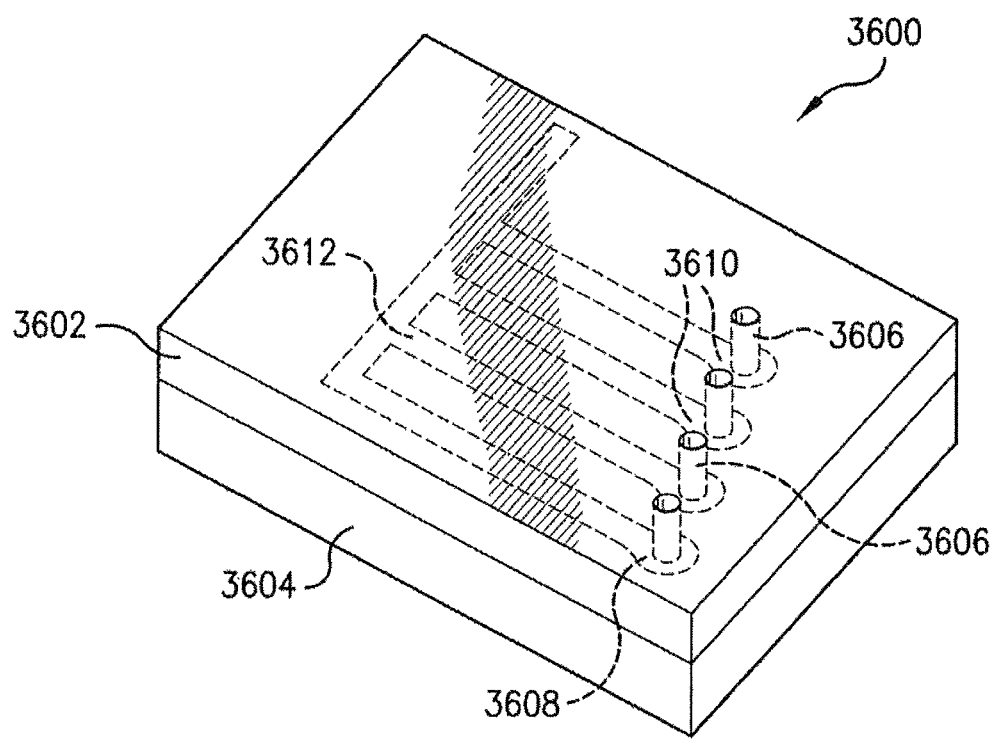
Figure 37:
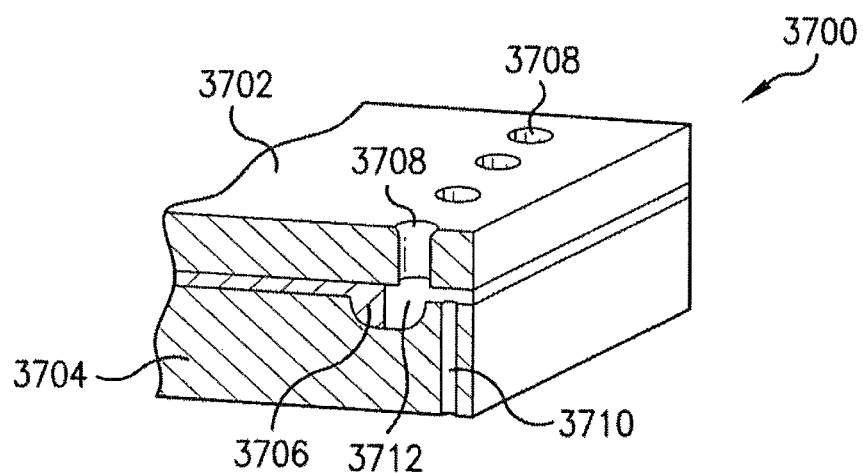
Figure 38:
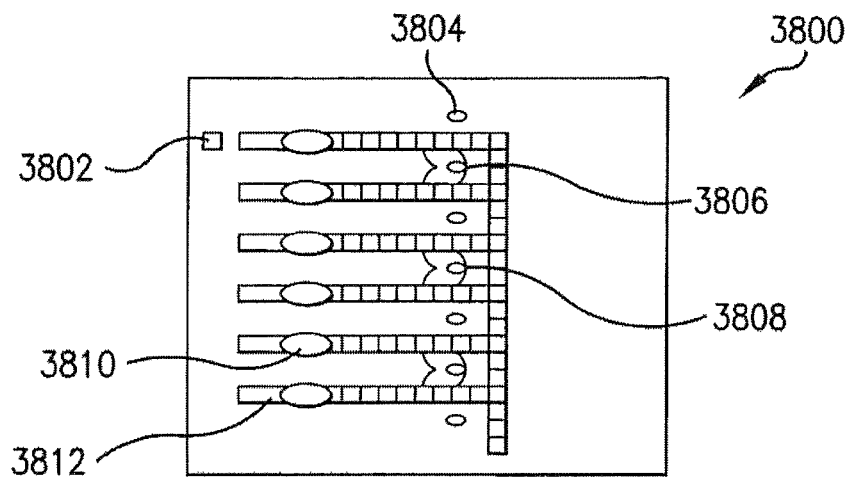
Figure 39:
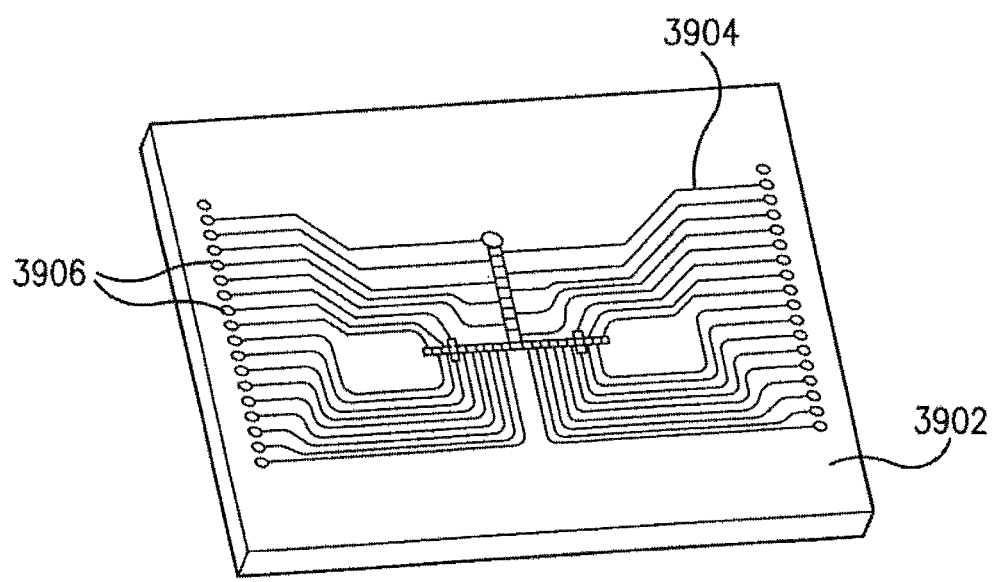
Figure 42:
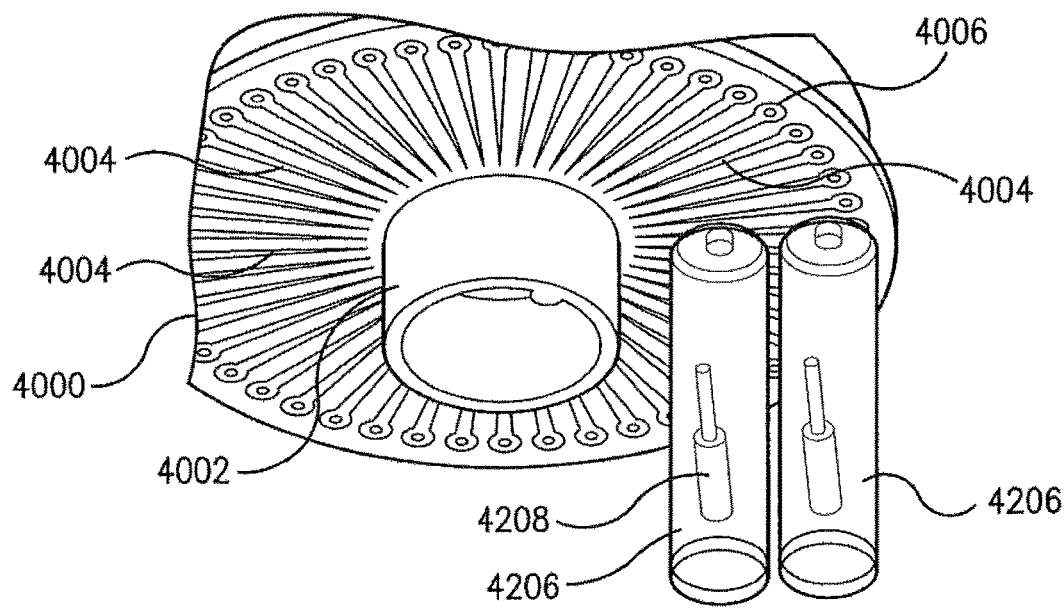
Figure 43:
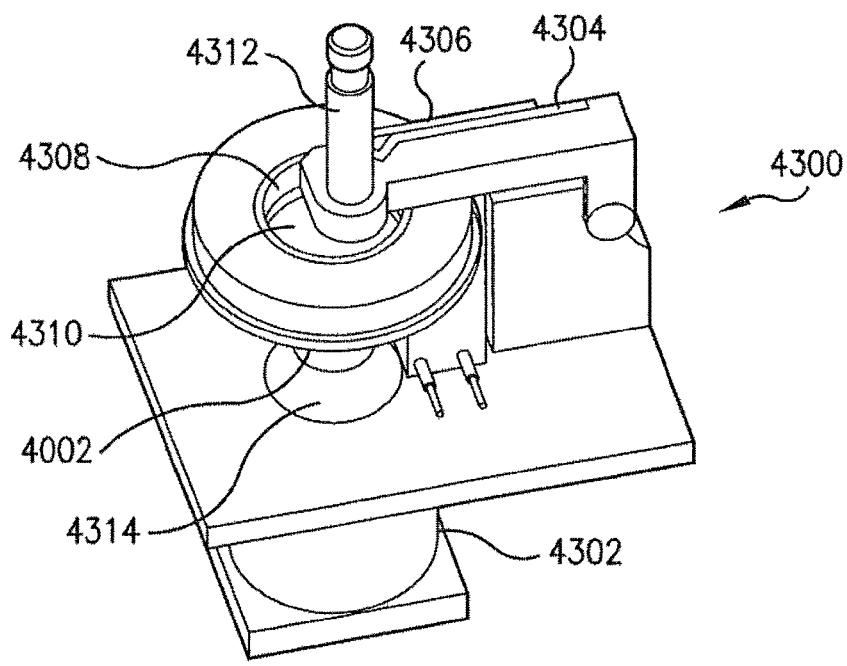
Figure 44:
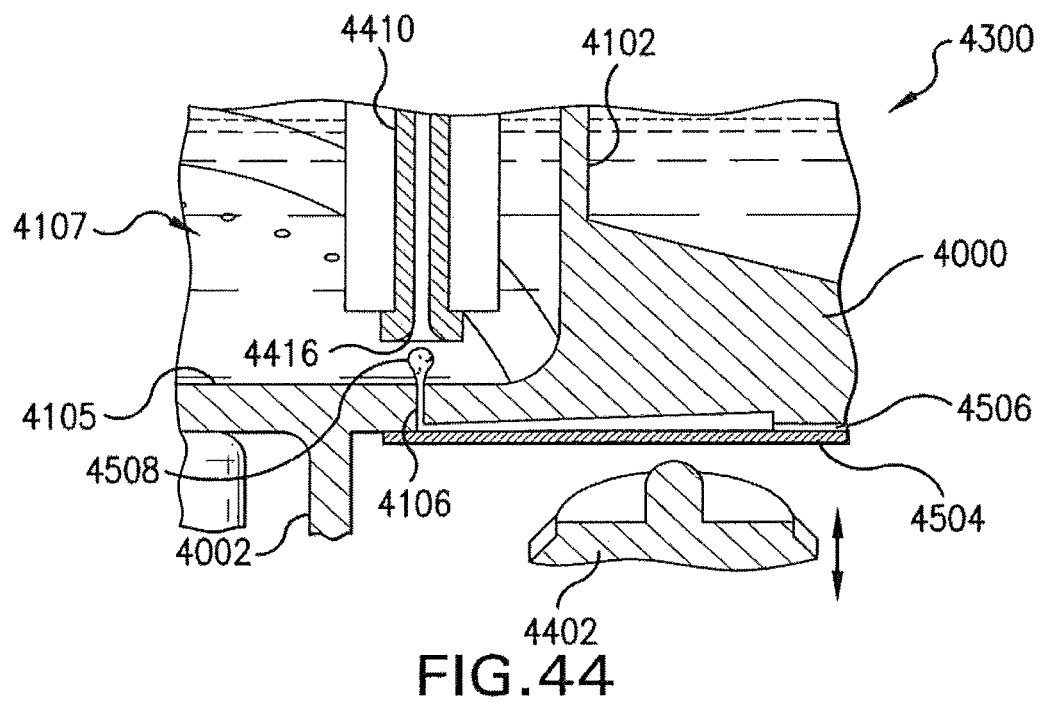
Figure 45:
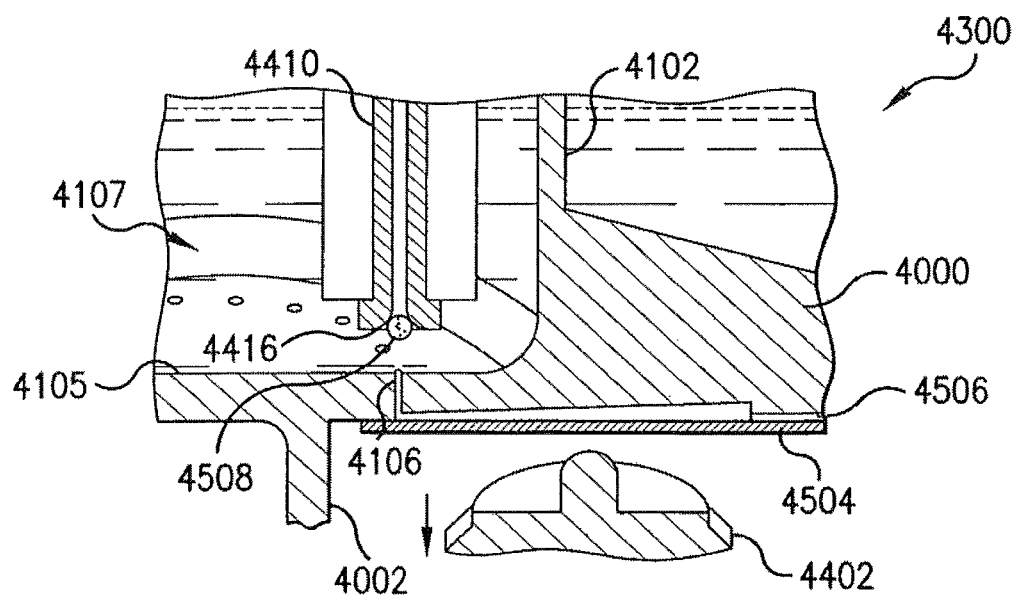
Figure 46:
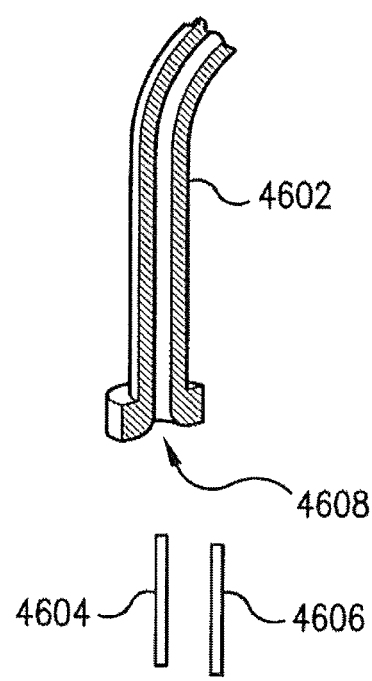
Figure 48:
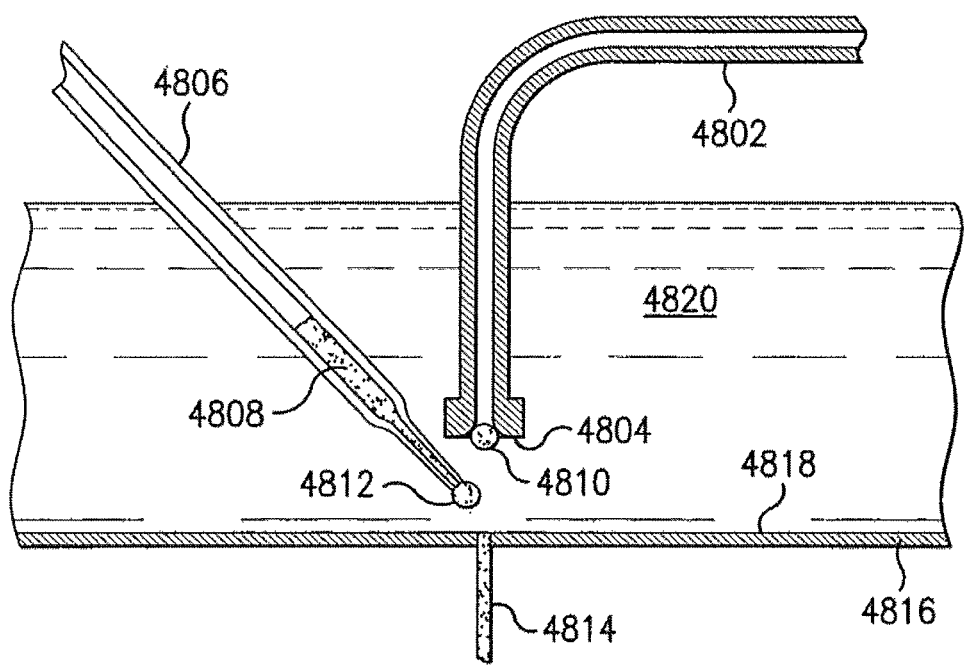
Figure 49:
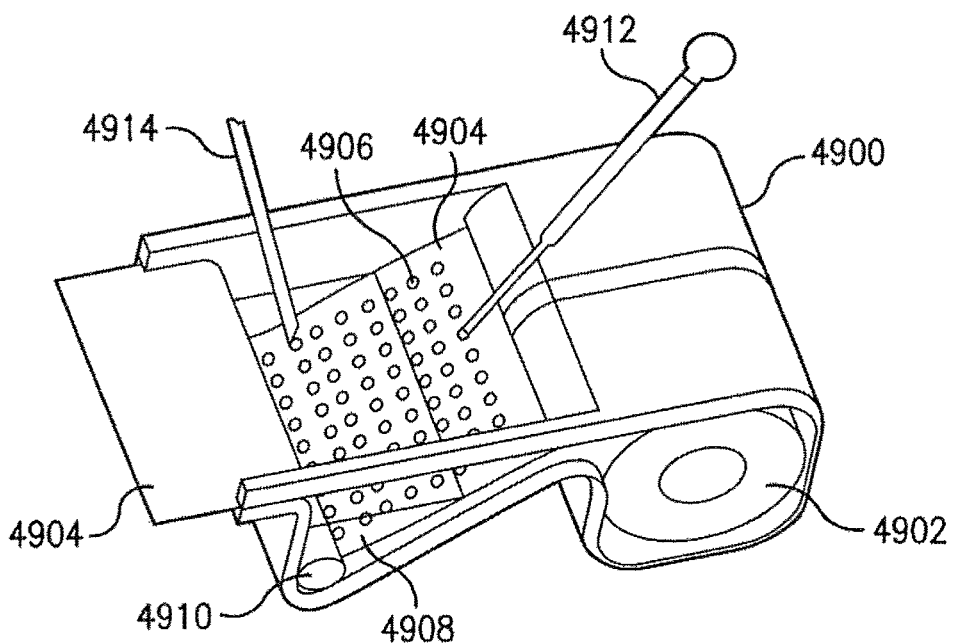
Figure 50:
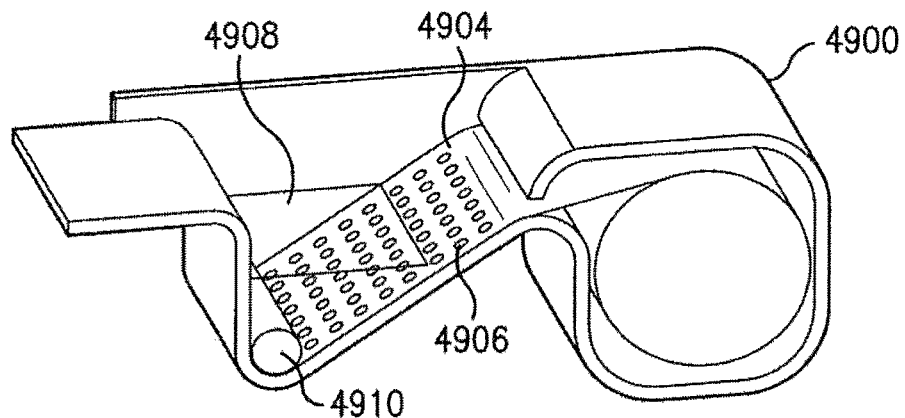
Figure 51:
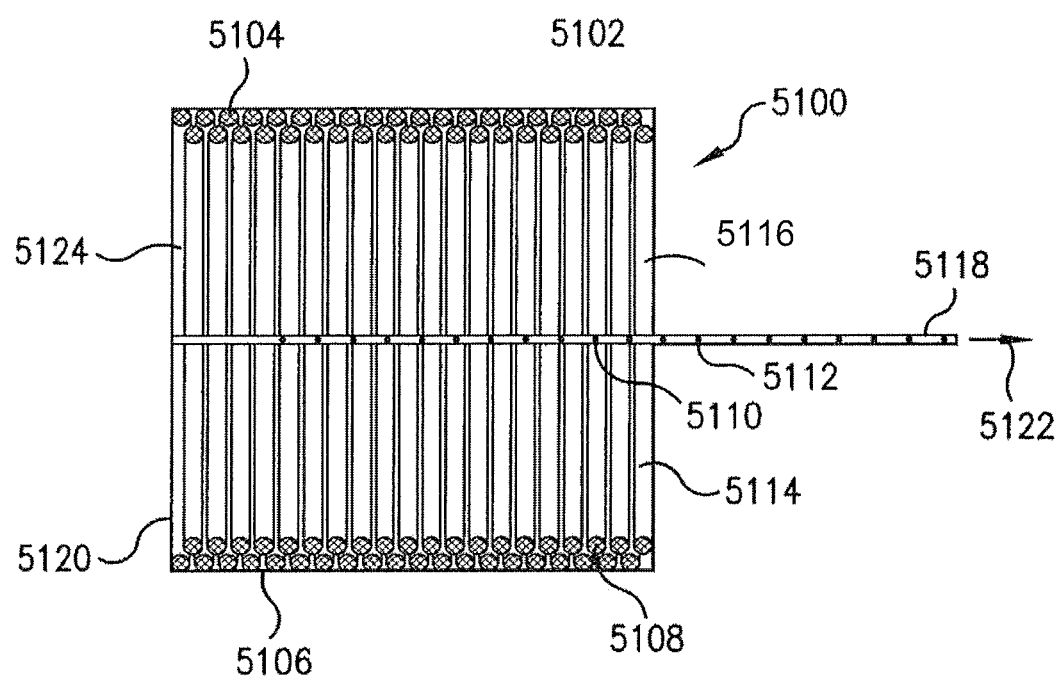
Figure 52:
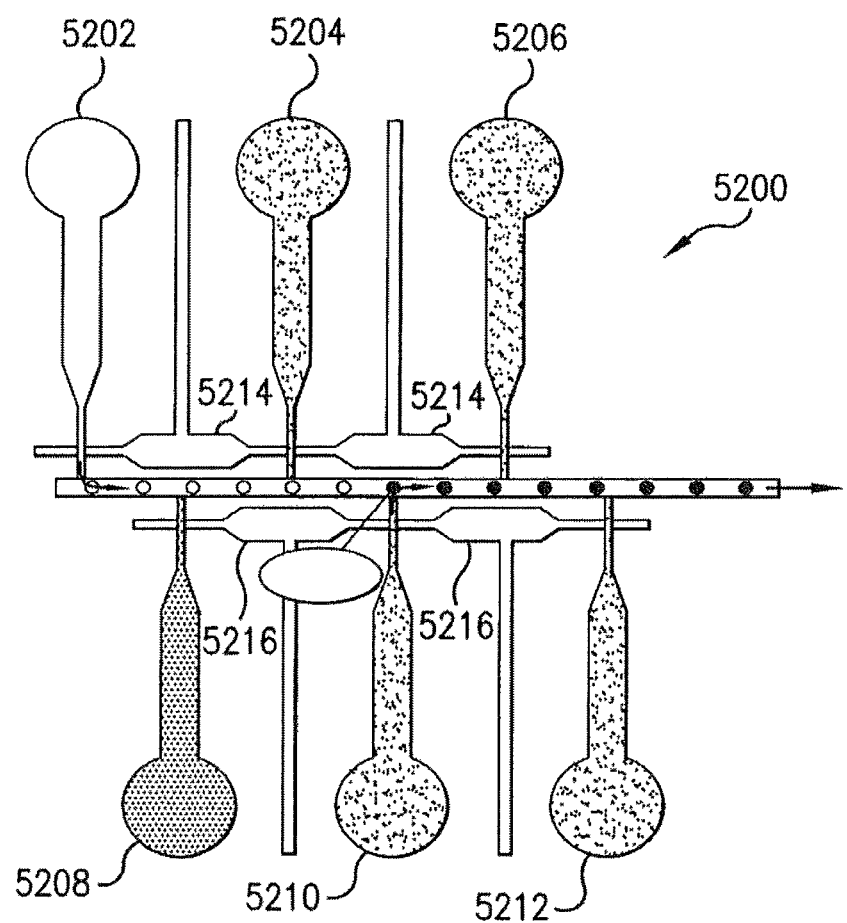
Figure 55:
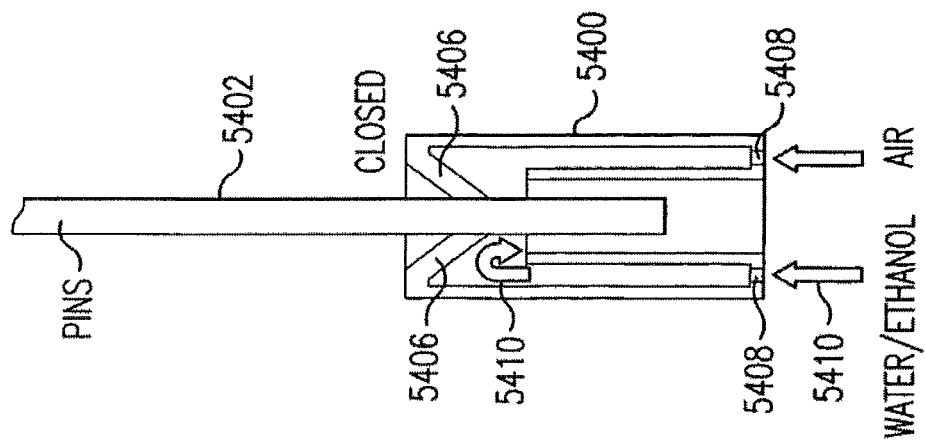
Figure 54:
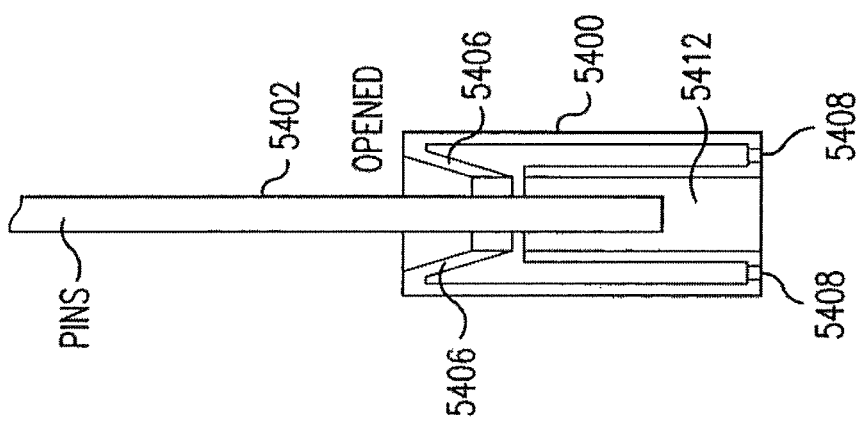
Figure 53:
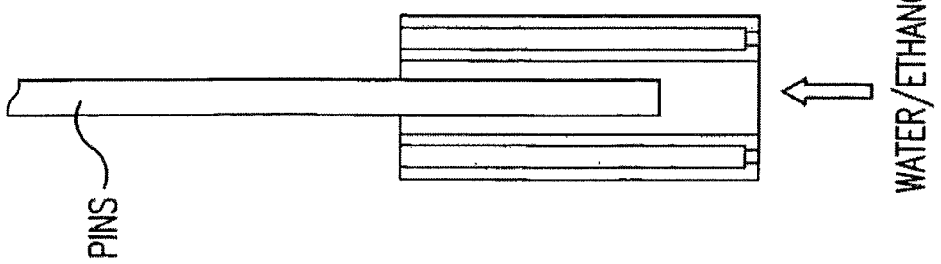

FIG. 7 illustrates a manifold system according to various embodiments of the present teachings, wherein the manifold comprises three side openings connected to tubes containing different liquids to be delivered to an immiscible-fluid-discrete-volume-forming tube, the left end of the manifold is connected to an oil supply unit, and the right end of the manifold is connected to an immiscible-fluid-discrete-volume recovery unit;

FIG. 8 illustrates a schematic of aqueous discrete-volume generation by sipping liquid from tubes containing alternate aqueous liquid and oil, wherein sipping is produced by a syringe connected to the tube in which the aqueous discrete-volumes are to be generated;

FIGS. 9A and 9B illustrate a schematic of a thin oil layer in the tubes (FIG. 9A) and a continuous oil overlay (FIG. 9B), wherein FIG. 9B is shown in partial cross-section;

FIGS. 10A-10D illustrate various schematics of aqueous and oil liquids in wells, used to generate aqueous discrete-volumes by sipping, wherein FIGS. 10C and 10D are shown in partial cross-section;

FIG. 11 illustrates a trough made of polytetrafluoroethylene and also demonstrates positioning the trough in a sample preparation system, according to various embodiments;

FIG. 12A is a top view of a system according to various embodiments comprising an artesian well for rinsing the intake tip of a aqueous discrete-volume-forming conduit and a intake tip positioning unit;

FIG. 12B is an enlarged cross-sectional view of the artesian well rinse fountain shown in FIG. 12A;

FIG. 13 is an enlarged view of an intake tip of a aqueous discrete-volume-forming conduit according to various embodiments;

FIG. 14 is a side view of a system according to various embodiments comprising a rocker arm, two alternatively-extendible intake tips, and a movable stage retaining a multi-well sample tray;

FIG. 15 is a schematic view of a system comprising a temporary holding conduit for temporarily holding a set of aqueous discrete-volumes of a first fluid spaced-apart from one another by an immiscible spacing fluid and ready to be pushed into a processing conduit;

FIG. 16 illustrates a series successive valve orientation and flow direction schemes along a multi-step process for generating sets of spaced-apart aqueous discrete-volumes of a first fluid in an immiscible spacing fluid, according to various embodiments;

FIG. 17 illustrates a series successive valve orientation and flow direction schemes along a multi-step process for generating sets of spaced-apart aqueous discrete-volumes of a first fluid in an immiscible spacing fluid, according to various embodiments;

FIG. 18 is a perspective view of a system for moving discrete volumes of fluid along electro-wetting pathways to an intake location adjacent an intake tip of a aqueous discrete-volume-forming conduit;

FIG. 19 is a perspective view of a multi-conduit fluid manipulator according to various embodiments;

FIG. 20 is a schematic diagram of a system for generating, processing, detecting, and out-putting a plurality of aqueous discrete-volumes of a first fluid composition spaced-apart from one another by an immiscible spacing fluid;

FIGS. 21A-21F illustrate successive steps in a process for generating aqueous discrete-volumes of a first fluid spaced-apart from one another by a spacing fluid and using a system comprising a through-hole slider in a housing;

FIGS. 22A and 22B illustrate successive steps in a process for generating aqueous discrete-volumes of a first and second fluid mixture spaced-apart from one another by a spacing fluid, and using a system comprising top and bottom through-hole sliders in a housing;

FIGS. 23-28 are top views of various stator and rotor valve systems according to various embodiments;

FIG. 29 is a top view of a slider-in-housing valve that can form or interrupt a three-way fluid communication, according to various embodiments;

FIGS. 30 and 31 are perspective views of an electro-wetting device configured to move a first fluid into position for being drawn into an immiscible-fluid-discrete-volume-forming-conduit, according to various embodiments;

FIG. 32 is a perspective close-up view of various electrode pathways in an electro-wetting device configured to move a first fluid into position for being drawn into an immiscible-fluid-discrete-volume-forming-conduit, according to various embodiments;

FIG. 33 is a perspective view of a system comprising an electro-wetting device and an immiscible-fluid-discrete-volume-forming-conduit intake tip disposed for drawing in a drop of fluid that has been manipulated by the electro-wetting device;

FIGS. 34 and 35 are a top perspective view and side view, respectively, of an electro-wetting system for controlling an electro-wetting device according to various embodiments;

FIGS. 36 and 37 are perspective views of a through-hole electro-wetting device according to various embodiments;

FIG. 38 is a top view of an electro-wetting device configured to move a first fluid into position for being drawn into an immiscible-fluid-discrete-volume-forming-conduit, according to various embodiments;

FIG. 39 is a perspective view of an electrode configuration of an electro-wetting device according to various embodiments and showing electro-wetting contact pads;

FIGS. 40-43 are perspective views of an aqueous discrete-volume-forming carousel and a system for using the carousel to generate aqueous discrete-volumes of a first fluid spaced-apart from one another by a spacing fluid, according to various embodiments;

FIGS. 44-45 are cross-sectional views of the system shown in FIGS. 42 and 43;

FIG. 46 is a simplified schematic drawing showing how the system and carousel in FIGS. 40-45 generate spaced-apart aqueous discrete-volumes;

FIGS. 47A-47E are schematic drawings of sequential steps for generating aqueous discrete-volumes and for merging two discrete volumes together before forming the two volumes into a single aqueous discrete-volume, and which steps can be used with the carousel and system shown in FIGS. 40-45;

FIG. 48 is a side view of a system similar to that described in connection with FIGS. 40-45, for generating aqueous discrete-volumes and merging two fluids together to generate a large aqueous discrete-volume, according to various embodiments;

FIGS. 49 and 50 are perspective views of a cartridge system comprising a roll of film comprising dried-down reagent spots that can be reconstituted, submerged in an immiscible spacing fluid while clinging to the film, and drawn into an intake tip of an aqueous discrete-volume-forming conduit;

FIG. 51 is a top view of an assay plate device comprising an immiscible-fluid-discrete-volume-forming conduit, supplies of assay materials, and a magnetohydrodynamic pump system for moving immiscible-fluid-discrete-volumes into the conduit, according to various embodiments;

FIG. 52 is a top view of an assay plate device comprising an immiscible-fluid-discrete-volume-forming conduit, supplies of assay materials, and a magnetohydrodynamic pump system for moving immiscible-fluid-discrete-volumes into the conduit, according to other various embodiments;

FIG. 53 is a cross-sectional side view of an intake tip rinse device showing an intake tip inserted therein and supplies of air and rinse fluid, according to various embodiments; and FIGS. 54 and 55 are cross-sectional side views of an intake tip rinse device showing an intake tip inserted therein and in an open state (FIG. 54) and in a closed state (FIG. 55), according to various embodiments.

DESCRIPTION OF VARIOUS EMBODIMENTS

It is to be understood that the following descriptions are exemplary and explanatory only. The accompanying drawings are incorporated in and constitute a part of this application and illustrate several exemplary embodiments with the description. Reference will now be made to various embodiments, examples of which are illustrated in the accompanying drawings. Wherever possible, the same reference numbers are used in the drawings and the description to refer to the same or like parts.

Throughout the application, descriptions of various embodiments use "comprising" language, however, it will be understood by one of skill in the art, that in some specific instances, an embodiment can alternatively be described using the language "consisting essentially of" or "consisting of".

For purposes of better understanding the present teachings and in no way limiting the scope of the teachings, it will be clear to one of skill in the art that the use of the singular includes the plural unless specifically stated otherwise. Therefore, the terms "a," "an" and "at least one" are used interchangeably in this application.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. In some instances, "about" can be understood to mean a given value ±5%. Therefore, for example, about 100 nl, could mean 95-105 nl. At the very least, each numerical parameter should at least be construed in light of the number of reported significant digits and by applying ordinary rounding techniques.

The term "coaxially arranged" should be understood to mean at least two conduits are arranged one inside the other, for example, such that they have a common axis. An example of a coaxial arrangement can comprise a smaller diameter tube within a larger diameter tube.

Reference to "nucleotide" should be understood to mean a phosphate ester of a nucleotide, as a monomer unit or within a nucleic acid. Nucleotides are sometimes denoted as "NTP", or "dNTP" and "ddNTP" to particularly point out the structural features of the ribose sugar. "Nucleotide 5'-triphosphate" can refer to a nucleotide with a triphosphate ester group at the 5' position. The triphosphate ester group may include sulfur substitutions for the various oxygens, for example, α-thio-nucleotide 5'-triphosphates. Nucleotides can comprise a moiety of substitutes, for example, see, U.S. Pat. No. 6,525,183 B2 to Vinayak et al., incorporated herein by reference in its entirety.

The terms "polynucleotide" or "oligonucleotide" or "nucleic acid" can be used interchangeably and include single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5'terminus, 3'terminus, a nucleobase, an internucleotide linkage, a sugar, amino, sulfide, hydroxyl, or carboxyl. See, for example, U.S. Pat. No. 6,316,610 B2 to Lee et al. which is incorporated herein by reference. Similarly, other modifications can be made at the indicated sites as deemed appropriate.

The term "reagent," should be understood to mean any reaction component that in any way affects how a desired reaction can proceed or be analyzed. The reagent can comprise a reactive or non-reactive component. It is not necessary for the reagent to participate in the reaction. The reagent can be a recoverable component comprising for example, a solvent and/or a catalyst. The reagent can comprise a promoter, accelerant, or retardant that is not necessary for a reaction but affects the reaction, for example, affects the rate of the reaction. A reagent can comprise, for example, one member of a binding pair, a buffer, or a DNA that hybridizes to another DNA. The term "reagent" is used synonymously with the term "reaction component."

Methods, apparatuses and systems described herein can use fluids immiscible in each other. Fluids can be said to be immiscible in each other when they can be maintained as separate fluid phases under conditions being used. Immiscible fluids can also be said to be incapable of mixing with each other or attaining a solution with each other. An aqueous liquid and a non-aqueous liquid such as oil can be said to be immiscible with each other. Throughout the specification, reference is made to aqueous slugs. This is merely exemplary and does not necessarily preclude the use or manufacture of non-aqueous liquid slugs in combination with an immiscible liquid.

While oil and aqueous liquids are immiscible in each other, such a combination does not necessarily form aqueous immiscible-fluid-discrete-volumes in the oil when the two liquids are mixed or placed together. For example, oil may form the disperse phase in a continuous aqueous liquid in a larger volume, as it does in certain salad dressings. For another example, oil and aqueous liquids may merely form aqueous droplets or microdroplets in a larger volume of oil, but not necessarily aqueous immiscible-fluid-discrete-volumes.

Aqueous solutions and oil from separate sources can be combined to form a continuous flowing liquid stream comprising aqueous immiscible-fluid-discrete-volumes separated from one another by the oil. Because the aqueous immiscible-fluid-discrete-volumes entirely or almost entirely fill the cross-sectional area of the conduit or tube in which they are formed, the resulting stream of aqueous immiscible-fluid-discrete-volumes in oil can exhibit a banded appearance. According to various embodiments, such a pattern can be exhibited by combining any two immiscible fluids with one another. The pattern can be formed throughout the length of the conduit. In various embodiments, a first aqueous immiscible-fluid-discrete-volume can contain different reagents than a second aqueous immiscible-fluid-discrete-volume. In other words, not all aqueous immiscible-fluid-discrete-volumes throughout the conduit need to contain the same reagents.

An aqueous immiscible-fluid-discrete-volume can be spaced apart from an adjacent aqueous immiscible-fluid-discrete-volume by the oil. In various embodiments, liquids other than oil can act as a spacing fluid, provided that the spacing fluid and aqueous fluid are immiscible with respect to each other and provided that they can form individual aqueous immiscible-fluid-discrete-volumes spaced apart from one another by the spacing fluid. In various embodiments, gas can be used as a spacing fluid.

According to various embodiments, methods are provided that refer to processes or actions involved in sample preparation and analysis. It will be understood that in various embodiments a method can be performed in the order of processes as presented, however, in related embodiments, the order can be altered as deemed appropriate by one of skill in the art in order to accomplish a desired objective.

According to various embodiments, an apparatus is provided that can be used as a front-end sample preparation device for high-throughput sequencing, or other applications requiring preparation and/or processing of a plurality of small samples. The sample liquid that can become an immiscible-fluid-discrete-volume can comprise, for example, nucleic acids, proteins, polypeptides, carbohydrates, or the like. The apparatus can be part of an integrated system and/or be adapted to function with other pieces of equipment adapted for further sample processing of samples, for example, an ABI 310, ABI 3130, ABI 3130xl, ABI 3700, ABI 3730, or ABI 3730xl capillary electrophoretic analyzer (available from Applied Biosystems, Foster City, Calif.) that can be used for sequencing. In some embodiments, the apparatus can be part of an integrated system and/or be adapted to function with other pieces of equipment adapted for further sample processing of samples, for example, a PCR detector. Exemplary detectors that can be used include real-time sequence detection systems and real-time PCR detectors, for example, the ABI 7900, available from Applied Biosystems, Foster City, Calif.

The apparatus, system and/or methods described herein can also be used in conjunction with downstream processing of immiscible-fluid-discrete-volumes in conduits as described, for example, in FIGS. 10 and 11 of U.S. Provisional Patent Application No. 60/710,167 entitled "Sample Preparation for Sequencing" to Lee et al., filed Aug. 22, 2005, or U.S. Provisional Patent Application No. 60/731,133 entitled "Method and System for Spot Loading a Sample" to Schroeder et al., filed Oct. 28, 2005 which applications are incorporated herein in their entireties by reference. If there is any discrepancy between the description of a slug in an immiscible fluid in the above provisional applications and this one, this application is deemed to be correct.

Figure 1A:
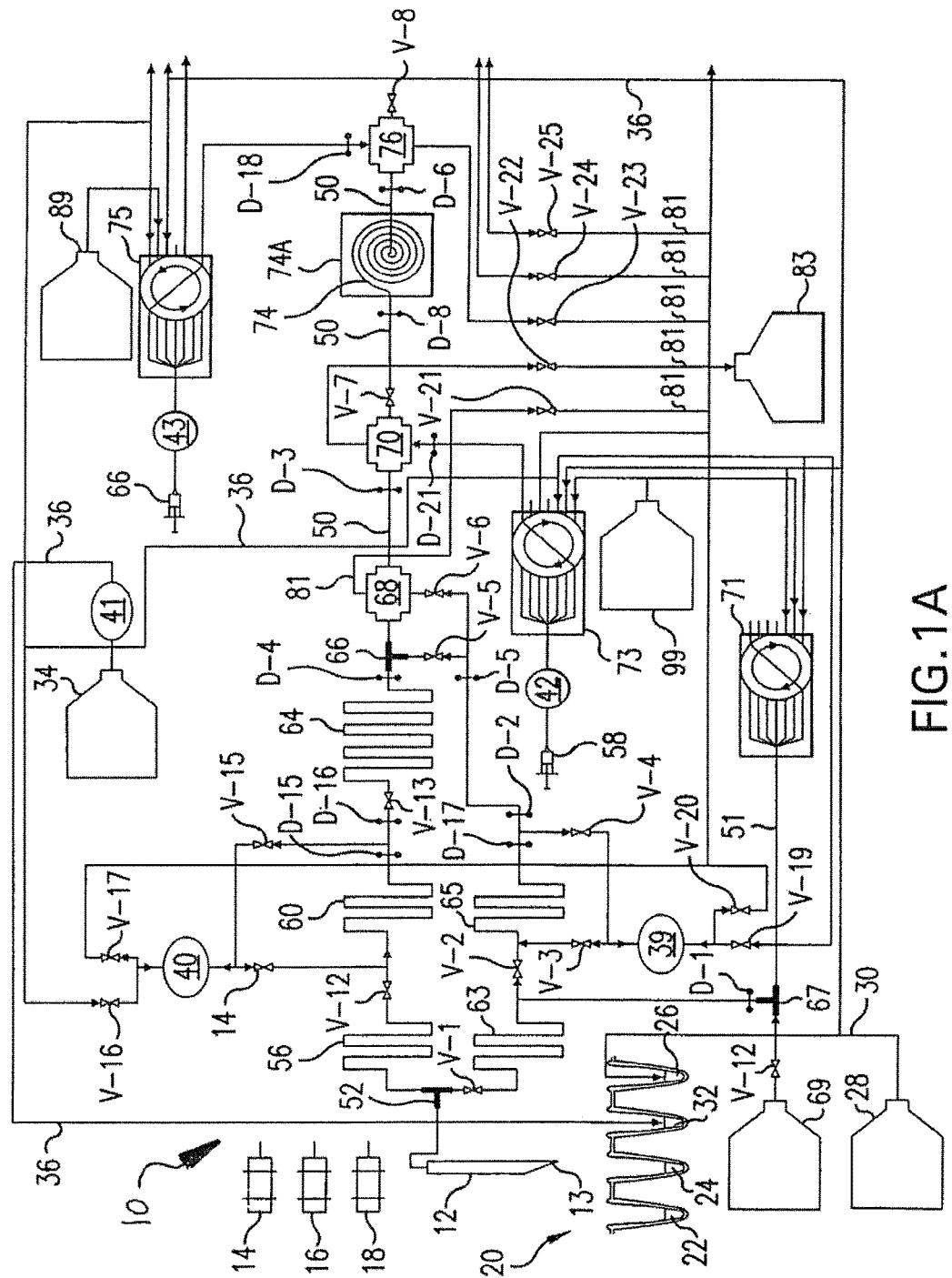
FIGS. 1A and 1B are the left-side and right-side, respectively, of a schematic diagram depicting a system according to various embodiments of the present teachings and configured to generate immiscible-fluid-discrete-volumes of a first fluid spaced apart from one another by a spacing fluid, to process the immiscible-fluid-discrete-volumes, and to output the immiscible-fluid-discrete-volumes.
Figure 1B:
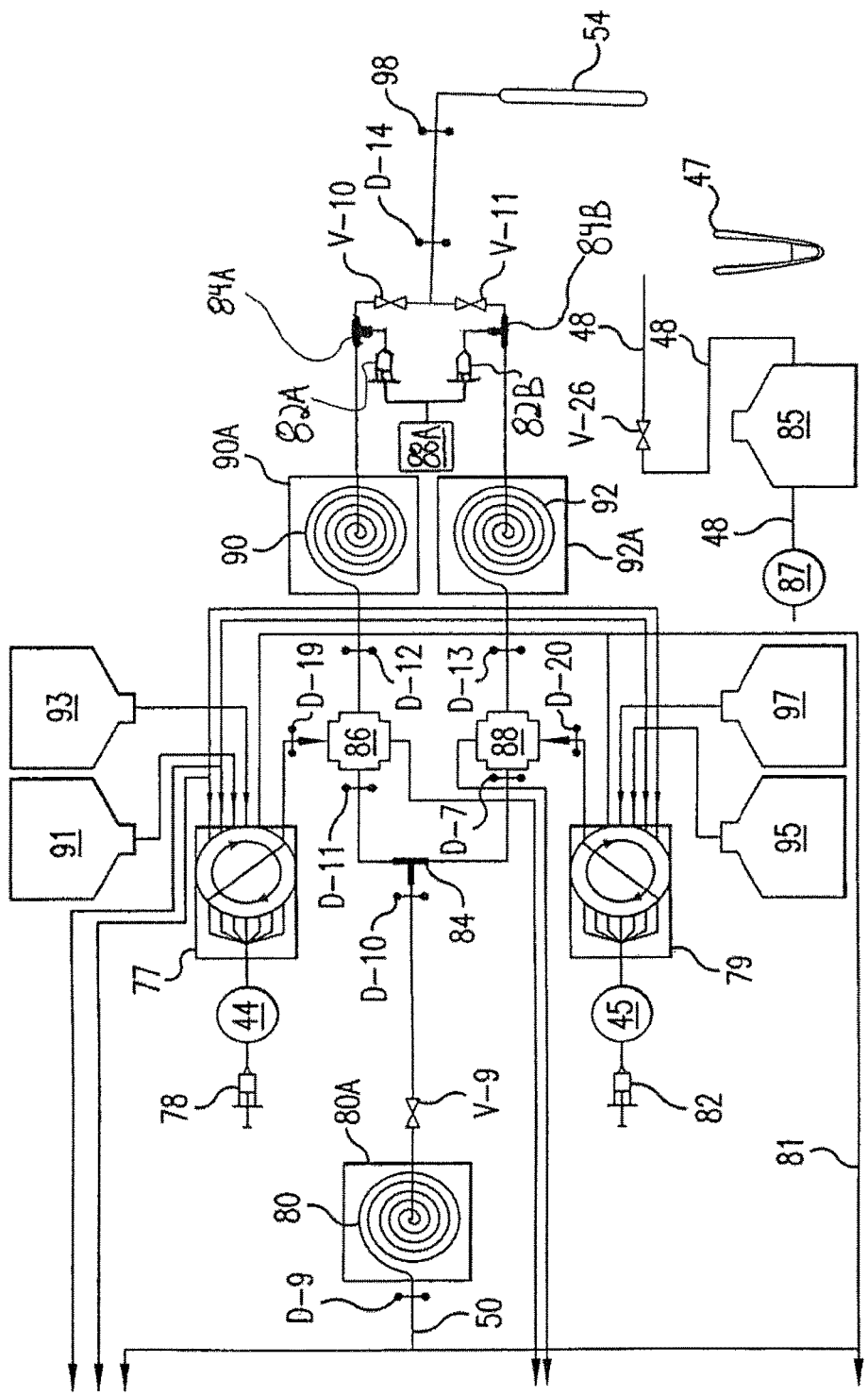

FIGS. 1A and 1B are the left-side and right-side, respectively, of a schematic diagram detailing an example of a fluid processing system 10 for processing fluid immiscible-fluid-discrete-volumes. The six conduits on the right-hand side of FIG. 1A and terminating in arrow heads pointing to the right are respectively continued as the six conduits shown on the left-hand side of FIG. 1B and terminating in arrow heads pointing to the left, such that the top conduit of each respective six depicted are continuations of each other, and so on going down the figures.

Generally, system 10 can be configured to perform different types of assays on fluids introduced thereinto. The amounts and types of fluids introduced into system 10 can be varied depending on a particular assay to be performed. Exemplary assays can include, for example, de novo nucleic acid sequencing reactions, and nucleic acid resequencing reactions, as discussed herein. An exemplary type of sample preparation can be used for genotyping, gene-expression, methylation analysis, and/or directed medical sequencing (VariantSEQr™, for example) that requires multiple liquids to be brought together in an aqueous discrete volume. For example, in a gene-expression application, each aqueous discrete volume can contain individual primer sets. The sample to be analyzed, for example, complementary DNA (cDNA), can be added to each aqueous discrete volume. In the VariantSEQr™ application, for example, an aqueous discrete volume can comprise a primer set, and genomic DNA can be added to that discrete volume.

According to various embodiments, one or more sample fluids 22, 24, can be introduced to system 10. Sample fluids 22 and 24, for example, can comprise a nucleic-acid-containing fluid. According to some embodiments, the nucleic acid contained in a sample fluid can be, for example, a single copy of a genomic DNA sequence of an organism, or complementary DNA from an organism.

In some embodiments, a plurality of fluids can be introduced into fluid processing system 10 by way of an immiscible-fluid-discrete-volume-forming conduit 12, which is a part of main conduit system 50. Suitable immiscible-fluid-discrete-volume-forming conduits include, for example, pipettes, capillaries, electro-wetting capillaries, needles, and any device configured to be in fluid communication with fluid processing system 10. Immiscible-fluid-discrete-volume-forming conduit 12 can be part of a system that can comprise, for example, a pump or another apparatus adapted to produce controlled intake of fluids through intake tip 13 into immiscible-fluid-discrete-volume-forming conduit 12. The immiscible-fluid-discrete-volume-forming conduit 12 can be adapted to control an introduction unit to introduce alternate volumes of aqueous sample fluid and spacing fluid that together form discrete volumes of aqueous sample fluid in contact with spacing fluid, i.e., aqueous sample immiscible-fluid-discrete-volumes, in the at least one conduit wherein each aqueous sample immiscible-fluid-discrete-volume can comprise a maximum outer dimension that is equal to or slightly less than the maximum inner cross-sectional dimension of immiscible-fluid-discrete-volume-forming conduit 12. One of skill in the art will understand that the maximum inner cross-sectional dimension of a conduit is the inner diameter of the conduit if the conduit has a circular cross-section.

According to various embodiments, immiscible-fluid-discrete-volume-forming conduit 12 can comprise a tip 13. Tip 13 can interface with fluids to be drawn into system 10. Tip 13 can comprise an angled surface or have any suitable geometry such that the creation of air bubbles in immiscible-fluid-discrete-volume-forming conduit 12 is minimized or eliminated when tip 13 contacts and draws in a fluid. A detailed description of tip 13 can be found below in the description of FIG. 13. Immiscible-fluid-discrete-volume-forming conduit 12 can be robotically controlled, or manually controlled. Robotic configurations can comprise, for example, stepper motors 14, 16, and 18, which can move immiscible-fluid-discrete-volume-forming conduit 12 in X-axis, Y-axis, and Z-axis directions, respectively. In some embodiments, tube 12 can be moved in the Z-axis direction by a stepper motor 18, and a fluid container can be moved in the X-axis and Y-axis directions by stepper motors 14 and 16, respectively. In some embodiments, tube 12 can be stationary and a fluid container can be moved in the X-axis, Y-axis, and Z-axis directions by stepper motors 14, 16, and 19, respectively. Motive force providers other than stepper motors can be used.

According to various embodiments, a variety of fluids can be introduced into fluid processing system 10, in a number of different combinations, depending on the particular type of assay to be performed. The fluids can reside on any suitable fluid retaining device, for example, in the wells of a multi-well plate 20, an opto-electrowetting plate, a tube of preformed slugs, a tube of stable emulsified nanodroplets, individual tubes, strips of tubes, vials, flexible bags or the like.

According to some embodiments, fluid processing system 10 can comprise a number of different fluid conduits and fluid control devices. The following description applies to the embodiment as illustrated in FIGS. 1A and 1B, but one skilled in the art will understand that alterations to fluid processing system 10 can be made while the teachings remain within the scope of the present teachings. As illustrated, fluid processing system 10 can comprise a main system conduit 50. Main conduit system 50 can comprise a plurality of conduits each in fluid communication with, for example, the following exemplary components: T-junctions 52, 66, and 84; holding conduits 56, 60, 63, 64 and 65; valves V-1, V-2, V-5, V-6, V-7, V-8, V-9, V-10, V-11, V-12, and V-13; cross-junctions 68, 70, 76, 86, and 88; and thermal spirals 74, 80, 90, and 92. Along conduit 50, thermal spirals 74, 80, 90, and 92 can be in thermal contact with respective thermal cyclers 74A, 80A, 90A, and 92A Each thermal cycler 74A, 80A, 90A, and 92A can independently comprise a liquid bath, an oven, a plate, a block comprising fluid passages therein, a peltier device, or the like thermal cycling device.

Main conduit system 50 can provide a fluid communication between T-junction 52 and output conduit 54. From T-junction 52, conduit system 50 comprises two pathways that join at cross-junction 68. A first pathway can take a fluid sequentially through holding conduits 56, 60 and 64, and T-junction 66, before reaching cross-junction 68. A second pathway can take a fluid sequentially through holding conduits 50, and 65, and through either T-junction 66, to cross-junction 68, or directly to cross-junction 68. Both the first pathway and the second pathways are configured to hold fluids for later analysis and are configured to interface with devices for moving fluids along the conduits as discussed below.

From cross-junction 70, fluids can move sequentially to thermal spiral 74, cross-junction 76, thermal spiral 80, and T-junction 84. At T-junction 84 fluids can sequentially move either through cross-junction 86, thermal spiral 90, and output conduit 54, or through cross-junction 88, thermal spiral 92, and an output conduit.

According to some embodiments, fluid processing system 10 can comprise pumps 39 and 40. Pump 40 can be configured to remove or add oil to main conduit system 50, and thereby move fluids located therein. Pump 39 can be configured to remove or add oil to main conduit system 50 to move fluids located therein. All of the pumps described herein can create positive and/or negative pressures in the various conduits of system 10.

According to various embodiments, a T-junction can comprise any junction having three discrete pathways extending from, for example, either a Y-junction or a T-junction. In various embodiments, the junction can comprise a valve-less junction where a stream of aqueous sample fluid and a stream of non-aqueous spacing fluid can meet and form at least discrete volumes of the aqueous sample fluid in contact with the non-aqueous spacing fluid. For example, microfabrication technology and the application of electrokinetics or magnetohydrodyamics can achieve fluid pumping in valve-less, electronically controlled systems. Components comprising shape-optimized conduit turns, optimal introduction methods, micromixers, and/or high flow rate electroosmotic pumps can be used in such a valve-less system.

According to some embodiments, system 10 can comprise discrete volume detectors D-1, D-2, D-3, D-4, D-5, D-6, D-7, D-8, D-9, D-10, D-11, D-12, D-13, D-14, D-15, D-16, D-17, D-18, D-19, and D-20, and detector 98. The discrete volume detectors can comprise, for example, fluorescent detectors, infra-red detectors, capacitive detectors, absorption detectors, refractive-index detectors, combinations thereof, and the like. In FIGS. 1A and 1B, all of the detectors depicted are infra-red, refractive-index detectors with the exception of detector 98 which is a fluorescent signal detector, although other arrangements can be used. The discrete volume detectors can be configured to distinguish immiscible-fluid, discrete volumes from spacing fluid or oil as the discrete volumes travel through the conduits of system 10.

According to various embodiments, the system can comprise a thermal-cycling device or thermal cycler, adapted to thermally cycle an aqueous immiscible-fluid, discrete volume in a conduit disposed thereon or therein. In some embodiments, the conduit can contact the thermal cycler in a single straight-line segment, or a coil around the external perimeter of thermal cycler, or a spiral of decreasing radius on one surface, or a serpentine pattern across one or more surfaces of thermal cycler. The thermal-cycling device can comprise a heat source, for example, a radiant heat source, a non-radiant heat source, a peltier device, or the like, and a cooling source, for example, a fan, an air jet, or a liquid-circulating system in a thermal block. The thermal-cycling device can comprise one or more temperature sensors and one or more control units for controlling heating and cooling according to a desired or programmed thermal cycle.

In some embodiments, the conduits of the present teachings can comprise capillary tubes having an inner diameter and the inner diameter can be, for example, about 1000 microns or less, for example, about 800 microns or less, or about 500 microns or less. In some embodiments, the conduit has a minimum inner dimension, or diameter, of from about 1.0 micron to about 100 microns, or from about 50 microns to about 75 microns. In other embodiments, the conduit can have an inner diameter greater than about 300 microns. In some embodiments, the conduit can comprise an inner diameter in the range of from about 0.015 inch to about 0.025 inch, for example, from about 0.019 inch to about 0.025 inch. In some embodiments, the conduit can have a smaller diameter at and/or beginning before a pair of thermal spirals near the downstream end of the system which are designed for forward/reverse sequencing amplification. Other details about the thermal-cycling device, capillary channel or conduit, and other system components will become apparent in view of the teachings herein.

System 10 can comprise a single molecule amplification fluid ("SMAF") conduit system 51. SMAF tube system 51 can supply sample fluid to a T-junction through positive pressure rather than by aspiration. SMAF conduit system 51 can comprise a supply conduit connected to and in fluid communication with a supply of single molecule amplification fluid. The SMAF can comprise a solution or mixture of target nucleic acids diluted to a degree such that there is an average of less than about one target nucleic acid per volume of single molecule amplification fluid that is used to make an immiscible-fluid-discrete-volume. An exemplary concentration of target molecules can be 0.4 molecule per volume used to make an immiscible-fluid-discrete-volume. SMAF conduit system 51 can comprise conduits connecting a SMAF reservoir 69 sequentially to valve V-18 and T-junction 67. SAMF conduit system 51 can comprise conduits that connect T-junction 67 to main conduit system 50 and a rotary valve 71.

Fluid processing system 10 can comprise rotary valves 71, 73, 75, 77, and 79. Each rotary valve can function to direct the flow of metered amounts of different reagents from different respective reagent reservoirs connected thereto, as described below, to main conduit system 50. Syringe pumps 58, 66, 78, and 82 can be in fluid communication with rotary valves 73, 75, 77, and 79, respectively. Pumps 42, 43, 44, and 45 can be in fluid communication with rotary valves 73, 75, 77, and 79, respectively.

Fluid processing system 10 can comprise a first waste conduit system 81. Waste conduit system 81 can comprise conduits connecting the following components: valves V-17, V-20, V-21, V-22, V-23, V-24, V-25, and a waste reservoir 83. Waste conduit system 81 can provide a fluid communication between and cross-junctions 68, 70, 76, 86, and 88 and waste reservoir 83.

Fluid processing system 10 can comprise a second waste conduit system 48. Second waste conduit system 48 can comprise conduits connecting a pump 87, a waste reservoir 85, and a valve V-26, that interface with output conduit 54. Second waste conduit system 48 can be used to remove liquids from output conduit 54.

Fluid processing system 10 can comprise reagent reservoirs 89, 91, 93, 95, 97, and 99 and can be in fluid communication with rotary valves 75, 77, 77, 79, 79, and 73, respectively. Reagent reservoir 89 can contain, for example, an exo-nuclease and shrimp alkaline phosphatase. Reagent reservoir 91 can contain, for example, nucleic acid amplification reaction forward primers. Reagent reservoir 93 can contain, for example, nucleic acid amplification reaction chain terminating dyes. Reagent reservoir 95 can contain, for example, nucleic acid amplification reaction reverse primers. Reagent reservoir 97 can contain, for example, nucleic acid amplification reaction chain terminating dyes. Reagent reservoir 99 can contain, for example, a nucleic acid amplification reaction master mix comprising, for example, reactive single base nucleotides, buffer, a polymerase, and the like, for example, to carry out a polymerase chain reaction.

According to various embodiments, fluid processing system 10 can comprise a rinse conduit system 30. Rinse conduit system 30 can provide a fluid communication between a rinse fluid reservoir 28, rotary valve 73, rotary valve 75, and immiscible-fluid-discrete-volume-forming conduit 12. Rinse fluid reservoir 28 can contain a rinse fluid 26. Rinse fluid 26 can comprise microbiologic grade water, for example, distilled, de-ionized water.

Rinse fluid 26 can be used to remove residual sample, for example, from immiscible-fluid-discrete-volume-forming conduit 12. Rinse fluid can be provided to multi-well plate 20, by way of rinse conduit system 30. Rinse fluid 26 can be used as a rinse at the input station, and/or can be used as a rinse fluid, a dilution fluid, or both, elsewhere in the system. In some embodiments, rinse fluid 26 can be added to immiscible-fluid, discrete volumes to adjust the volume or concentration thereof, in conjunction with an addition station, as described in FIG. 1C.

According to various embodiments, fluid processing system 10 can comprise a spacing fluid conduit system 36. Spacing fluid conduit system 36 can provide a fluid communication between a spacing fluid reservoir 34, vacuum pump 41, and multi-well plate 20. Spacing fluid reservoir 34 can contain an oil 32 or other spacing fluid that is immiscible with an immiscible-fluid-discrete-volume-forming fluid, for example, an aqueous slug fluid.

In some embodiments, the spacing fluid can be non-aqueous. The spacing fluid can comprise an organic phase, for example, a polydimethylsiloxane oil, a mineral oil (e.g., a light white mineral oil), a silicon oil, a hydrocarbon oil (e.g., decane), a fluorinated fluid or a combination thereof. Fluorinated compounds such as, for example, perfluorooctyl bromide, perfluorodecalin, perfluoro-1,2-dimethylcyclohexane, FC 87, FC 72, FC 84, FC 77, FC 3255, FC 3283, FC 40, FC 43, FC 70, FC 5312 (all "FC" compounds are available from 3M, St. Paul, Minn.), the Novec® line of HFE compounds (also available from 3M, St. Paul, Minn.), such as, for example, HFE-7000, HFE-7100, HFE-7200, HFE-7500, and perfluorooctylethane can also be used as the spacing fluid. Combinations, mixtures, and solutions of the above materials can also be used as the spacing fluid.

In some embodiments, fluorinated alcohols, such as, for example, 1H, 1H, 2H, 2H-perfluoro-decan-1-ol, 1H, 1H, 2H, 2H-perfluoro-octan-1-ol, and 1H, 1H-perfluoro-1-nonanol can be added to a fluorinated compound, such as those listed above, to improve the stability of aqueous discrete volumes within the spacing fluid, but still maintain the ability to coalesce upon contact. In some embodiments, fluorinated alcohols can be added in a range of approximately 0.1% to approximately 5% by weight. In some embodiments, the fluorinated alcohol additive can be approximately 0.1%, 0.2%, 0.5%, 1.0%, 1.5%, 2.0%, 3.0%, 4.0% or 5% by weight of the fluorinated compound. In some embodiments, the fluorinated alcohol additive can be from approximately 1% to approximately 10% by volume of the fluorinated compound. In some embodiments, the fluorinated alcohol additive may comprise approximately 1%, 2%, 3%, 4%, 5%, 6%, 7%, 8%, 9%, or 10% by volume of the spacing fluid. In some embodiments, F-alkyl dimorpholinophosphates can be added as surfactants to fluorinated compounds.

In some embodiments, the organic phase can include non ionic surfactants such as sorbitan monooleate (Span 80 (no. S-6760, Sigma)), polyoxyethylenesorbitan monooleate (Tween 80 (no. S-8074, Sigma)), sorbitan monostearate (Span 60), octylphenoxyethoxyethanol (Triton X-100 (no. T9284, Sigma)). In some embodiments, Span 80 can be added in an amount ranging from about 1.0% to about 5.0%, or about 3.0% to about 4.5%. In some embodiments, adding surfactants in the quantities of 4.5% Span 80, 0.40% Tween 80, and 0.05% Triton X-100 to mineral (no. M-3516, Sigma) can result in the creation of stable emulsified droplets.

In some embodiments, the organic phase can include ionic surfactants, such as sodium deoxycholate, sodium cholate, and sodium taurocholate. In some embodiments, the organic phase can include chemically inert silicone-based surfactants, such as, for example, polysiloxane-polycetyl-polyethylene glycol copolymer. In some embodiments, the non-aqueous, spacing fluid can have a viscosity between approximately 0.5 to approximately 0.75 centistokes. In some embodiments, the non-aqueous spacing fluid can have a viscosity between approximately 0.75 centistokes to about 2.0 centistokes. In some embodiments, the non-aqueous spacing fluid can have a viscosity greater than 2.0 centistokes. In some embodiments, the non-aqueous spacing fluid can have a viscosity between 0.5 to greater than about 2.0 centistokes. In some embodiments, the non-aqueous spacing fluid can have a viscosity greater than 2.0 centistokes. In some embodiments, the non-aqueous, spacing fluid can have a boiling point greater than or equal to 100° C.

Spacing fluid 32 can function to separate discrete volumes of an immiscible-fluid-discrete-volume-forming fluid, for example, and aqueous sample, before, during, or after the immiscible-fluid-discrete-volume-forming fluid has been introduced into system 10. Spacing fluid can be provided to multi-well plate 20, from a spacing fluid reservoir 34, by way of a spacing fluid conduit system 36.

According to some embodiments, a de novo nucleic acid sequencing method is provided that uses system 10. The de novo sequencing method can be used to sequence an entire genome or portions thereof. The de novo sequencing method can be especially useful when the sequence of the organism is unknown.

In some embodiments, a de novo sequencing method comprises pre-processing a sample, separating the sample into a set of immiscible-fluid, discrete volumes, optionally adding amplification reagents to each discrete volume of the set, amplifying nucleic acids in the set of immiscible-fluid, discrete volumes to form a set of amplified immiscible-fluid, discrete volumes, optionally detecting, and removing, discrete volumes without amplified sample molecules therein, adding primer and dNTP deactivation agents to each discrete volume in the set, or optionally, to only those with amplified sample molecules, incubating the set of amplified immiscible-fluid, discrete volumes with primer and dNTP deactivation agents, subjecting the resulting nucleic acids to sequencing conditions to form detectable products, and detecting the detectable products.

In some embodiments, the method can comprise pre-processing a sample before the sample fluid is introduced into system 10. The pre-processing of a sample can comprise fragmenting the nucleic acid present in the sample fluid. The fragmentation can be accomplished by any suitable method known in the art. For example, the nucleic acid can be fragmented by enzymatic digestion, or physical disruption methods, for example, hydro-sheering or sonication. In some embodiments the nucleic acid can be fragmented to an average size of about 500 B, 750 B, 850 B, 1 KB, 2 KB, or 3 KB, for example.

According to some embodiments, the pre-processing of sample can comprise ligating sequences to a sample. Universal sequences can be used to facilitate universal nucleic acid amplification. Universal sequences can be artificial sequences that generally have no homology with the target nucleic acids. Universal sequences can be designed to resist the formation of dimers between themselves. Universal sequences can be designed to bind with analogous primers with a consistent efficiency.

According to some embodiments, the present teachings can encompass a de novo sequencing method wherein universal sequences can be ligated to the 5' and 3' ends of the DNA fragments in a sample by, for example, T4 DNA ligase, thereby forming a universal tail. The universal tail sequences can function as sites of complementarity for zip code primers. Details of universal tail procedures can be found in U.S. Pat. App. No. 2004/0185484, to Costa et al., which is incorporated herein, in its entirety, by reference.

According to various embodiments, the amplifying of a nucleic acid can comprise a thermal cycling nucleic acid sequence amplification process or an isothermal nucleic acid sequence amplification process. If a thermal cycling nucleic acid sequence amplification process is used, the process can comprise, for example, a polymerase chain reaction (PCR). The nucleic acid sequence amplification reaction can comprise an exponential amplification process, for example, PCR, or a linear amplification process, as can occur during, for example, during Sanger cycle sequencing. In various embodiments, other nucleic acid amplification processes can be used, for example, ligase chain reaction (LCR), nucleic acid sequence based amplification (NASBA), Q-beta replicase (QB) amplification, or strand displacement amplification (SDA). These alternatives, as well as others known to one skilled in the art, can be used either by themselves or in combination with PCR to amplify nucleic acids.

According to various embodiments, nucleic acid sequence processing methods comprising a first type of nucleic acid amplification reaction followed by one or more of a second different type of amplification reaction, and/or detection assay reaction, can be carried out, for example, as described in U.S. Patent Application No. 60/699,782 to Faulstich et al., filed Jul. 15, 2005, and in U.S. patent application Ser. No. 11/487,729 to Faulstich et al., filed Jul. 17, 2006, which are incorporated herein in their entireties by reference.

According to some embodiments, the present teaching can comprise a method of de novo sequencing wherein, pre-processing of sample can comprise adding zip code primers to a sample of nucleic acid having universal tail sequences ligated therein. Zip code primers can be complementary to the universal tail sequences. The use of zip code tails sequences and zip code primers can reduce the need for target specific primers, resulting in significant cost savings as well as greater assay flexibility.

According to various embodiments, pre-processing a sample can comprise adding to the sample reactants to facilitate a nucleic acid amplification reaction. For example, the four dNTP's (dATP, dTTP, dGTP, and dCTP), a polymerase, oligonucleotide primers, and/or chelating agents can be added to the sample. Oligonucleotide primers can be chosen as determined by one of skill in the art to accomplish the desired objective, for example, universal primers can be used.

According to various embodiments, pre-processing a sample can comprise diluting the sample with a miscible solvent, vehicle, or carrier. The sample can be diluted at a ratio of 1:1, 1:10, 1:100, 1:1000, or 1:10,000, for example. Exemplary ranges of dilution can be from about 1:1 to about 1:100, or from about 1:10 to about 1:50. For example, the sample can be diluted such that only a single fragment of nucleic acid is present per 500 nanoliters of diluted sample, or per 200 nanoliters of diluted sample. In some embodiments, the concentration of target fragments can be based on the size of the immiscible-fluid-discrete-volumes generated that carry the target fragments, such that an average of about 1 target fragment is present per 1.4 immiscible-fluid-discrete-volumes generated. According to various embodiments, the sample can be diluted such that at least 50% immiscible-fluid-discrete-volumes produced from a sample in the process described below can each comprise a single target nucleic acid sequence. In various other embodiments, less than about 50% of the immiscible-fluid-discrete-volumes produced can each comprise a single target nucleic acid sequence. In other embodiments, at least 1% or more, 5% or more, 10% or more, or 20% or more can comprise a single target nucleic acid sequence, for example, from about 10% to about 50% or from about 20% to about 40%.

After optional preprocessing, the sample fluid is introduced to system 10 to form one or more discrete volumes of the sample fluid in a spacing fluid with which it is immiscible. According to various embodiments, the method can comprise forming immiscible-fluid-discrete-volumes of discrete amounts of sample fluid and/or reagents inside conduit system 50. A plurality of immiscible-fluid-discrete-volumes can be associated together as a set of immiscible-fluid-discrete-volumes. Each set of immiscible-fluid-discrete-volumes can comprise immiscible-fluid-discrete-volumes separated from one another by a spacing fluid, for example, an oil. Each immiscible-fluid-discrete-volume of a set can be equally spaced from one or more adjacent immiscible-fluid-discrete-volumes of the set. Multiple sets of immiscible-fluid-discrete-volumes can be present at the same time in main conduit 50. Each set of immiscible-fluid-discrete-volumes can be separated from one or more other sets of immiscible-fluid-discrete-volumes by spacing fluid. In some embodiments, two or more sets of immiscible-fluid-discrete-volumes are spaced from one another a distance that is greater than the average distance between adjacent immiscible-fluid-discrete-volumes with the same set.

In the embodiment depicted in FIGS. 1A and 1B, immiscible-fluid-discrete-volumes that have been aspirated into immiscible-fluid-discrete-volume-forming conduit 12 can be moved into holding conduit 56 by suction produced by vacuum pump 40. More details about an exemplary method of forming sets of immiscible-fluid-discrete-volumes is provided herein, for example, at least in connection with the description of FIGS. 16 and 17 herein.

According to various embodiments, a sample to be subjected to de novo sequencing can comprise a single copy of the genomic DNA of an organism. The sample DNA can be sheared, and universal tails can be ligated to the sample. Nucleic acid amplification reactants can be added to the sample before the sample is drawn into system 10 or after the sample has been drawn into system 10. The nucleic acid amplification reactants can comprise zip code specific primers, for example, primers that are specific to the universal tail sections ligated to the sample nucleic acid fragments. The sample can be diluted such that when the sample is made into immiscible-fluid-discrete-volumes by system 10, each immiscible-fluid-discrete-volume does not contain more than one nucleic acid fragment. For example, 1, 2, 3, 4, or 5 out of ten immiscible-fluid-discrete-volumes can contain nucleic acid fragments.

According to some embodiments, the method can comprise moving a set of immiscible-fluid-discrete-volumes, from T-junction 52, to cross-junction 70, by way of conduit system 50. If a set of immiscible-fluid-discrete-volumes does not contain nucleic acid amplification reactants, the reactants can be added to each immiscible-fluid-discrete-volume of the set of immiscible-fluid-discrete-volumes at cross-junction 70. Reactant addition to each immiscible-fluid-discrete-volume can be metered by rotary valves 71 and 73. Detector D-3 can detect the arrival of the beginning and/or the end of a set of sample immiscible-fluid-discrete-volumes at cross-junction 70. Detector D-21 can detect the arrival of the beginning and/or the end of immiscible-fluid-discrete-volumes at cross-junction 70. Valve V-7 can control the movement of a set of immiscible-fluid-discrete-volumes out of cross-junction 70.

According to some embodiments, the method can comprise moving a set of immiscible-fluid-discrete-volumes from cross-junction 70, through main conduit system 50, to thermal spiral 74. Detector D-8 can be used to detect the arrival of a set of immiscible-fluid-discrete-volumes at thermal spiral 74. Detector D-8 can be used to detect the end of a set of immiscible-fluid-discrete-volumes, and thereby detect that a set of immiscible-fluid-discrete-volumes is disposed in thermal spiral 74. A set of immiscible-fluid-discrete-volumes can be thermally cycled, for one or more cycles, for example, for from about 5 to about 50 temperature cycles or from about 20 to about 30 temperature cycles.

According to various embodiments, the method can comprise introducing polymerase chain reaction inactivating reagents into main conduit 50 after amplifying the at least one target nucleic acid sequence and before subjecting the nucleic acid sequence to a sequencing reaction. The reagents can be used to inactivate or remove or eliminate excess primers and/or dNTP's. The inactivating reagents can be introduced at an junction in the conduit, for example, after an immiscible-fluid-discrete-volume to be inactivated is aligned with the junction. The junction can comprise, for example, a T-junction.

According to some embodiments the method can comprise moving a set of immiscible-fluid-discrete-volumes from thermal spiral 74, through cross-junction 76. As the set of immiscible-fluid-discrete-volumes moves through cross-junction 76, the method can comprise adding exonuclease and shrimp alkaline phosphatase to each immiscible-fluid-discrete-volume of the set of immiscible-fluid-discrete-volumes. For example, the exonuclease and shrimp alkaline phosphatase can be metered out in discrete volumes which merge respectively with the immiscible-fluid-discrete-volumes of a set of immiscible-fluid-discrete-volumes at an junction in rotary valve 77. For example, exonuclease and shrimp alkaline phosphatase can be added to each immiscible-fluid-discrete-volume of the set of immiscible-fluid-discrete-volumes in cross-junction 76.

In the exemplary system shown, detector D-6 can detect the arrival of the beginning and/or the end of a set of sample discrete volumes at cross-junction 76. Detector D-18 can detect the arrival of the beginning and/or the end of one or more immiscible-fluid-discrete-volumes of exonuclease and shrimp alkaline phosphatase at cross-junction 76. Valve V-8 can control the movement of a set of immiscible-fluid-discrete-volumes out of cross-junction 76.

In the exemplary embodiment shown, a set of immiscible-fluid-discrete-volumes containing exonuclease and shrimp alkaline phosphatase can be moved into thermal spiral 80, via main conduit system 50. Detector D-9 can detect the arrival of the beginning and/or the end of a set of immiscible-fluid-discrete-volumes at thermal spiral 80. The set of immiscible-fluid-discrete-volumes can be incubated at from about 25° C. to about 35° C. for a time period of from about one minute, to about 60 minutes or from about two minutes to about 10 minutes. The incubation step can function to facilitate the activities of the exonuclease and shrimp alkaline phosphatase. A set of immiscible-fluid-discrete-volumes can be further incubated at a temperature of from about 75° C. to about 85° C., for a time period of from about 10 seconds to about 10 minutes, or from about one minute to about five minutes. The incubation at from about 75° C. to about 85° C. can function to heat-kill any enzymes that might still be present in the set of immiscible-fluid-discrete-volumes.

According to some embodiments, the method can comprise moving a set of immiscible-fluid-discrete-volumes to T-junction 84. Valve V-9 can control the movement of a set of immiscible-fluid-discrete-volumes from thermal spiral 80, to T-junction 84. Detector D-10 can detect the arrival of the beginning and/or the end of a set of immiscible-fluid-discrete-volumes at T-junction 84. The method can comprise dividing one or more immiscible-fluid, discrete volumes of a set of immiscible-fluid discrete volumes into two or more smaller immiscible-fluid-discrete volumes to form two newly formed sets of equal number of immiscible-fluid discrete volumes, but containing immiscible-fluid discrete volumes of smaller volume. The method can comprise moving one newly created set of immiscible-fluid, discrete volumes along main conduit system 50, to cross-intersection 86. Forward primers and chain terminating dyes can be moved from reservoirs 91 and 93, to rotary valve 77. The forward primers and chain terminating dyes can be metered out by rotary valve 77. The forward primers and chain terminating dyes can be moved to cross-intersection 86 and be added to each immiscible-fluid-discrete-volume of the newly-created set of immiscible-fluid, discrete volumes, thereby creating a forward set of immiscible-fluid, discrete volumes. According to various embodiments, the method can comprise moving the second newly created set of immiscible-fluid, discrete volumes along main conduit system 50, to cross-intersection 88. Reverse primers and chain terminating dyes can be moved from reservoirs 95 and 97, to rotary valve 79. The reverse primers and chain terminating dyes can be metered out by rotary valve 79. The reverse primers and chain terminating dyes reagent can be moved to cross-intersection 86 and be joined with each immiscible-fluid-discrete-volume of the second newly-created set of immiscible-fluid, discrete volumes, thereby creating a reverse set of immiscible-fluid, discrete volumes.

In some embodiments, the method can comprise moving the forward set of immiscible-fluid-discrete-volumes from cross-junction 86, along main conduit system 50, to thermal spiral 90. The forward set of immiscible-fluid-discrete-volumes can be thermally cycled for from about 5 to about 50, temperature cycles, for example, from about 20 to about 40 thermal cycles.

In some embodiments, the method can comprise moving the reverse set of immiscible-fluid-discrete-volumes from cross-junction 88, along main conduit system 50, to thermal spiral 92. The reverse set of immiscible-fluid-discrete-volumes can be thermally cycled for from about 5 to about 50 thermal cycles, for example, from about 20 to about 40 cycles, temperature cycles.

According to various embodiments, the method can comprise moving the forward and the reverse sets of immiscible-fluid-discrete-volumes from their respective thermal spiral to output conduit 54. Movement can be caused by syringe pumps 82A and 82B that can be controlled independently, or together, by a motor 88A operatively connected thereto. Syringe pumps 82A and 82B can push and pull fluids through respective T-junctions 84A and 84B. This arrangement is useful as syringe pumps 82A and 82B can initially pull immiscible-fluid-discrete-volumes into place in the respective thermal spirals 90 and 92, in conjunction with the positive pressure from the pumps on the upstream side of tee 84. Valves V-10 and V-11 can be switched so that immiscible-fluid-discrete-volumes can be pushed out of system 10. In some embodiments, the pushing can be done with one of pumps 82A and 82B at a time; therefore, there is no need to merge two separate sets of immiscible-fluid-discrete-volumes back together into a single set, but rather the separate sets can be individually dispensed. Output conduit 54 can deposit both sets of immiscible-fluid-discrete-volumes on, for example, a multi-well plate.

According to some embodiments, a dye can be added to one or more immiscible-fluid-discrete-volumes of a set of immiscible-fluid-discrete-volumes. The dye can comprise a double-strand (ds), nucleic acid intercalating dye, for example, SYBR green, SYBR gold, EVA green, LC green, or the like. The dye can be added to an aqueous immiscible-fluid-discrete-volume-forming fluid, such as an aqueous sample, before it is added to system 10. The dye can be added to a set of immiscible-fluid-discrete-volumes at any cross-junction of system 10. The dye can be used to discriminate between immiscible-fluid-discrete-volumes that contain ds nucleic acids and immiscible-fluid-discrete-volumes that do not contain ds nucleic acids. The immiscible-fluid-discrete-volumes that do not contain ds nucleic acids can be removed from output conduit 54 before the immiscible-fluid-discrete-volumes are deposited on a multi-well plate 47. The immiscible-fluid-discrete-volumes that do not contain ds nucleic acids can be moved through second waste conduit system 48, to waste reservoir 85. In some embodiments, a dye can be detected by detector 98 to determine whether a discrete volume should be sent to second waste reservoir 85 or be collected. Pump 87 can apply a negative pressure to waste conduit system 48, which can cause the movement of immiscible-fluid-discrete-volumes into waste reservoir 85.

Immiscible-fluid-discrete-volumes deposited on multi-well plate 47 can be subjected to a sequencing reaction to form a detectable product, and the method of the present teachings can comprise detecting the detectable product. In various embodiments, the detectable product can be detected using, for example, a flow cell or a capillary electrophoretic sequencer. In various other embodiments, an off-capillary detector can be used as deemed appropriate.

Shown below is Table 1, which shows a state diagram of various settings that can be implemented for the various valves and detectors of the system shown in FIGS. 1A and 1B, to achieve various different functions, for example, an embodiment of the de novo sequencing method described above.

TABLE 1

| | V-1 | V-2 | V-3 | V-4 | V-5 | V-6 | V-7 | V-8 | V-9 | V-10 | V-11 | V-12 | V-13 | V-14 | V-15 | V-16 | V-17 | V-18 | V-19 | V-20 | V-21 | V-22 | V-23 | V-24 | V-25 |
|---|---|---|---|---|---|---|---|---|---|---|---|---|---|---|---|---|---|---|---|---|---|---|---|---|---|
| Prime SMA Sample | 0 | 1 | 0 | 1 | 0 | 0 | | | | | | | | | | | | 1 | 0 | 1 | | | | | |
|  | 0 | 1 | 0 | 1 | 0 | 0 | | | | | | | | | | | | 0 | 0 | 1 | | | | | |
|  | 0 | 1 | 0 | 1 | 0 | 0 | | | | | | | | | | | | 0 | 0 | 1 | | | | | |
|  | 0 | 1 | 0 | 1 | 0 | 0 | | | | | | | | | | | | 1 | 0 | 1 | | | | | |
| Deliver initial portion of SMAF/MM mixture to ZT-1 | 0 | 0 | 1 | 0 | 1 | 0 | 0 | | | | | 0 | 0 | 1 | 0 | 1 | 0 | 1 | 1 | 0 | 0 | 1 | 1 | | |
|  | 0 | 0 | 1 | 0 | 1 | 0 | 0 | | | | | 0 | 1 | 1 | 1 | 1 | 0 | 0 | 0 | 0 | 1 | 1 | 0 | | |
| Deliver initial portion of oil to ZT-1 | 0 | 1 | 0 | 1 | 0 | 0 | 1 | 0 | | | | 0 | 1 | 1 | 1 | 1 | 0 | 1 | 1 | 1 | 0 | 0 | 1 | | |
| Form initial SMAF Zebra | 0 | 1 | 0 | 1 | 0 | 0 | | | | | | | | | | | | | | | 1 | 1 | 1 | | |
| Deliver intermediate portion(s) of SMAF/MM mixture to ZT-1 | 0 | 0 | 1 | 0 | 1 | 0 | 1 | 0 | | | | 0 | 0 | 1 | 0 | 1 | 0 | 0 | 1 | 0 | 1 | 0 | 1 | | |
|  | 0 | 1 | 0 | 1 | 0 | 0 | 1 | 0 | | | | 0 | 1 | 1 | 1 | 1 | 0 | 1 | 0 | 1 | 1 | 0 | 1 | | |
| Deliver final portion(s) of SMAF/MM mixture to ZT-1 | 0 | 0 | 1 | 0 | 1 | 0 | 1 | 0 | 1 | 1 | 1 | 0 | 1 | 1 | 1 | 1 | 0 | 1 | 0 | 0 | 0 | 0 | 1 | 0 | 0 |
| Amplify DNA | | | | | | | | 0 | 1 | 1 | 1 | | | | | | | | | | | | 0 | | |
| Prime ES reagent path | | | | | | | | 0 | 1 | 1 | 1 | | | | | | | | | | | | 0 | | |
|  | | | | | | | | 0 | 1 | 1 | 1 | | | | | | | | | | | | 1 | | |
| Add ES reagents and load clean up thermal cycler | | | | | 0 | 0 | 0 | 0 | 1 | 1 | 1 | 0 | 1 | 1 | 1 | 1 | 0 | | | | 0 | 0 | 0 | 0 | 0 |
| Clean up after PCR | | | | | 0 | 0 | 1 | 1 | 1 | 1 | 1 | 0 | 1 | 1 | 1 | 1 | 0 | | | | 0 | 0 | 0 | 0 | 0 |
| Prime PF + BD paths | | | | | | | | | 0 | 0 | 0 | | | | | | | | | | | | | | |
|  | | | | | | | | | 0 | 0 | 0 | | | | | | | | | | | | | | |
| Add FP + BD and RP + BD & load cycle sequencing sticky bun | | | | | 0 | 0 | 1 | 1 | 1 | 1 | 1 | 0 | 0 | 1 | 0 | 1 | 0 | | | | 0 | 0 | 0 | 1 | 1 |
|  | | | | | 0 | 0 | 1 | 1 | 1 | 1 | 0 | 0 | 1 | 1 | 1 | 1 | 0 | | | | 0 | 0 | 0 | 0 | 0 |
| Cycle sequence | | | | | | | | | | | | | | | | | | | | | | | | | |
| Dispense sample-laden FP slugs to tray, dispose of other fluids | | | | | 0 | 0 | 1 | 1 | 1 | 1 | 0 | 0 | 0 | 1 | 0 | 1 | 0 | | | | 0 | 0 | 0 | 0 | 0 |
|  | | | | | 0 | 0 | 1 | 1 | 1 | 1 | 0 | 0 | 0 | 1 | 0 | 1 | 0 | | | | 0 | 0 | 0 | 0 | 0 |

TABLE 1-continued

| V-26 | Rotary Valve-ES | Rotary Valve-FP&BD | Rotary Valve-MM_SMF | Rotary Valve-MM_V1 | VICI-1 | VICI-2 | SP-MM | SPES | SP-FP&BD | SP-RP&BD | Footnote | |
|---|---|---|---|---|---|---|---|---|---|---|---|---|
| | | | 0 | | | 1 | | | | | 1 | Prime SMA Sample |
| | | | Oil | | | 1 | | | | | 2 | Deliver initial portion of SMAF/MM mixture to ZT-1 |
| | | | MM | | | 1 | | | | | 3 | |
| | | | MM | | | 1 | | | | | 4 | |
| | | | MM | | | 1 | | | | | 5 | Deliver initial portion of oil to ZT-1 Form initial SMAF Zebra |
| | | | Off | | 1 | | | | | | 6 | |
| | | | | | | | | | | | 7 | |
| | | | MM | | | 1 | | | | | 8 | Deliver intermediate portion(s) of SMAF:MM mixture toZT-1 |
| | | | | | 1 | 1 | | | | | 9 | |
| | | | MM | | | 1 | | | | | 10 | Deliver final portion(s) of SMAF:MM mixture toZT-1 |
| | 0 | | | | | 1 | | | | | 11 | Amplify DNA |
| | Oil | | | | | | | | | | 12 | Prime ES reagent path |
| | out ES | | | | | | | | | | 13 | |
| | out out | 0 | | 0 | 0 | 1 | 0 | out | 0 | 0 | 14 | Add ES reagents and load clean up thermal cycler |
| 0 | 0 | 0 | 0 | 0 | 0 | 1 | 0 | 0 | 0 | 0 | 15 | Clean up after PCR |
| | | Oil | Oil | | | | | | In | In | 16 | Prime PF + BD paths |
| | | out | out | | | | | | out | out | 17 | |
| | | FP | RF | | | | | | In | In | 18 | |
| | | BD | BD | | | | | | In | In | 19 | |
| | | Oil | Oil | | | | | | In | In | 20 | |
| | | out | out | | | | | | out | out | 21 | |
| 0 | 0 | 0 | 0 | | 0 | 0 | 0 | 0 | 1 | 1 | 22 | Add FP + BD and RP + BD & load cycle sequencing sticky bun |
| | | | 0 | | | | | | 0 | 0 | | Cycle sequence |

| | | | | | | | | | |
|---|---|---|---|---|---|---|---|---|---|
| Dispense sample-laden FP slugs to tray, dispose of other fluids | 1 | 0 | 0 | 0 | 0 | 0 | 1 | 1 | 23, 24 |

Footnotes:
1 Pull SMAF into T-intersection (67);
2 Pull oil through T-intersection (67);
3 Pull MM through T-intersection (67);
4 Pull SMAF + MM through D-17;
5 Push SMAF + MM towards T-intersection (66) until D-5 detects AF;
6 Pull, Push oil towards T-intersection (66) until D-4 detects oil;
7 Push oil + SMAF + MM through thermal cycler until D-6 detects zebras or, more likely, D-2 sees only oil;
8 Pull SMAF + MM through D-17;
9 Push oil + SMAF + MM through thermal cycler until D-6 detects zebras or, more likely, D-2 sees only oil;
10 Pull SMAF + MM towards D-17. After total volume of SMAF has entered T-intersection (67), close V-18. After total volume of MM has left Rotarty Valve (71), switch Rotary Valve (71) to "oil" position. Continue pulling SMAF + MM towards D-17 until D-2 sees a;
11 Push oil + SMAF + MM through thermal cycler until D-6 detects zebras or, more likely, D-5 sees only oil;
12 Push oil until D-16 detects oil;
13 Push ES until D-18 detects ES, then push further distance calculated to advance ES to Zebra path;
14 Push until D-6 detects end of batch, then push further distance calculated to advance batch just past ES adder;
15 Push until D-9 detects end of batch, then push further distance calculate to advance batch completely into cleanup thermal cycler;
16 Push SP (78) until D-19 sees oil. Push SP (82) until D-20 sees oil;
17 Pull portion of FP into SP (78). Pull portion of RP into SP (82);
18 Pull portion of BD into SP (78). Pull portion of BD into SP (82);
19 Pull alternating sub-portions of primers and big dyes until complete portion has been loaded;
20 Pull small amount of oil so all aqueous fluids advance into syringe;
21 Push SP (78) until D-19 sees FP + BD. Push SP (82) until D-20 sees RP + BD. Push farther distance calculated to advance FP + BD and RP + BD to Zebra path;
22 Push with pumps until D-11 and D-7 see oil, then push further distance calculated to advance batch just past RP + BD and FP + BD adders;
23 Push with pumps further distance calculated to advance batch into cycle sequencing thermal cycler;
24 Push until FSD-1 detects sample-laden FP slug, then push further distance calculated to move downstream boundary of sample-laden slug just inside dispense tip;
25 Push distance calculated to bead sample-laden slug on dispense tip. Touch bead to bottom of sample well.

According to various embodiments, the present teachings can encompass a resequencing method using system 10. In general, the resequencing method is similar to the de-novo method described herein with modifications as discussed herein.

In some embodiments, the pre-processing of a sample for resequencing comprises shearing a robust sample of nucleic acid having a plurality of copies of one or more nucleic acids of interest, herein also referred to as target sequences. The nucleic acids in the sample can be sheared. The method can comprise adding a plurality of gene specific zip code primers to the sample before introduction to system 10, or the gene specific zip code primers can be added, at for example, at cross-junction 10, to a set of immiscible-fluid-discrete-volumes generated from the sample. Immiscible-fluid-discrete-volumes made from the sample can contain a single copy of a nucleic acid fragment or can contain a plurality of copies of one or more different nucleic acid fragments. Each immiscible-fluid-discrete-volume can contain, for example, from about 50 to about 150 different gene-specific zip code primers. The gene-specific zip code primers can be present at a relatively low concentration. Exemplary low concentrations can comprise from about 0.1 nanomolar primers per nanoliter (primers/nl) to about 1 micromolar primers/nl, or from about 10 nanomolar primers per nanoliter (primers/nl) to about 50 nanomolar primers/nl.

According to some embodiments, the method can comprise adding sequence-specific zip code primers, specific to a single zip code sequence, to each immiscible-fluid-discrete-volume of a set of immiscible-fluid-discrete-volumes. The sequence-specific zip code primers added to each immiscible-fluid-discrete-volume can be different for one immiscible-fluid-discrete-volume than for at least one other immiscible-fluid-discrete-volume, and can be complementary to the zip code sequences of a specific set of gene-specific zip code primers. The sequence-specific zip code primers can be present in a high concentration relative to the concentration of the gene-specific zip code primers. For example, the concentration of the sequence specific zip code primers can be in excess, and the concentration of the gene specific zip code primers can be limiting. The concentration of the sequence specific zip code primers can be present, relative to the concentration of the gene-specific zip code primers, at, for example, a ratio of from about 10 nanomolar to about 1 micromolar, or from about 100 nanomolar to about 500 nanomolar.

In some embodiments, the method can comprise moving a set of immiscible-fluid-discrete-volumes comprising the concentrations of primers discussed above, to thermal spiral 74. The set of immiscible-fluid-discrete-volumes can be thermally cycled and thereafter processed in any of the many manners disclosed herein for the de novo sequencing method. Various sequencing and re-sequencing methods that can be carried out according to various embodiments can include, for example, those depicted in FIGS. 2C-2K of co-pending U.S. patent application Ser. No. 11/507,735, filed Aug. 22, 2006, entitled "Apparatus, System, and Method Using Immiscible-Fluid-Discrete-Volumes," to Lee et al., which is incorporated herein in its entirety by reference.

Shown below are Tables 2A and 2B which are the first and second halves of another state diagram of various settings that can be implemented for the various valves and detectors of the system shown in FIGS. 1A and 1B, to achieve various different functions. The various functions can include carrying out various different immiscible-fluid-discrete-volume processing, for example, carrying out the standard resequencing reactions depicted in FIGS. 2C-2D of U.S. patent application Ser. No. 11/507,735, filed Aug. 22, 2006, entitled "Apparatus, System, and Method Using Immiscible-Fluid-Discrete-Volumes," to Lee et al.

TABLE 2A

|  | V-1 | V-2 | V-3 | V-4 | V-5 | V-6 | V-7 | V-8 | V-9 | V-10 | V-11 | V-12 | V-13 | V-14 | V-15 | V-16 | V-17 |
|---|---|---|---|---|---|---|---|---|---|---|---|---|---|---|---|---|---|
| Prime Primary VI Input Path | 0 |  |  | 0 | 0 |  |  |  |  |  |  |  | 0 | 0 | 1 | 0 | 1 |
| Form VI Zebra | 0 |  |  | 0 | 0 |  |  |  |  |  |  |  | 0 | 0 | 1 | 0 | 1 |
|  | 0 |  |  | 0 | 0 |  |  |  |  |  |  |  | 0 | 0 | 1 | 0 | 1 |
|  | 0 |  |  | 0 | 0 |  |  |  |  |  |  |  | 0 | 0 | 1 | 0 | 1 |
|  | 0 |  |  | 0 | 0 |  |  |  |  |  |  |  | 0 | 0 | 1 | 0 | 1 |
|  | 0 |  |  | 0 | 0 |  |  |  |  |  |  |  | 0 | 0 | 1 | 0 | 1 |
| Push Zebra Into Storage | 0 |  |  | 0 | 0 | 0 |  |  |  |  |  |  | 1 | 1 | 0 | 1 | 0 |
| Repeat "Form VI Zebra" and "Push Zebra Into Storage" until D-4 sees zebras or until the total required number of slugs is reached. |
| Prime Secondary VI Input Path | 1 | 1 | 0 | 1 | 0 | 0 |  |  |  |  |  |  | 0 | 0 |  |  |  |
| Form secondary VI fluid macro slugs | 1 | 1 | 0 | 1 | 0 | 0 |  |  |  |  |  |  | 0 | 0 |  |  |  |
|  | 1 | 1 | 0 | 1 | 0 | 0 |  |  |  |  |  |  | 0 | 0 |  |  |  |
|  | 1 | 1 | 0 | 1 | 0 | 0 |  |  |  |  |  |  | 0 | 0 |  |  |  |
| Push Macro-Zebra Into Storage |  | 0 | 1 | 0 | 0 | 0 |  |  |  |  |  |  |  |  |  |  |  |
| Repeat "Form secondary VI fluid macro slugs" and "Push Macro-Zebra Into Storage" until D-4 sees zebras or until the total required number of slugs is reached. |
| Add Secondary VI fluid to Zebra slugs |  | 0 | 1 | 0 | 0 | 1 | 0 | 0 |  |  |  |  | 0 | 1 | 1 | 0 | 1 | 0 |
| Prime MM_VI |  |  |  |  |  |  |  |  |  |  |  |  |  |  |  |  |  |
| Add MM to VI Zebra slugs |  | 0 | 1 | 0 | 0 | 1 | 1 | 0 |  |  |  |  | 0 | 1 | 1 | 0 | 1 | 0 |
| Amplify DNA |  |  |  |  |  |  | 0 | 0 |  |  |  |  |  |  |  |  |  |

TABLE 2A-continued

|  | V-18 | V-19 | V-20 | V-21 | V-22 | V-23 | V-24 | V-25 | V-26 | Rotary Valve (75) | Rotary Valve (77) | Rotary Valve (71) | Rotary Valve (73) |
|---|---|---|---|---|---|---|---|---|---|---|---|---|---|
| Prime Primary VI Input Path |  |  |  |  |  |  |  |  |  |  |  |  |  |
| Form VI Zebra |  |  |  |  |  |  |  |  |  |  |  |  |  |
| Push Zebra Into Storage |  |  |  | 1 | 1 |  |  |  |  |  |  |  |  |
| Repeat "Form VI Zebra" and "Push Zebra Into Storage" until D-4 sees zebras or until the total required number of slugs is reached. |
| Prime Secondary VI Input Path | 0 | 0 | 1 |  |  |  |  |  |  |  |  |  |  |
| Form secondary VI fluid macro slugs | 0 | 0 | 1 |  |  |  |  |  |  |  |  |  |  |
|  | 0 | 0 | 1 |  |  |  |  |  |  |  |  |  |  |
|  | 0 | 0 | 1 |  |  |  |  |  |  |  |  |  |  |
| Push Macro-Zebra Into Storage |  | 1 | 0 |  |  |  |  |  |  |  |  |  |  |
| Repeat "Form secondary VI fluid macro slugs" and "Push Macro-Zebra Into Storage" until D-4 sees zebras or until the total required number of slugs is reached. |
| Add Secondary VI fluid to Zebra slugs | 1 | 0 | 0 | 1 | 0 |  |  |  |  |  |  |  | 0 |
| Prime MM_VI |  |  |  |  |  |  |  |  |  |  | 0 |  | MM |
| Add MM to VI Zebra slugs | 1 | 0 | 0 | 0 | 1 |  |  |  |  |  |  |  | Out |
| Amplify DNA |  |  |  |  | 0 |  |  |  |  |  | 0 |  |  |

|  | Rotary Valve (79) | Pump (40) | Pump (39) | SP (58) | SP (66) | SP (78) | SP (82) |
|---|---|---|---|---|---|---|---|
| Prime Primary VI Input Path |  | 1 |  |  |  |  | Pull oil from reservoir until it reaches D-15, then pump distance calculated to advance oil at D-17 just past V-17. |
| Form VI Zebra |  | 1 |  |  |  |  | Pull 78 nl primary VI fluid into tube through tip. Wash tip. |
|  |  | 1 |  |  |  |  | Pull 800 nl oil into tube through tip. Wash tip. |
|  |  | 1 |  |  |  |  | Pull 78 nl primary VI fluid from next well into tube through tip. Wash tip. |
|  |  | 1 |  |  |  |  | Pull 800 nl oil into tube through tip. Wash tip. |
|  |  | 1 |  |  |  |  | Continue aspiration steps until zebras (sequence of immiscible fluid volumes) are detected by D-15. |
| Push Zebra Into Storage |  | 1 |  |  |  |  | Push oil until D-16 no longer sees slugs (individual fluid volumes). |
| Repeat "Form VI Zebra" and "Push Zebra Into Storage" until D-4 sees zebras or until the total required number of slugs is reached. |
| Prime Secondary VI Input Path |  |  | 1 |  |  |  | Pull oil from reservoir until it reaches D-17, then pump distance calculated to advance oil at D-17 just past V-17. |
| Form secondary VI fluid macro slugs |  |  | 1 |  |  |  | Pull m (78 nl) of secondary VI fluid i into tube, where m is the number of primary VI fluids that are to be mixed with the ith secondary fluid. |
|  |  |  | 1 |  |  |  | Pull 800 nl oil into tube through tip. Wash tip. |
|  |  |  | 1 |  |  |  | Continue aspiration steps until zebras are detected by D-17. |
| Push Macro-Zebra Into Storage |  |  |  |  |  |  | Pump oil to push macro-zebra until D-2 no long sees macro-slugs. |
| Repeat "Form secondary VI fluid macro slugs" and "Push Macro-Zebra Into Storage" until D-4 sees zebras or until the total required number of slugs is reached. |
| Add Secondary VI fluid to Zebra slugs |  | 1 | 1 | 0 |  |  | Push micro and macro zebras until D-3 sees slugs |
| Prime MM_VI |  |  |  | 1 |  |  | Load Syringe Pump (58) |
| Add MM to VI Zebra slugs |  | 1 | 1 | 1 |  |  | Runs pumps until D-6 sees slugs |
| Amplify DNA |  |  |  |  |  |  |  |

TABLE 2B

|  | V-1 | V-2 | V-3 | V-4 | V-5 | V-6 | V-7 | V-8 | V-9 | V-10 | V-11 | V-12 | V-13 | V-14 | V-15 | V-16 | V-17 |
|---|---|---|---|---|---|---|---|---|---|---|---|---|---|---|---|---|---|
| Prime ES Reagent path |  |  |  |  |  |  |  | 0 | 0 | 1 | 1 |  |  |  |  |  |  |
|  |  |  |  |  |  |  |  | 0 | 0 | 1 | 1 |  |  |  |  |  |  |
| Add ES Reagents & load cleanup thermal cycler |  |  |  |  | 0 | 0 | 1 | 1 | 1 | 1 | 1 | 0 | 1 | 1 | 0 | 1 | 0 |
|  |  |  |  |  | 0 | 0 | 1 | 1 | 1 | 1 | 1 | 0 | 1 | 1 | 0 | 1 | 0 |
| Clean up after PCR |  |  |  |  |  |  | 0 | 0 |  |  |  |  |  |  |  |  |  |
| Prime FP + BD and RP + BD paths |  |  |  |  |  |  |  |  | 0 | 0 | 0 |  |  |  |  |  |  |
|  |  |  |  |  |  |  |  |  | 0 | 0 | 0 |  |  |  |  |  |  |
| Add FP + BD and RP + BD & load cycle sequencing thermal cycler |  |  |  |  | 0 | 1 | 1 | 1 | 1 | 1 | 1 | 0 | 1 | 1 | 0 | 1 | 0 |
|  |  |  |  |  | 0 | 0 | 1 | 1 | 1 | 1 | 1 | 0 | 1 | 1 | 0 | 1 | 0 |
| Cycle sequence |  |  |  |  |  |  |  |  | 0 | 0 | 0 |  |  |  |  |  |  |

TABLE 2B-continued

| | V-18 | V-19 | V-20 | V-21 | V-22 | V-23 | V-24 | V-25 | V-26 | Rotary Valve (75) | Rotary Valve (77) | Rotary Valve (71) | Rotary Valve (73) |
|---|---|---|---|---|---|---|---|---|---|---|---|---|---|
| Dispense sample-laden FP slugs to tray, dispose of other fluids | | | 0 | 0 | 1 | 1 | 1 | 1 | 0 | 0 | 1 | 1 | 0 | 1 | 0 |
| | | | 0 | 0 | 1 | 1 | 1 | 1 | 0 | 0 | 1 | 1 | 0 | 1 | 0 |

| | V-18 | V-19 | V-20 | V-21 | V-22 | V-23 | V-24 | V-25 | V-26 | Rotary Valve (75) | Rotary Valve (77) | Rotary Valve (71) | Rotary Valve (73) |
|---|---|---|---|---|---|---|---|---|---|---|---|---|---|
| Prime ES Reagent path | | | | | | 1 | | | | Oil Out ES | | | |
| | | | | | | 1 | | | | Out | | | |
| Add ES Reagents & load cleanup thermal cycler | | | 0 | 0 | 0 | 0 | 0 | | | Out | 0 | | 0 |
| | | | 0 | 0 | 0 | 0 | 0 | | | 0 | 0 | | 0 |
| Clean up after PCR | | | | | | | | | | | | | |
| Prime FP + BD and RP + BD paths | | | | | | | | | | Oil | | | |
| | | | | | | 1 | 1 | | | Out FP BD Oil | | | |
| | | | | | | 1 | 1 | | | Out | | | |
| Add FP + BD and RP + BD & load cycle sequencing thermal cycler | | | 0 | 0 | 0 | 0 | 0 | | | 0 | Out | | 0 |
| | | | 0 | 0 | 0 | 0 | 0 | | | 0 | 0 | | 0 |
| Cycle sequence | | | | | | 0 | 0 | | | | 0 | | |
| Dispense sample-laden FP slugs to tray, dispose of other fluids | | | 0 | 0 | 0 | 0 | 0 | 1 | | 0 | 0 | | 0 |
| | | | 0 | 0 | 0 | 0 | 0 | 0 | | 0 | 0 | | 0 |

| | Rotary Valve (79) | Pump (40) | Pump (39) | SP (58) | SP (66) | SP (78) | SP (82) | |
|---|---|---|---|---|---|---|---|---|
| Prime ES Reagent path | | | | | In | | | |
| | | | | | Out In | | | Push oil until D-18 detects oil. |
| | | | | | Out | | | Push ES until D-18 detects ES, then push further distance calculated to advance ES to zebra path. |
| Add ES Reagents & load cleanup thermal cycler | 0 | 1 | 0 | 0 | Out | 0 | 0 | Push until D-6 detects end of batch, then push further distance calculated to advance batch just past ES adder. |
| | 0 | 1 | 0 | 0 | 0 | 0 | 0 | Push until D-9 detects end of batch, then push further distance calculate to advance batch completely into cleanup thermal cycler. |
| Clean up after PCR | | | | | | | | |
| Prime FP + BD and RP + BD paths | Oil | | | | | In | In | |
| | Out | | | | | Out | Out | Push SP-FP&BD until D-19 sees oil. Push SP (82) until D-20 sees oil. |
| | RP | | | | | In | In | Pull portion of FP into SP (78). Pull portion of RP into SP-RP&BD. |
| | BD | | | | | In | In | Pull portion of BD into SP (78). Pull portion of BD into SP (82). Pull alternating sub-portions of primers and big dyes until complete portion has been loaded. |
| | Oil | | | | | In | In | Pull small amount of oil so all aqueous fluids advance into syringe. |
| | Out | | | | | Out | Out | Push SP (78) until D-19 sees FP + BD. Push SP (82) until D-20 sees RP + BD. Push farther distance calculated to advance FP + BD and RP + BD to zebra path. |
| Add FP + BD and RP + BD & load cycle sequencing thermal cycler | Out | 1 | 0 | 0 | 0 | 1 | 1 | Push with pumps until D-11 and D-7 see oil, then push further distance calculated to advance batch just past RP + BD and FP + BD adders. |
| | 0 | 1 | 0 | 0 | 0 | 0 | 0 | Push with pumps further distance calculated to advance batch into cycle sequecning thermal cycler. |
| Cycle sequence | 0 | | | | | | | |
| Dispense sample-laden FP slugs to tray, dispose of other fluids | 0 | 1 | | | | | | Push until fluorescent detector (98) detects sample-laden FP slug, then push further distance calculated to move downstream boundary of sample-laden slug just inside dispense tip. |
| | 0 | 1 | | | | | | Push distance calculated to bead sample-laden slug on dispense tip. Touch bead to bottom of sample well. |

Figure 1C:
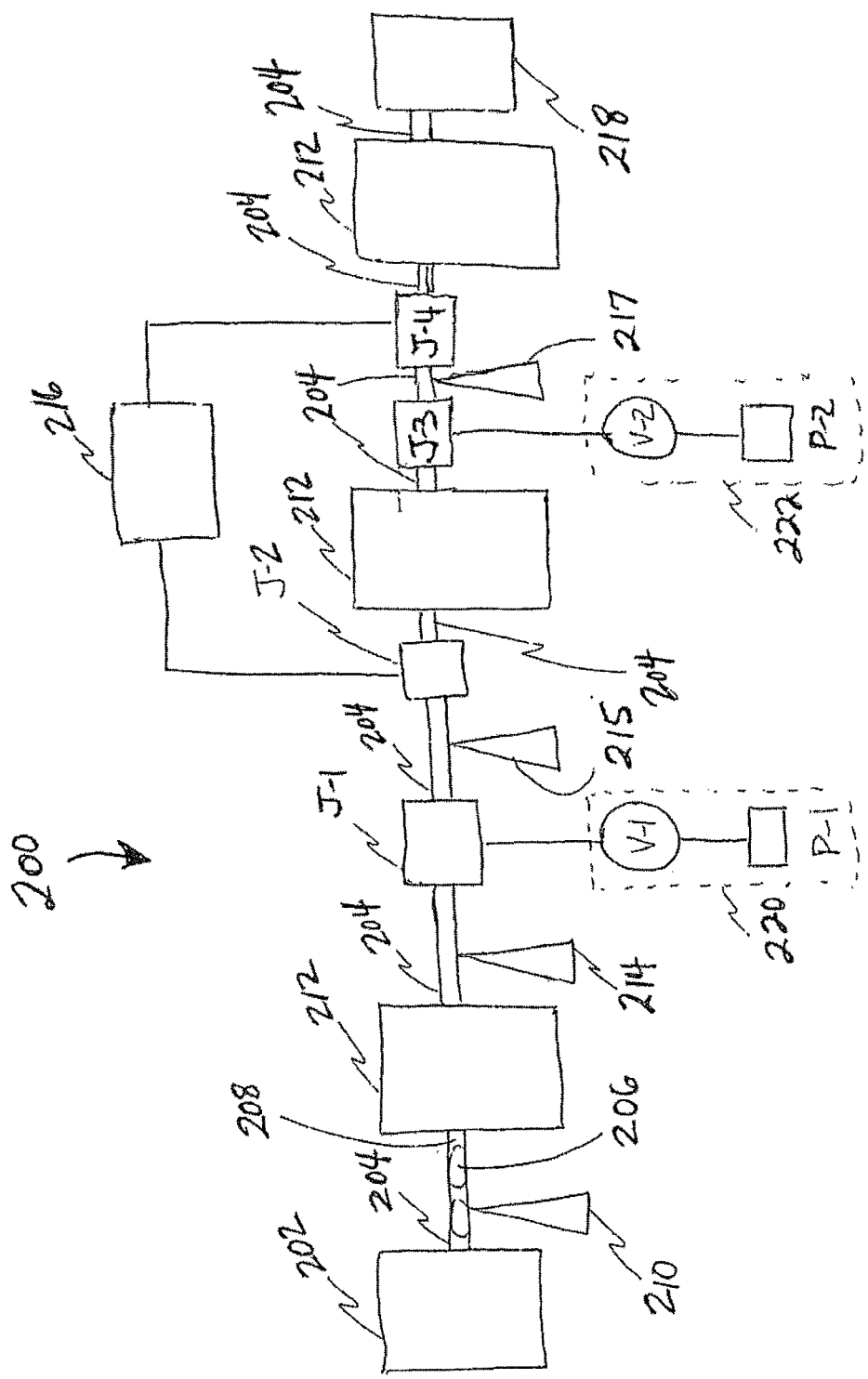
FIG. 1C is a simplified block diagram of a system configured to include embodiments described herein and to process the generated immiscible-fluid-discrete-volumes and to output the immiscible-fluid-discrete-volume.

FIG. 1C is yet another system for processing immiscible-fluid-discrete volumes downstream of the apparatuses, methods, and systems disclosed herein.

A simplified system 200 is illustrated in FIG. 1C. As illustrated, box 202 represents a structure that delivers to tube 204 of system 200 discrete volumes 206 of aqueous liquid in a non-aqueous liquid 208 with which they are immiscible. Examples of such structures and methods of generating discrete volumes 206 in contact with spacing fluid 208 are described herein. In some embodiments, such a structure could be a tube of preformed discrete volumes 206 of aqueous fluid. In some embodiments, such a structure could be a chip or other substrate with a channel therein containing the discrete volumes 206 of aqueous fluid. As illustrated, tube 204 extends throughout system 200. After entering tube 204, desired information about aqueous volumes 206 are determined and optionally manipulated by structures in triangle 210. For example, the length and speed of a slug and the distance between two adjacent slugs can be desired information. In that example, a slug detection system can provide that information. If the distance between adjacent slugs does not meet preferred values, then additional spacing fluid can be added between the trailing point of the first slug and the leading point of the second slug, or one of the slugs could be held in an electric field, for example, to allow more of the existing spacing fluid to flow past it in tube 203. If the length, and therefore the volume, of an aqueous discrete volume does not meet preferred values, additional non-reactive, miscible liquid can be added by an apparatus at that area of tube 204. Triangle 210 represents these and other structures of discrete volume characteristic detection and manipulation. Examples of these structures and/or component parts of thereof are described herein.

System 200, as illustrated in FIG. 1C, next incorporates a processing section 212 of tube 204 (not illustrated, but in the box), which can include, for example, vibration, heating, cooling, and electromagnetic radiation exposure. In some embodiments, processing section 212 can include thermal cycling between one or more pre-determined temperatures for pre-determined durations as needed, for example, to perform PCR, or other amplification methods. In some embodiments, aqueous discrete volumes may continue to flow at a constant rate through processing section 212 while undergoing a desired process, or alternatively, they may dwell in a particular location in processing section 212. System 200, as illustrated in FIG. 1C, includes another aqueous discrete volume characteristic determination and optional manipulation station 214. Aqueous discrete volumes 206 then flow through a junction J-1. In some embodiments, junction J-1 can be a T. As illustrated, fluid addition station 220 includes pump P-1 and valve V-1 in conjunction with a supply of different fluid (not shown) and can add that fluid to tube 204. In some embodiments, a gas phase can be introduced between aqueous discrete volumes 206. In some embodiments, an aqueous liquid can be added to aqueous discrete volumes 206 in junction J-1. In some embodiments, the different aqueous fluid can be added a discrete volume between aqueous discrete volumes 206. An aqueous discrete volume characteristic determination and optional manipulation station 215, like 214 and 210 described above, follows liquid addition station 220. In some embodiments, station 215 evaluates the volume of liquid added to aqueous discrete volume 206.

Next in line, as illustrated in FIG. 1C, is junction J-2. Junction J-2 and junction J-4, further down the line, fluidically connect back pressure unit 216 to pressurize tube 204 to a desired pressure. Between junctions J-2 and J-4, system 200 includes a second processing section 212, a junction J-3, at which point, fluid adding station 222 can add a volume of liquid to pre-existing aqueous discrete volumes. 206, and an aqueous discrete volume characteristic determination and optional manipulation station 217 can evaluate the volume of liquid added to aqueous discrete volume 206.

As illustrated in FIG. 1C, system 200 includes a final processing section 212, and processed aqueous discrete volumes are delivered from tube 204 to output station 218. Examples of structures used in output station 218 are described in concurrently filed U.S. patent application Ser. No. 11/507,733, filed Aug. 22, 2006, entitled "Device, System, and Method for Depositing Processed Immiscible-Fluid-Discrete-Volumes, to Schroeder et al.

Reference will now be made to various embodiments of devices, apparatus, systems, and methods for generating immiscible-fluid-discrete-volumes of a first fluid separated from one another by an immiscible spacing fluid, examples of which are illustrated in the accompanying drawings. Various embodiments of these can be used in the system described above with reference to FIGS. 1A and 1B. Wherever possible, the same reference numbers are used in the drawings and the description to refer to the same or like parts.

According to various embodiments, an apparatus is provided comprising a first conduit exemplified herein as an inner tube, a second conduit exemplified herein as an outer tube, a first pump, and a second pump. The inner tube can comprise a length, an inner surface, an outer surface, an outer diameter, and at least a first end surface, and the outer tube can comprise a length, an inner surface, an inner diameter, an outer surface, and at least a second end surface, wherein the inner tube can be positioned within the outer tube and the inner diameter of the outer tube is greater than the outer diameter of the inner tube such that a fluid can flow in a space between the outer surface of the inner tube and the inner surface of the outer tube. The first pump can be in fluid communication with the inner tube, wherein the first pump is configured to flow a fluid through the inner tube in a first direction, and the second pump can be in fluid communication with the outer tube, where the second pump can be configured to flow a fluid through the outer tube in a second direction opposite the first direction. It should be understood that while tubes are exemplified herein, any suitable conduits can instead be used, and the conduits do not have to have any particular shape or dimensions. In various embodiments, at various times the end surface of the inner tube can be positioned beyond the end surface of the outer tube. In various embodiments, the outer diameter of the inner tube can be less than about 10 mm, less than about 1 mm, or less than 0.1 mm. In other embodiments, the inner diameter of the outer tube can be greater than about 10 mm, greater than about 1 mm, or greater than about 0.1 mm. Regardless of the outer diameter or perimeter of the inner tube, the inner diameter or perimeter of the outer tube will be greater than the outer diameter or perimeter of the inner tube, such that a fluid passage can be formed in the space between the outer tube and the inner tube.

According to various embodiments, the apparatus can comprise a control unit configured to synchronize actuation of the first pump and the second pump. According to various embodiments, the apparatus can comprise a conduit positioner configured to move at least one of the inner tube and the outer tube with respect to the other. In various embodiments, the apparatus can comprise a control unit configured to synchronize actuation of the first pump, the second pump, and the conduit positioner. The synchronized actuation of the pumps and conduit positioner can result in production of a plurality of aqueous immiscible-fluid-discrete-volumes, each of which is immiscible with a non-aqueous spacing fluid that separates the aqueous immiscible-fluid-discrete-volumes from one another. In various embodiments, the actuation of the pumps and conduit positioner can result in rinsing the tip of the inner tube between sample liquid drawing steps, thereby avoiding contamination of a subsequently drawn sample liquid with the previously drawn sample liquid. One of skill in the art can determine additional patterns of actuation of the pumps and the conduit positioner, as well as appropriate pump pressures, to accomplish a desired result.

According to various embodiments, the apparatus can comprise a block in the form of a housing, shroud, casing, or the like. The block can comprise a through-hole having a diameter that is greater than the outer diameter of the inner tube or maximum outer dimension of an inner conduit of a different shape. The block having a through-hole can take the place of an outer tube and can function as the outer fluid conduit, or, in another embodiment, can be provided in addition to an inner tube and an outer tube. At least a portion of the inner tube can be disposed in the through-hole of the block. In various embodiments, an inner conduit, an outer conduit, and a block can all three be included in the apparatus, and the end surface of the outer conduit can be disposed within the through-hole of the block, and/or the end surface of the inner tube can be disposed within the through-hole of the block. In other embodiments, the inner conduit can extend beyond the end surface of the outer conduit and beyond the block.

According to various embodiments, the apparatus can comprise a block having a through-hole, and a passageway in the block, the passageway can be in fluid communication with the through-hole. According to various embodiments, the apparatus can comprise a pump in fluid communication with the passageway and configured to draw fluid from the conduits in the through-hole and into the passageway. In other embodiments, the passageway may not be in fluid communication with the through-hole. Rather the open end of the through-hole and an open end of the passageway may be in sufficiently close proximity such that a fluid from a tube in the through-hole can be sucked into the open end of the passageway. The passageway can lead to or be operatively connected to a waste container or other container into which the fluid can be deposited.

According to various embodiments, a system is provided comprising an apparatus and a supply of oil. In various embodiments, the apparatus can also comprise a supply of an aqueous liquid, for example, an aqueous biological sample solution, or other aqueous-based reagents. In various embodiments, the system can comprise sample liquid disposed in a sample container, and the positioner is configured to move the tip of the inner tube into the sample container and into contact with the sample liquid.

According to various embodiments, a method is provided comprising pumping a first fluid in a first direction in a space between the outer perimeter of an inner conduit and the inner perimeter of an outer conduit, drawing the first fluid past the end surface of the inner conduit and into the inner conduit in a second direction, wherein the second direction is opposite the first direction, and positioning the end surface of the inner conduit past the end surface of the outer conduit. In various embodiments, the method can comprise contacting a second fluid with the end surface of the inner conduit and drawing at least a portion of the second fluid into the inner conduit. According to various embodiments, the first fluid and the second fluid can be immiscible with respect to one another.

According to various embodiments, the method can comprise moving the inner conduit into the outer conduit such that the end surface of the inner conduit and the end surface of the outer conduit are flush or relatively flush with one another, that is, within one millimeter or less of each other, or such that the end surface of the inner conduit can be inside the outer conduit. Various embodiments can comprise moving the end surface of the outer conduit into a through-hole of a block or shroud, such that the end surface of the outer conduit us inside the through-hole.

According to various embodiments, the method can comprise rinsing the end surface of the inner conduit with the first fluid, and drawing away from the end surface of the inner conduit the first fluid used to rinse the end surface of the inner conduit. In various embodiments, the fluid used to rinse the end surface the inner conduit can be flushed through-a passageway of a block. According to various embodiments, the block can comprise a passageway and the method can comprise drawing the first fluid used to rinse the end surface of the inner conduit through-the passageway and away from the through-hole.

According to various embodiments, aqueous immiscible-fluid-discrete-volumes can be confined between oil immiscible-fluid-discrete-volumes that can act as a spacer material to preserve individuality of the aqueous immiscible-fluid-discrete-volumes. According to various embodiments, the flow in the tube, channel, or other conduit can be laminar, with a velocity profile along the tube's axial orientation, with little or no velocity component in the radial direction.

To generate aqueous immiscible-fluid-discrete-volumes in a channel, for example, a channel having a tube format, one can drive or push the individual liquids into the tube. The immiscible-fluid-discrete-volumes can be driven or pushed by a syringe, a pump, or any other suitable apparatus or mechanism. Using a manifold configuration, different liquids can be pushed into the manifold and/or liquid in the manifold, to generate unique immiscible-fluid-discrete-volumes. According to various embodiments, the set of immiscible-fluid-discrete-volumes can be interleaved, alternated, or otherwise sequenced in a desired order or pattern, according to the controlled introduction and/or fluid flow control.

According to various embodiments, a non-aqueous spacing fluid, for example, an oil, and aqueous immiscible-fluid-discrete-volumes, can be prepared and/or combined in a system as described with reference to FIG. 2A. The system can comprise apparatus 100 and apparatus 100 can comprise an inner conduit and an outer conduit exemplified as the coaxially arranged tubes illustrated in FIG. 2A and FIG. 2B. In some embodiments, the system can be used in the system of FIGS. 1A and 1B. As shown, apparatus 100 can comprise inner tube 113 comprising inner surface 109, outer surface 107, inner diameter 122, outer diameter 111, and first end surface 115. Outer tube 114 comprises inner surface 103, inner diameter 112, outer surface 101, and end surface 116. As shown, inner tube 113 is positioned within outer tube 114 and inner diameter 112 of outer tube 114 is greater than outer diameter 111 of inner tube 113, such that a fluid can flow between outer surface 107 of inner tube 113 and inner surface 103 of outer tube 114. FIG. 2B is a cross-sectional view of FIG. 2A taken along line 2B-2B of FIG. 2A.

According to various embodiments, one of inner tube 113 and outer tube 114 can move axially relative to the other. This can allow the end surface 115 of inner tube 113 to be beyond end surface 116 and, if desired, in a liquid, for example, into an aqueous solution, disposed in a receptacle. An example of an arrangement wherein inner tube 113 extends past outer tube 114 can be seen in FIG. 3. When inner tube 113 is positioned in an aqueous solution 119, and a pump 160 (shown in FIG. 6) is operatively connected to inner tube 113, aqueous solution 119 can be sucked into inner tube 113. Alternatively, when end surface 115 of inner tube 113 is not beyond end surface 116 of outer tube 114, a pump 180 (shown in FIG. 6) is operatively connected to inner tube 113, and pump 180 is configured to pump in a direction opposite the direction of flow through outer tube 114, a spacing fluid, for example, oil, can flow in a first direction between the two tubes and be sucked in an opposite direction into inner tube 113. The regulation of various factors, for example, pressure, flow rate, and tube movement, can be regulated by a controller, for example, a computer.

According to various embodiments, and referring again to FIG. 2A, spacing fluid 105, for example, an oil, can be pumped through a space or passage 117 formed between inner tube 113 and outer tube 114. Under appropriate conditions, the spacing fluid can be made to flow extend beyond end surface 116 of outer tube 114, past end surface 115 of inner tube 113, and be sucked into inner tube 113. After spacing fluid 105 flows past end surface 115 and into inner tube 113, the spacing fluid 106 can fill the inner cross-sectional area of inner tube 113 and form a boundary (FIG. 3) for an aqueous immiscible-fluid-discrete-volume. Spacing fluid 106 can fill inner tube 113 such that volumes of spacing fluid 106 between aqueous immiscible-fluid-discrete-volumes can comprise an outer dimension that is equal to the maximum inner cross-sectional dimension (inner diameter) 122 of inner tube 113.

Figure 2A:
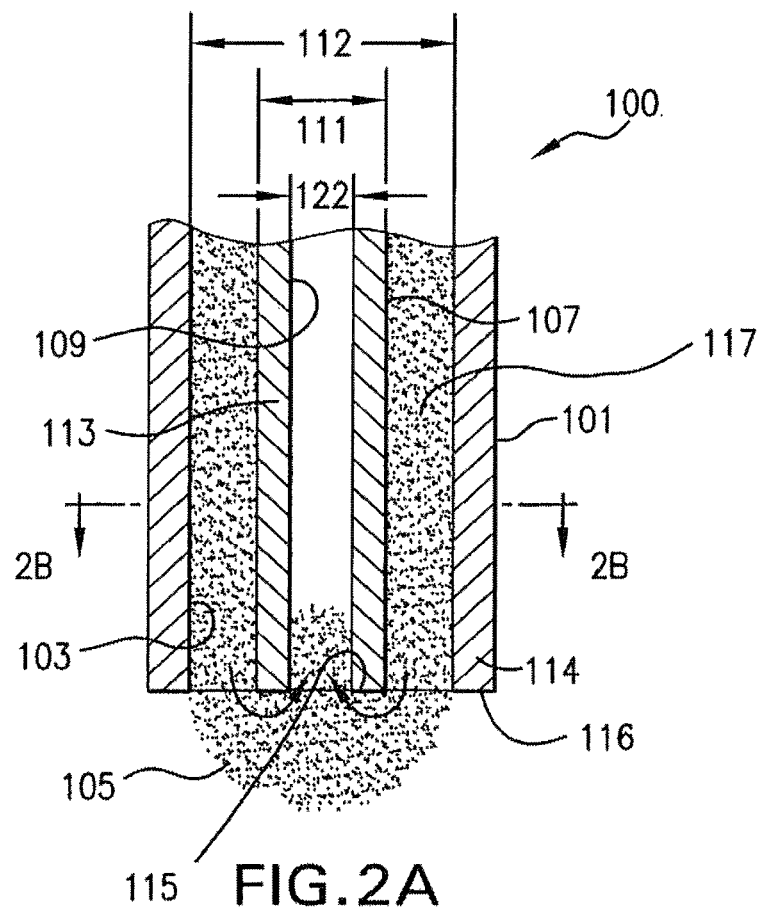
FIG. 2A illustrates a cross-sectional view of an apparatus for preparing immiscible-fluid-discrete-volumes, comprising a coaxial arrangement of tubes, and showing spacing fluid moving inside the inner tube of the coaxial tube arrangement.
Figure 2B:
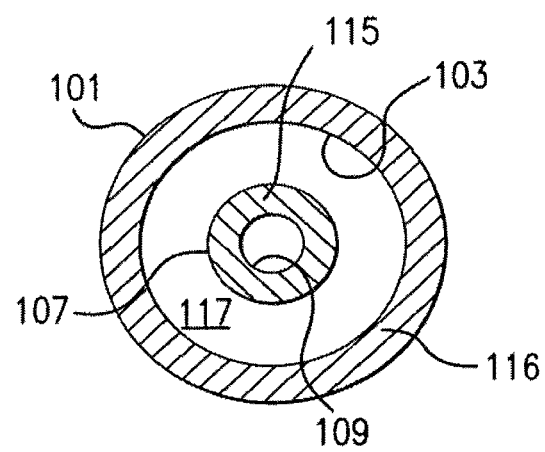
FIG. 2B illustrates another cross-sectional view taken along line 2A-2A of FIG. 2A.
Figure 6:
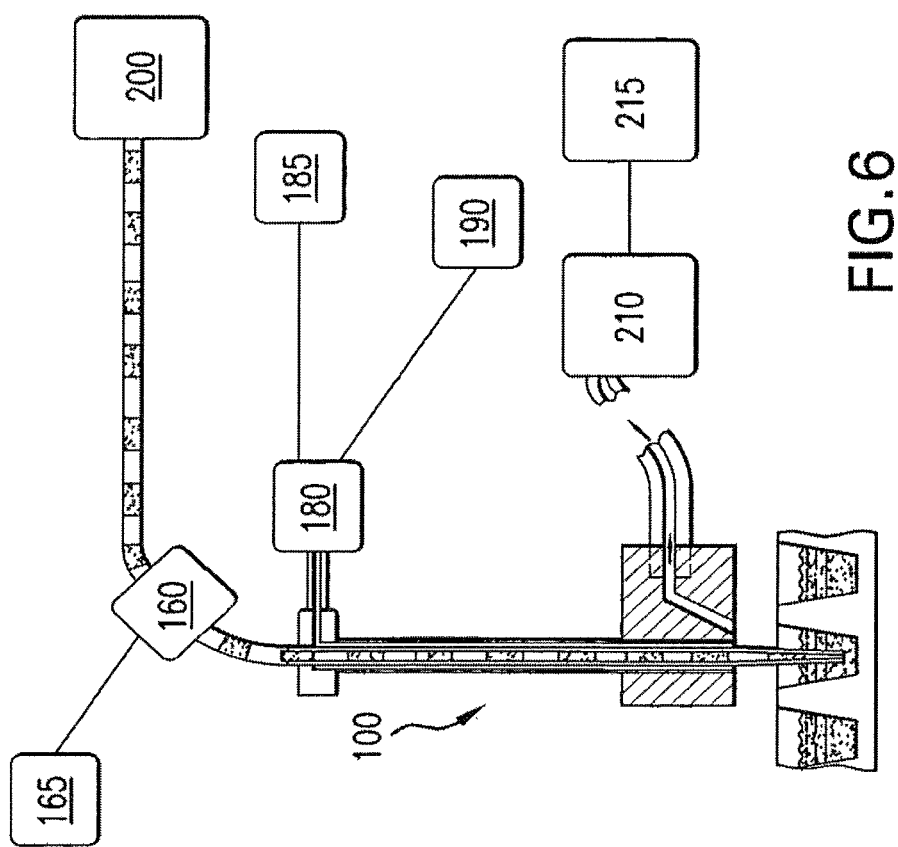
FIG. 6 illustrates a cross-sectional view of a system incorporating an apparatus of FIGS. 4A and 4B to generate immiscible-fluid-discrete-volumes for downstream sample processing as desired.

Apparatus 100 described in FIG. 2A can be adapted to be part of a sample preparation unit used as the front end portion of a system for DNA amplification and/or sequencing, as shown in FIG. 6, and/or of a system for carrying out other molecular biology or biochemical methods. In various embodiments, apparatus 100 can be adapted to deposit sample from a conduit into a container or onto a surface. The methods of interest can involve the use of small sample volumes. In various embodiments, small sample volumes can be from about 0.001 µl to about 10 µl. In other embodiments, small sample volumes of from about 0.01 µl to about 1 µl, or from about 0.02 µl to about 0.5 µl, can be generated.

A first pump 160 can be in fluid communication with inner tube 113 and pump 160 can be adapted to flow fluids, for example, aqueous immiscible-fluid-discrete-volumes spaced apart by a spacing fluid, through inner tube 113 in a first direction. A second pump 180 can be in fluid communication with outer tube 114, and pump 180 can be adapted to flow a fluid through outer tube 114 in a second direction opposite the first direction. In various embodiments, pump 160 can pump fluid from a container having an aqueous solution and pump 180 can pump fluid from a container containing a non-aqueous spacing fluid. In various embodiments, pumps 160 and 180 can be set in such a way that the pumping of fluids results in a stream of aqueous immiscible-fluid-discrete-volumes each separated from adjacent ones by the spacing fluid, and flowing through inner tube 113. One of skill in the art can determine the best way to accomplish this goal for a desired application. In various embodiments, it may be desirable to pump a liquid out of inner tube 113 such that the pumping direction can be reversed relative to the direction used for sample preparation, that is, relative to the direction used for aqueous immiscible-fluid-discrete-volume formation.

In various embodiments, the settings for the pumps can be based on appropriately adjusting the pump speeds of the pumps such that aqueous immiscible-fluid-discrete-volumes spaced apart by spacing fluid are produced in the inner tube. In other embodiments, controller 165 and 185 (see FIG. 6) can be adapted to actuate the pumps in such a way as to produce the desired spaced apart aqueous immiscible-fluid-discrete-volumes. In some embodiments, a computer can regulate actuation devices or directly regulate the pumps.

According to various embodiments, a pattern of spaced apart aqueous immiscible-fluid-discrete-volumes separated by spacing fluid can comprise aqueous immiscible-fluid-discrete-volumes containing a single target nucleic acid molecule in at least one or more of the aqueous immiscible-fluid-discrete-volumes. The immiscible-fluid-discrete-volume-forming conduit can comprise a capillary channel and the capillary channel can comprise a capillary tube. The immiscible-fluid-discrete-volume-forming conduit can comprise an appropriate material that permits ready flow of aqueous immiscible-fluid-discrete-volumes and spacing fluid through the conduit. According to various embodiments, the conduit can be different than a capillary tube, for example, the conduit can comprise a groove or a channel formed by opposing barriers or formed in a substrate.

Figure 3:
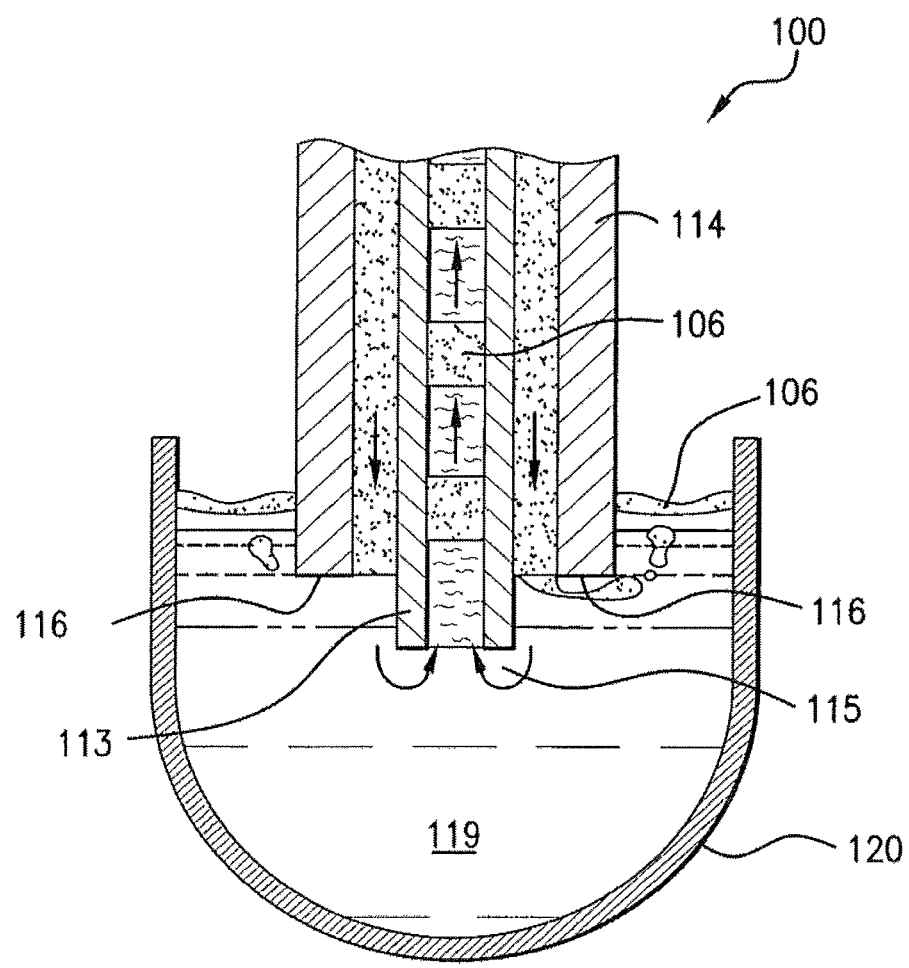
FIG. 3 illustrates a cross-sectional view of the end surface of the inner tube beyond the end surface of the outer tube of the apparatus whereby an aqueous immiscible-fluid-discrete-volume is formed in the inner tube adjacent spacing fluid that is already in the inner tube.

According to various embodiments, aqueous immiscible-fluid-discrete-volumes can be prepared using apparatus 100 shown in FIGS. 2A, 2B, and 3. Apparatus 100 can comprise an immiscible-fluid-discrete-volume-forming part at a beginning of a system. The system can comprise a spacing fluid pump unit 160 operatively connected to outer tube 114, a liquid pump unit 180 operatively connected to inner tube 113, a container (e.g., a sample tray 310 see, FIG. 4A) containing an aqueous liquid 312 (see FIG. 4A), and a control unit (165 and/or 185) adapted to control the flow in the inner tube 113 of the aqueous liquid and of the spacing fluid from the aqueous liquid container and the spacing fluid unit, respectively. The control unit can be adapted to actuate the pumps to pump volumes of aqueous liquid and spacing fluid that form aqueous immiscible-fluid-discrete-volumes spaced by spacing fluid, in inner tube 113. Each immiscible-fluid-discrete-volume can comprise an outer dimension equal to the maximum inner cross-sectional dimension of the immiscible-fluid-discrete-volume-forming conduit in which the aqueous immiscible-fluid-discrete-volumes are formed, as shown, inner tube 113, except for a layer of spacing fluid between the immiscible-fluid-discrete-volume and the tube (not shown for ease of depiction). In various embodiments, the aqueous liquid pump and the spacing fluid pump can comprise multiple devices in the system. Alternatively, any or all of the components of the system can be combined in a single device rather than being provided as separate units.

According to various embodiments, aqueous immiscible-fluid-discrete-volumes can form with a size and speed that is a function of at least one of several parameters that can include, but are not limited to, inner diameter 122 of inner tube 113, inner diameter 112 of outer tube 114, outer diameter 111 of inner tube 113, pumping pressure for each fluid, pumping rate for each fluid, the viscosity of each fluid, and the like parameters.

FIG. 3 illustrates apparatus 100 having inner tube 113 in a position to obtain an aqueous liquid 119 from aqueous sample container 120. In various embodiments, both the inner and outer tubes can be immersed in liquid 119. In other embodiments, outer tube 114 can remain at or above the surface of liquid 119 and inner tube 113 can be extend below the surface to obtain a portion of the liquid contained in the sample container.

Inner tube 113, which is shown containing aqueous immiscible-fluid-discrete-volumes separated by one another with non-aqueous spacing fluid, can be extended beyond end surface 116 of outer tube 114. With inner tube 113 extended, a volume of aqueous liquid sample that can form an aqueous immiscible-fluid-discrete-volume can be pumped into inner tube 113 adjacent to spacing fluid 106. It will be noted that spacing fluid 106 can continue to slowly flow from outer tube 114 during pumping or drawing of liquid 119 from aqueous sample container 120. After obtaining a portion of aqueous liquid 119, inner tube 113 can be withdrawn back into outer tube 114, thereby allowing inner tube 113 to suck in more spacing fluid 106, thereby creating an aqueous immiscible-fluid-discrete-volume. In various embodiments, apparatus 100 may be withdrawn from aqueous liquid 119 to enable spacing fluid 106 to encompass, surround, or otherwise bound the aqueous immiscible-fluid-discrete-volume. The process can be repeated until a sufficient number of aqueous immiscible-fluid-discrete-volumes, each separated by spacing fluid, are formed. In various embodiments, apparatus 100 can be left in container 120 to repeatedly create immiscible-fluid-discrete-volumes containing aqueous liquid 119. In various other embodiments, apparatus 100 can be repeatedly moved into different samples of a multi-sample sample holder, for example, a microliter plate. As such, multiple different sample portions can be obtained for analysis. Similarly, in some embodiments a sample holder can be moved relative to apparatus 100 such that apparatus 100 can remain stationary. After obtaining aqueous liquid, the tip of inner tube 113 can be rinsed with fresh spacing fluid and the spacing fluid used in rinsing can be removed, as illustrated in FIG. 4B.

According to various embodiments, two or more aqueous liquids can sequentially be drawn into inner tube 113 where they can merge together to form a single aqueous immiscible-fluid-discrete-volume containing the two or more liquids. As an example, a nucleic acid-containing sample can be drawn into inner tube 113, followed by a polymerase enzyme solution, followed by an aqueous mixture of nucleic acid bases, such that the resulting volume of aqueous liquid can be ready for a PCR reaction. The resulting volume can then be bound by spacing fluid subsequently drawn into inner tube 113, thereby creating an immiscible-fluid-discrete-volume ready for a PCR reaction.

Inner tube 113 can comprise polytetrafluoroethylene. According to various embodiments, materials other than polytetrafluoroethylene can be used to form the inner tube or the outer tube. The material can comprise, for example, one or more of silicone rubber, glass, butadiene rubber, other rubbers, nylon, other fluoropolymers, or polyethyleneterephthalate.

According to various embodiments, the tip of inner tube 113 can be rinsed between aqueous liquid drawing steps. A suction can be directly applied to outer tube 114 or can be applied to another tube or passageway that is located close to outer tube 114, and/or can be located in a block 300, as exemplified in FIG. 4B.

Figure 4A:
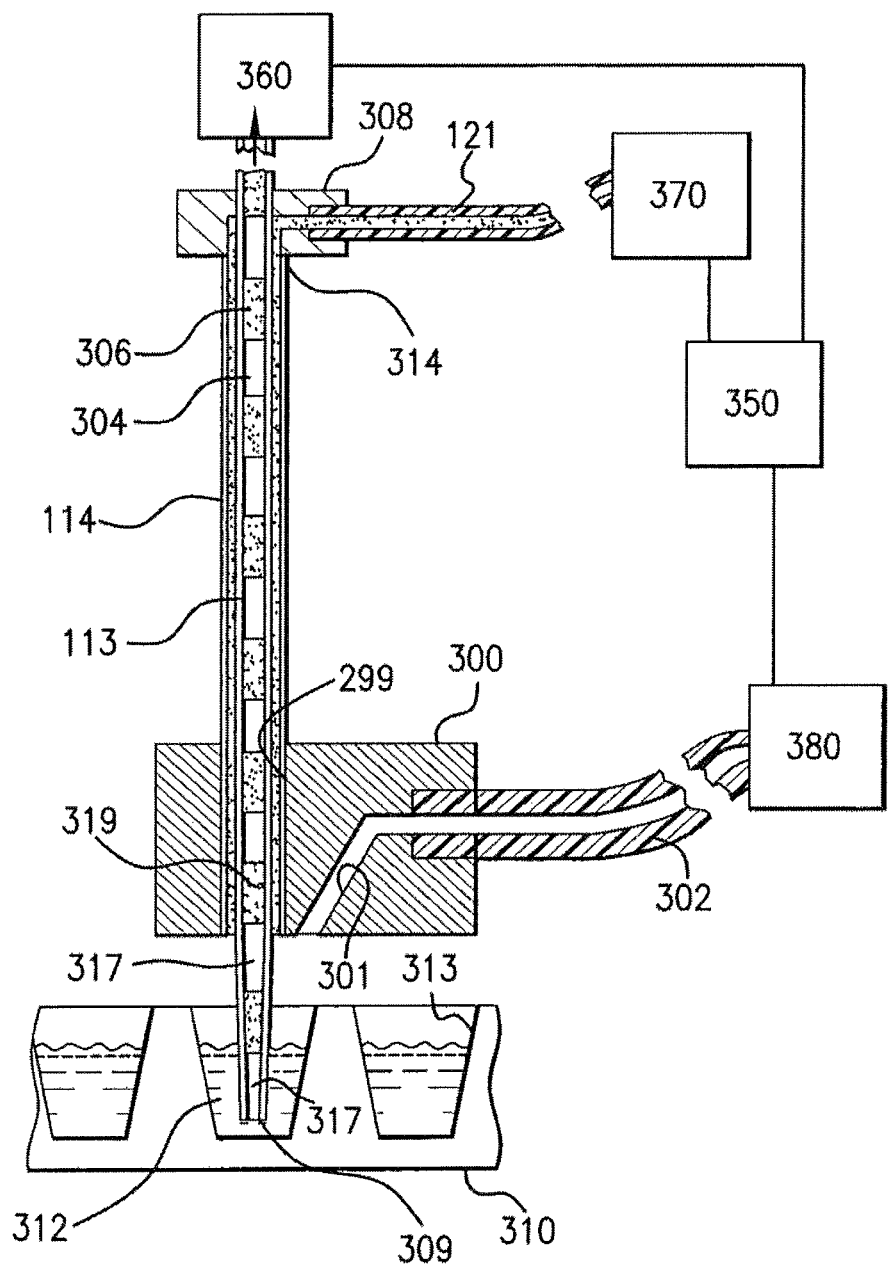
FIG. 4A illustrates a cross-sectional view of the inner tube positioned with its end surface beyond the end surface of the outer tube and a block that forms part of the tip rinsing apparatus.
Figure 4B:
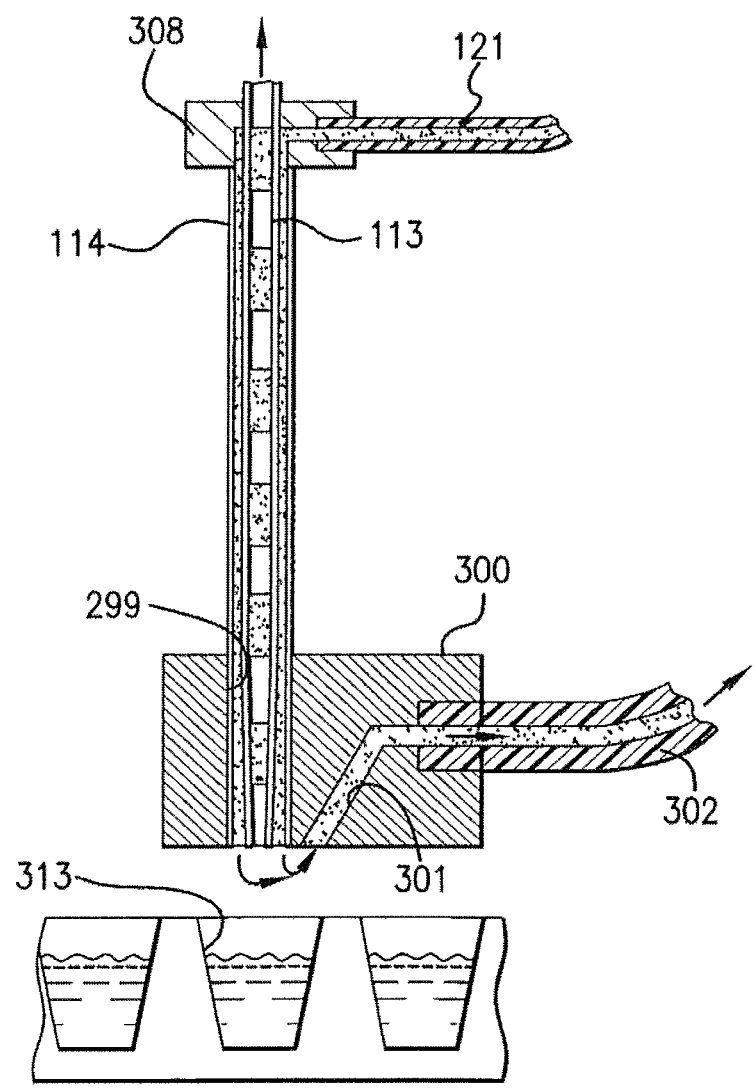
FIG. 4B illustrates a cross-sectional view of the inner tube positioned with respect to the outer tube such that the end surface of the inner tube is flush with the end surface of the outer tube, whereby the block can be used to rinse the conduit tip prior to the inner tube sucking up another sample.

FIGS. 4A and 4B illustrate an apparatus that can collect an aqueous liquid by removing an aqueous liquid from a well, rinse and/or clean the tip of the immiscible-fluid-discrete-volume-forming tube, and then introduce a spacing fluid into the immiscible-fluid-discrete-volume-forming tube after an aqueous liquid is collected. In such embodiments, an immiscible-fluid-discrete-volume-forming (inner) tube can be lowered into an aqueous liquid well. When the inner tube is lowered into the liquid well, a pump can suck or aspirate solution from the well into the inner tube. The inner tube can then be withdrawn from the aqueous liquid, by raising the tube individually, by raising the entire apparatus, or by lowering the aqueous liquid container. When the inner tube is removed from the aqueous liquid in the well, a solution from the outer tube can rinse-off the tip of the inner tube. For example, oil from the outer tube can be used to rinse-off the tip of the inner tube, and the rinse oil can be removed through a separate channel. The pumping arrangement can then be adjusted such that oil from the outer tube can be sucked into the inner tube, thereby forming aqueous immiscible-fluid-discrete-volumes in the inner tube, separated by spacing fluid. The process can then be repeated from the same well or from a different well in order to produce as many aqueous immiscible-fluid-discrete-volumes as desired.

As shown in FIG. 4A, the apparatus can contain aqueous immiscible-fluid-discrete-volumes 304 and non-aqueous spacing fluid 306 in inner tube 113. Aqueous immiscible-fluid-discrete-volumes 304 in inner tube 113 can be pumped to another portion of the system (as indicated by the arrow at the top of the figure) where processing and/or disposal of aqueous immiscible-fluid-discrete-volumes 304 and disposal of spacing fluid 306 can occur, for example, as shown in FIG. 6 and FIG. 5A, respectively. The aqueous immiscible-fluid-discrete-volumes can be pumped into a system for a reaction or hybridization, to a substrate, platform, or container for analysis or further processing, or into a waste container, as deemed appropriate.

The embodiment shown in FIGS. 4A and 4B depicts both an inner tube 113 and an outer tube 114 passing through a through-hole 299 in a block 300. It is to be understood, however, that in some embodiments through-hole 299 itself can serve as the outer conduit or outer tube of the apparatus, and in some embodiments a pump can be operatively connected directly to the through-hole 299.

According to various embodiments and as shown in FIG. 4B, block 300 can comprise a solid block having a through-hole formed therein for inner tube 113 and outer tube 114. The block can be made of any number of different materials. Any suitable material for forming passageways therein for fluids and/or for tubes going through the block can be used. The material should not react or should only very minimally react with any fluids flowing through the material. Exemplary materials for block 300 and for block 308 described below include plastic, polyethyleneterephthalate, polycarbonate, polytetrafluoroethylene, stainless steel, aluminum, glass, and the like. Surfaces of block 300 and block 308 that contact liquids can be coated with an inert, protective, and/or hydrophobic coating. In various other embodiments, block 300 and block 308 can each comprise more than one piece, rather than a monolithic block. As shown in cross-section, block 300 can comprise passageway 301 and tube 302 for directing waste fluids or other fluids to an appropriate location or container. In some embodiments, passageway 301 and tube 302 can be in fluid communication with a pump and a waste container. The direction of liquid flow is shown by arrows in the figure.

Block 300 can have a passageway portion extending therethrough that can permit inner tube 113 and outer tube 114 to pass therethrough. In some embodiments, inner tube 113 can move relative to outer tube 114 and block 300. In various embodiments, the tubes can remain stationary and block 300 can move relative to the tubes. In other embodiments, block 300 can remain stationary and both tubes move relative to block 300. In various embodiments, the arrangement of tubes and block 300 can be moved up and down relative to one or more liquid or sample containers.

In some embodiments, block 300 can be in an "up" position, relative to inner tube 113, as shown in FIG. 4A such that at least inner tube 113 extends beyond the edge of block 300. Alternatively, block 300 can be in a "down" position, relative to inner tube 113, as shown in FIG. 4B such that the end of inner tube 113 does not extend or only minimally extends beyond block 300. The "up" or "down" position can be accomplished either by moving the tubes relative to block 300, or by moving block 300 relative to the tubes.

As shown in FIGS. 4A and 4B, when block 300 is in the "up" position, sample liquid 312 from well 313 of sample tray 310 can be pumped into inner tube 113 to form a sample immiscible-fluid-discrete-volume. Inner tube 113 can then be withdrawn into outer tube 114 to permit spacing fluid 319 to enter inner tube 113, thereby separating sample immiscible-fluid-discrete-volumes 317 from one another. When inner tube 113 is withdrawn into outer tube 114, pumps in fluid communication with the tubes are pumping at an appropriate rate to allow immiscible-fluid-discrete-volume formation.

When block 300 is in a "down" position as shown in FIG. 4B, the pump in fluid communication with inner tube 113 can be shut off, and waste solution can flow through passageway 301 and out waste tube 302. In various embodiments, a pump can be in fluid communication with waste tube 302 in order to pump, for example, air and/or excess oil from outer tube 114, thereby rinsing contaminants, unwanted sample liquid, and/or reagent from end surface or tip 309 of inner tube 113.

According to various exemplary embodiments, tip 309 of inner tube 113 can be placed in sample liquid 312 in a well 313 of a sample tray 310. Exemplary sample trays can comprise microtiter plates, picotiter plates, 24-well plates, 96-well plates, 384-well plates, 1536-well plates, 6144-well plates, plates with removable sample vials, a card-type assay device, a flat surface, and array of vials, and the like. The pump that is operatively connected to, and in fluid communication with, inner tube 113 can suck aqueous liquid through tip 309 and into inner tube 113. Tip 309 of inner tube 113 can thereafter be withdrawn from contact with sample liquid 312. Withdrawal of tip 309 of inner tube 113 can be accomplished either by raising inner tube 113 into outer tube 114, resulting in the illustration shown in FIG. 4B, or by raising the entire apparatus 100 away from the sample.

When inner tube 113 is in the position shown in FIG. 4B, oil or another spacing fluid flowing out of outer tube 114 can rinse-off the end surface or tip of inner tube 113. The spacing fluid used as the rinse liquid can then be directed through passageway 301 in block 300 and be carried away to a waste station (not shown) operatively connected to waste tube 302. In some embodiments, a pump 380 (see FIG. 4A) can be connected to waste tube 302. In various embodiments (not shown) the entire length of passageway 301 can accommodate a tube such that block 300 has a liner therein for passageway 301. The positioning of the tubes relative to block 300 can be accomplished by keeping block 300 in a single position and moving the tubes relative to block 300, or by moving block 300 relative to the tubes, or by a combination of the two types of movements.

As shown in FIG. 4A, in some embodiments a control unit 350 can be provided that can independently control a plurality of pumps 360, 370, 380, for respectively flowing fluids through first conduit 113, second conduit 114, and waste tube 302. Pump 370 can be operatively connected to outer conduit 114 through a tube 121 connected to block 308.

As shown in FIGS. 4A, 4B, 5A, and 5B, apparatus 100 can comprise shroud or block 300 and a second block 308. Block 308 can form a structure that assists in supporting inner tube 113 and/or outer tube 114. Block 308 can comprise a through-hole passageway for inner tube 113 and for outer tube 114, or block 308 can comprise appropriate connections or bores to attach conduits such as capillary tubes to the block. The passageway can comprise an elbow 314 and openings 316 and 320 (See FIG. 5B). It will be recognized that the point of entry of inner tube 113 into outer tube 114 can be sealed to keep the contents of outer tube 114 from leaving outer tube 114 or block 308. Sealing can be accomplished with appropriate boring and/or counter-boring, and/or using a sleeve, bearing, sealing gasket, O-ring, or the like, where appropriate.

According to various embodiments, elbow in block 308 may not necessarily contain outer tubing 114. Instead, outer tubing 114 can be connected to block 308 via an appropriate connection, for example, via a bore 330 in block 308. At opening 320, outer tube 114 can also be connected such that fluid can move from outer tube 114, into block 308, and into tube exiting block 308. Thus, only inner tube 113 actually passes through block 308 in the embodiment depicted.

In order to accomplish a desired result, for example, rinsing the tip of tubes used for obtaining a volume of sample liquid, a control unit 350 (see FIG. 4A) can be used for regulating appropriate flow rates and appropriate starting and stopping of the pumps in fluid communication with inner and outer tubes. Such a controller can control an actuator for turning the pumps on and off as desired. The controller can comprise a computer. Appropriate pump speeds and actuations of the pumps can be determined to accomplish the removal of waste from the tip of inner tube 113.

According to various embodiments, a method is provided that comprises: pumping a first fluid in a first direction in a space between an outer perimeter of a first conduit and an inner perimeter of a second conduit; drawing the first fluid past an end surface of the first conduit, and into the first conduit in a second direction that is opposite the first direction; and positioning the first conduit into a receptacle containing a second fluid that is immiscible with the first fluid, and drawing at least a portion of the second fluid into the first conduit. In some embodiments, the method further comprises, before positioning into the receptacle, positioning at least one of an end surface of the first conduit and an end surface of the second conduit such that the end surface of the first conduit is beyond the end surface of the second conduit. In some embodiments, the method comprises, after drawing at least a portion of the second fluid, positioning at least one of the first conduit and the second conduit such that the end surface of the first conduit can either be flush with the end surface of the second conduit or inside the second conduit. In some embodiments, the second conduit can comprise a block having a through-hole, and positioning at least one of the first conduit and the second conduit can comprise moving the end surface of the first conduit into the through-hole. In some embodiments, the method can further comprise, after drawing at least a portion of the second fluid into the first conduit, rinsing the end surface of the first conduit with the first fluid.

According to various embodiments, waste, for example, spacing fluid between adjacent sample immiscible-fluid-discrete-volumes, can be removed. As the spacing fluid comes out of the tip 309 of inner tube 113, outer tube 114 can have a suction applied to it and any unwanted spacing fluid sample immiscible-fluid-discrete-volumes can be removed.

Figure 5B:
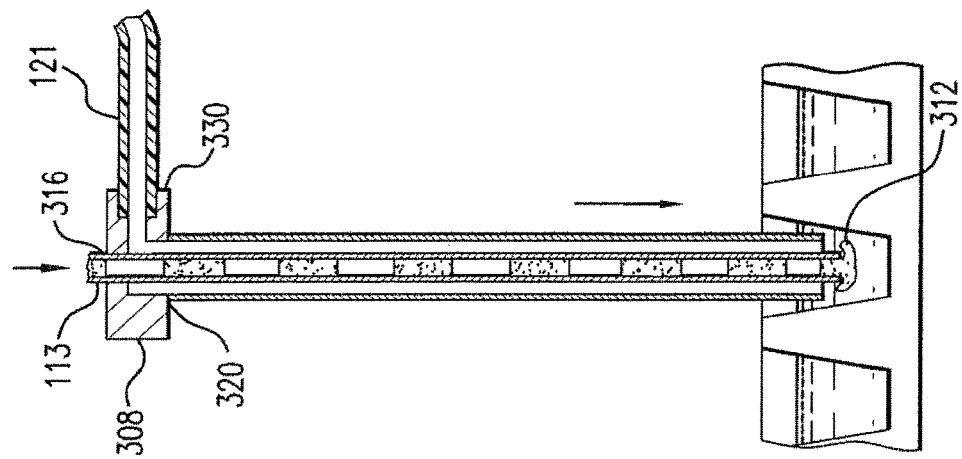
FIG. 5B illustrates a cross-sectional view of using the apparatus to deposit a sample in a sample well.
Figure 5A:
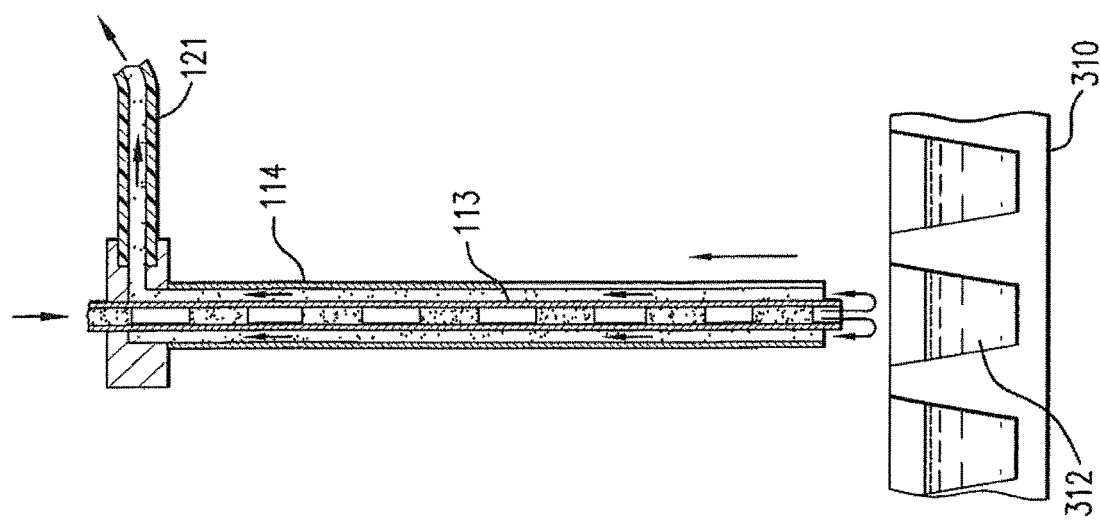
FIG. 5A illustrates a cross-sectional view of removal of waste material.

FIGS. 5A and 5B illustrate an embodiment for removing waste from an inner tube 113 and/or for depositing desired samples in a container. For such a usage the apparatus can be placed at the back-end of a system, such that already prepared immiscible-fluid-discrete-volumes can be "spit out" from the inner tube and waste can be sucked away through the outer tube. In such usage, pumping of immiscible-fluid-discrete-volumes and/or other solutions can occur in different directions than shown in FIGS. 4A and 4B. In various embodiments, the apparatus can first be used to obtain sample immiscible-fluid-discrete-volumes spaced from one another by spacing fluid, and then a similar apparatus on the back-end of the system can have reverse pump directions such that sample immiscible-fluid-discrete-volumes and/or spacing fluid can be "spit out" either collected or sent to a waste receptacle.

In the "up" position shown in FIG. 5A, waste can be sent to a waste container. In the down position shown in FIG. 5B, a desired sample immiscible-fluid-discrete-volume can be deposited in a desired container. In the down position, suction normally being applied to outer tube 114 may be stopped or sufficiently slowed down such that the desired sample immiscible-fluid-discrete-volume can be deposited in an appropriate sample well.

According to various embodiments, the downstream processes can be carried out in a capillary channel, for example, a capillary tube. The capillary tube can be in fluid communication with apparatus 100 as shown in FIG. 6. An exemplary capillary tube that can be used can have an inner diameter of about 1000 microns or less. In other embodiments the inner diameter can be about 300 microns or less, for example, about 100 microns or less, or about 50 microns or less. Other embodiments can involve methods that use a capillary tube having an inner diameter that is greater than about 300 microns, for example, from about 500 microns to about 1000 microns, or about 500 microns or less. In various embodiments, the above dimensions can refer to the maximum cross-sectional dimension of the capillary channel. Such a channel can be rectangular in shape or have any other suitable shape. Various systems and apparatus can also be provided that include such a capillary channel.

FIG. 6 illustrates a system that can use one or more embodiments of apparatus 100. In various embodiments, aqueous immiscible-fluid-discrete-volumes spaced apart by spacing fluid are prepared in apparatus 100. A pump 160, control unit 165, pump 180, control unit 185, spacing fluid source 190, can be used to prepare the aqueous immiscible-fluid-discrete-volumes. The aqueous immiscible-fluid-discrete-volumes can then also be pumped to the rest of the system 200 with pump 160. In some embodiments, the rest of the system represented by the black box designated 200 can comprise a system as shown and described in U.S. Provisional Patent Application No. 60/710,167, filed Aug. 22, 2005, which is incorporated herein in its entirety by reference, or any of the immiscible-fluid-discrete-volume processing systems described and shown herein. A pump 210 can be operatively connected to waste tube 208. Pump 210 can be controlled by a control unit 215, and control unit 215 can be operatively connected to one or more other control units in the system.

In some embodiments, a method is provided that can comprise using the system described herein to process an aqueous immiscible-fluid-discrete-volume. According to various embodiments, the method can comprise amplifying at least one target nucleic acid sequence, for example, in a processing conduit downstream of the immiscible-fluid-discrete-volume-forming inner conduit described above. According to various embodiments, the method can comprise introducing polymerase chain reaction inactivating reagents into a processing conduit, for example, a capillary channel, after amplifying the at least one target nucleic acid sequence and before subjecting the nucleic acid sequence to a sequencing reaction. The reagents can be used to inactivate or remove or eliminate excess primers and/or dNTP's resulting from or leftover from an amplification process. The inactivating reagents can be introduced at a junction in the processing conduit, for example, after an aqueous sample immiscible-fluid-discrete-volume to be inactivated is aligned with the junction. The junction can comprise, for example, a T-junction or a Y-intersection.

According to various embodiments, one or more target nucleic acid sequences can be subjected to a sequencing reaction to form a detectable product, and the method can comprise detecting the detectable product. In various embodiments, the detectable product can be detected inside the same processing conduit or capillary channel where the detectable product is formed. In other embodiments, the detectable product can be transferred out of the processing conduit and detected using, for example, using a flow cell or a capillary electrophoretic sequencer. In various other embodiments, an off-capillary detector can be used as deemed appropriate.

According to various embodiments, the method can comprise attaching an amplicon to an inner wall of a processing conduit or capillary channel to form an attached amplicon and flowing at least one sequencing reaction primer into the processing conduit such that the sequencing reaction primer reacts with the attached amplicon in the processing conduit. In various embodiments, a double stranded amplicon can be denatured, primers can be hybridized, and a sequencing reaction can be conducted. In other embodiments, all reactions can be done in a single mixture of reagents. Intercalating dyes for detection by a detector can be added as deemed appropriate either before or after denaturation.

According to various embodiments of the present teachings illustrated, for example, in FIG. 7, a plurality of tubes 710, 712, 714, 716, and 718, can be connected to, or otherwise be in fluid communication with, a manifold 720 at a plurality of respective openings 722, 724, 726, 728, and 730. While tubes 710, 712, 714, 716, and 718 are shown terminating at manifold 720 and in fluid communication with respective passageways in manifold 720, it is to be understood that the tubes can, in some embodiments, extend into manifold 720. For example, instead of the arrangement shown in FIG. 7, tubes 712, 714, and 716 can be inserted into bores formed in manifold 720 and which extend all the way to respective junctions with immiscible-fluid-discrete-volume-forming channel 756, or closely adjacent to immiscible-fluid-discrete-volume-forming channel 756. Manifold 720 is shown in cross-section and tubes 710, 712, 714, 716, and 718 are depicted as transparent, although they do not have to be, so that the oil and reagents therein can be seen in the drawing. Tube 718 can be transparent in some embodiments such that a reaction involving an aqueous immiscible-fluid-discrete-volume inside the tube can be detected. In the embodiment shown in FIG. 7, tube 710 is shown as a feed tube that supplies oil 732 to manifold 720. Oil 732 can be moved from an oil supply unit 734 comprising, for example, a supply of oil and a pump, into and through tube 710. Oil supply unit 734 can comprise a syringe pump, a reciprocating pump, a cylinder pump, a peristaltic pump, or the like. A control unit (not shown) can be provided to control the pressure exerted by oil 732 as it is moved through immiscible-fluid-discrete-volume-forming channel 756. According to the various embodiments, manifold 720 can comprise a fluorocarbon material, for example, a perfluorocarbon material such as polytetrafluoroethylene. In some embodiments, manifold 720 can comprise the same material as is used for the tubes 710, 712, 714, 716, and/or 718, or other materials known to those skilled in the art. Materials can be selected that are non-reactive or minimally reactive with the liquids passing through manifold 720.

According to various embodiments, tube 710 can be connected to manifold 720 by any appropriate connection, for example, using a fitting or connector that extends from manifold 720, by frictionally fitting tube 710 into a bore formed in manifold 720 wherein the bore has an inner diameter that is about equal to the outer diameter of tube 710, or by using an adhesive, or the like. Similarly, tubes 712, 714, 716, and 718, can be connected to manifold 720.

In the embodiment shown, tube 712 is connected at a first end to manifold 720 and at an opposite, second end to a first reagent supply unit 736. First reagent supply unit 736 can comprise, for example, a supply of a first reagent 738 and a pump for moving first reagent 738 into and through tube 712. First reagent 738 can comprise, for example, samples, primers, or other reagents such as SAP, or other solutions or reagents. First reagent supply unit 736 can comprise a pump of the same type, or of a different type, as the type used for oil supply unit 734. A control unit (not shown) can be provided to control the pressure exerted by the movement of first reagent 738. In some embodiments, the control unit can control the pressure independently of the other supply units in the system.

A tube 714 can be connected at a first end to manifold 720 and at a second, opposite end, to a second reagent supply unit 40. Second reagent supply unit 740 can comprise, for example, a supply of a second reagent and a pump for moving the second reagent 742 into and through tube 714. Second reagent supply unit 740 can comprise a pump that can be the same type as, or different than, the type of pump used in oil supply unit 734. A control unit (not shown) can be provided to control the pressure exerted by the movement of second reagent 742.

A tube 716 can be connected at a first end to manifold 720 and at a second, opposite end to a third reagent supply unit 744. Third reagent supply unit 744 can comprise, for example, a supply of a third reagent 746 and a pump for moving third reagent 746 into and through tube 716. The pump can be the same type as, or different than, the type of pump used for oil supply unit 34. A control unit (not shown) can be provided to control the pressure exerted by the flow of third reagent 746 in tube 716.

According to various embodiments, first reagent 738, second reagent 742, and third reagent 746, can each comprise an aqueous medium, for example, an aqueous solution, and each can be miscible with the other two reagents. In some embodiments, each of first reagent 738, second reagent 742, and third reagent 746, can be immiscible with oil 732. As such, as the first reagent 738, second reagent 742, and third reagent 746 pass through passageways 750, 752, and 754, respectively, and merge into immiscible-fluid-discrete-volume-forming channel 756 in the body of manifold 720 to create distinct, separate, and spaced apart aqueous immiscible-fluid-discrete-volumes 760, 762, and 766 divided from one another by oil 732 in the form of immiscible-fluid-discrete-volumes, for example, the aqueous immiscible-fluid-discrete-volumes can be separated by oil or another spacing fluid such as depicted by reference numeral 758. It is to be understood that additional tubes can be connected to additional respective passageways (not shown) if it is desired to provide such additional features in a system.

An outlet from manifold 720 can be provided at opening 730 and can be connected to tube 718, for example, using a connection as described above. In an exemplary embodiment, tube 718 is connected by a first end to manifold 720, and at a second, opposite end, to a collection unit 764 where the immiscible-fluid-discrete-volumes 760, 762, and 766 can be processed, detected, or otherwise manipulated, analyzed, and/or transferred to another device or system.

According to various embodiments, the system shown in FIG. 7 can comprise a single pump and a valving scheme that replaces the four individual pumps described above in connection with units 734, 736, 740, and 744. In some embodiments, the fluidic usage of each of the reagents can be substantially the same, and the flow resistance of the reagents can be substantially the same.

In various alternative embodiments relative to the embodiment shown in FIG. 7, the system can be provided with an alternating immiscible-fluid-discrete-volume supply unit that can generate and/or move aqueous-based immiscible-fluid-discrete-volumes spaced apart from one another by a spacing fluid, into and through tube 710, instead of an oil supply unit. The spaced-apart immiscible-fluid-discrete-volumes comprise aqueous immiscible-fluid-discrete-volumes spaced by spacing fluid, although the system can be used for moving spaced-apart immiscible-fluid-discrete-volumes of any fluid in an immiscible spacing fluid. The aqueous immiscible-fluid-discrete-volumes can comprise for example, a biological sample and/or reaction components or reagents for treating a biological sample. In some embodiments a biological sample can be provided in an immiscible-fluid-discrete-volume, which comprises a single target molecule, for example, a single DNA molecule without duplicate or replicate copies. In some embodiments, the aqueous immiscible-fluid-discrete-volume can comprise one or more components for carrying out a reaction involving DNA, for example, one or more components for performing a polymerase chain reaction or a sequencing reaction. According to various embodiments, primers can be introduced as input, samples can be added to those primers, or samples can be introduced as input and primers added to those samples. In some embodiments, samples and primers can be added in any desired combination, or combined or added at the same time, then injected.

While the methods described in conjunction with FIG. 7 involve introducing each of the first, second, and third reagents, it is to be understood that the control units described herein can be used to control the introduction of one, two, or all three, of those reagents. For example, if it is desired to introduce only the second reagent to immiscible-fluid-discrete-volume forming channel 756, the control units for supply units 736 and 744 can control those units not to introduce the first and third reagents to immiscible-fluid-discrete-volume forming channel 756.

The various reagents, mixtures, samples, oils, and other fluids and liquids that can be used with or moved through the systems described herein include those fluids and liquids described in detail in U.S. Provisional Patent Application No. 60/710,167 entitled "Sample Preparation for Sequencing," to Lee et al., filed Aug. 22, 2005, and in U.S. Provisional Patent Application No. 60/731,133 entitled "Method and System for Spot Loading a Sample," as well as those of Schroeder et al., filed Oct. 28, 2005 cited herein, each of which is incorporated herein in its entirety by reference.

The apparatuses, systems, and/or methods described herein can provide flexibility in the generation of immiscible-fluid-discrete-volumes. The generated immiscible-fluid-discrete-volumes can be used in or driven into various microfluidic formats. One can, for instance, integrate the immiscible-fluid-discrete-volume formation into a card format, where multiple inlet ports can feed the manifold for delivery to a reaction plate or other receptacle. In various embodiments, microsized tubes or capillaries can be connected to a larger size port and one can pipette reagents into the ports to create new immiscible-fluid-discrete-volumes or add reagents to existing immiscible-fluid-discrete-volumes. The card can, for example, be cast, etched, molded, hot-stamped, pressed, formed of Su8 photo-1 orthographically, and can be fabricated of plastic, glass, or other material.

According to various embodiments, different approaches or mechanisms can be used to pump or drive liquid into the manifold. According to various embodiments, the system can comprise individual syringes to drive each liquid into the immiscible-fluid-discrete-volume-forming channel. A consideration in this regard can be the number of liquids to be introduced, in the case when a large number of samples are to be introduced into a tube. Another approach can be to use only one pump which communicates with one or more valves that regulate the opening, closing, and/or diversion of channels or liquids in channels. Another method to pump or transport liquids through the manifold can involve applying pressure to the various tubes, for example, by compressing or pinching the tubes with rollers to press the tubes down. As a roller is moved along the tube the pinching action of the tube can be used to push liquid into or out of the manifold. According to various embodiments, pressure can be applied by other members than rollers, such as flat pressers or others. According to various further embodiments, pumping or driving action can be achieved with techniques other than direct mechanical pressure, including, for example, magnetohydrodynamic, electrophoretic, electrowetting, or other force.

Pumping and routing techniques, according to various embodiments of the present teachings, can eliminate the need for re-dipping a tube tip into different supply or other wells. This in one regard can minimize contamination. In various embodiments, the disclosed techniques can be performed in a totally enclosed, vacuum-sealed or otherwise isolated system, such that the introduction of air bubbles can be avoided.

The apparatuses, methods, and/or systems provided herein can be used for liquid delivery to a collector tube, or other common channel tube, using an appropriate liquid pushing, driving, moving, or pumping device or mechanism. This technique can be used for protocols that require delivery of multiple individual small liquid volumes to a common channel, for example, variant sequencing, real time PCR, and/or genotyping.

In various embodiments, discrete volumes of a first liquid, for example, an aqueous liquid, which is immiscible with a second liquid, for example, an oil, can be generated according to a variety of sipping or other liquid aspirating techniques. As shown in FIG. 8, and according to various embodiments, the sipping or aspiration can be produced by using a syringe pump 810 to pull or draw from a well 830 a desired liquid into a tube 820 or other channel or conduit, using negative pressure. Tube 820 can initially be completely filled with one of the liquids, for example, oil, and liquid pulled from one end of tube 820 can cause a suction that can then pull or draw liquid into the other end of tube 820.

According to various embodiments, another approach to effect sample sipping can be to generate a positive pressure between the liquid in well 830, or other container or vessel, and the end of tube 820 that is not in well 830. This can be accomplished by positively pressurizing well 830 which contains the liquid to be aspirated while keeping the other end of tube 820 that is not in the liquid in well 830 at a lower pressure, for example, at atmospheric pressure. Another technique can be to maintain atmospheric pressure in well 830 while applying vacuum to the end of tube 820 that is not in well 830, or otherwise applying differential pressure across tube 820 and well 830. According to various embodiments, alternating, interleaved, or other sequences of liquids can thereby be aspirated to generate a set 840 of discrete volumes of at least a first immiscible liquid. According to various embodiments, a pump can be operatively connected to, and inline with, tube 820.

In various embodiments, it is desirable to minimize evaporation of an aqueous liquid that is to be drawn into an immiscible-fluid-discrete-volume-forming tube. According to various embodiments, for example, as shown in FIGS. 9A and 9B, a well 930, from which an aqueous liquid 934 is to be aspirated, can be provided with a thin layer 950 of oil on top of aqueous liquid 934, and of sufficient volume to cover the surface of aqueous liquid 934 in well 930. Such a covering layer 950 of oil can reduce the evaporation of aqueous liquid 934. Another technique to reduce evaporation is to generate a continuous oil overlay 951 across a number of wells. If the thickness of the continuous oil overlay 951 is greater than the vertical distance the immiscible-fluid-discrete-volume-forming tube tip rises above the surface of the aqueous fluid, the tip never comes into contact with air as it is moved from one well to another well, thereby reducing the chance of air bubble entrapment, and preventing splashing and resultant cross-contamination in the immiscible-fluid-discrete-volume-forming tube. This also provides the option of pulling oil or other spacing fluid into the tube during the time the tube is moved from one reagent to another, speeding up processing.

According to various embodiments involving formation of immiscible-fluid-discrete-volumes by aspiration, a method is provided using a system whereby introduction of air bubbles in an immiscible-fluid-discrete-volume-forming tube is prevented. Bubbles can be suppressed by designing a system that maintains the immersion of an introduction end or tip of an immiscible-fluid-discrete-volume-forming tube in a liquid. According to various embodiments, the amount of liquid that actually enters into the tube can be dependent on the surface properties and the dimensions and shape of the tube.

According to various embodiments, a method to generate a set 840 of immiscible-fluid-discrete-volumes by sipping or aspirating from alternating containers or wells 830 containing aqueous sample fluid and oil is presented. As shown in FIG. 8, tip 818 of tube 820 can be immersed in a liquid to aspirate a specified amount of the liquid from one or more wells 830. Alternating aspiration between aqueous and oil wells can generate a set 840 of aqueous-discrete-volumes comprising alternating aqueous immiscible-fluid-discrete-volumes and separated by oil in tube 820. This method can work with oil that is lighter or heavier than, or the same weight or density as, the aqueous liquid. This technique can also incorporate a lighter oil layer on the top of an aqueous liquid to prevent evaporation, as for example shown in FIGS. 9A and 9B. In an exemplary embodiment, the heavier or bottom oil can comprise, for example, a fluorinated oil such as FC-40, available from 3M Corporation, Minneapolis, Minn., while the light oil overlay 950 can comprise PDMS 5 cSt, available from Sigma Aldrich, St. Louis, Mo.

According to various embodiments, a set 840 of aqueous-discrete-volumes can be generated by sipping aqueous and oil liquids from the same tube or well 1030, as shown in FIGS. 10A and 10B. Set 840 of aqueous-discrete-volumes can be generated by alternate aspiration of the aqueous and the oil liquids. In various embodiments, alternate aspiration can be performed, for instance, by placing an immiscible-fluid-discrete-volume-forming tube 820 (FIG. 8) at different depths within a well 1030 (FIGS. 10A-10D) to aspirate different liquids from different zones of the same well. The relative densities of the liquids can determine which liquid is at the top, middle, bottom, or other, position. For an aqueous liquid with perfluorinated FC-40 oil, for example, the aqueous liquid will be the top phase. By using an oil lighter than the aqueous liquid, for example, PDMS oil, the oil phase can be the top phase. This method works with an oil layer in each tube or a continuous oil overlay as variously shown in, for instance, FIGS. 9A, 9B, and 10A-10D.

According to various embodiments, and as shown in FIGS. 10A-10D, immiscible-fluid discrete volumes can be generated by manipulating the end of an immiscible-fluid discrete-volume-forming tube within the wells 1030 depicted. For example, the introduction end of an immiscible-fluid discrete-volume-forming tube can be inserted into an open upper end 1032 of a well 1030 and manipulated to draw-in a first liquid, for example, an aqueous sample fluid 1034, and a second liquid that is immiscible with the first liquid, for example, an oil 1036, alternately. In some embodiments, the tip of the immiscible-fluid discrete-volume-forming tube can be raised and lowered alternately so that it contacts the aqueous sample fluid and oil, alternately, within well 1030. In some embodiments, the tip of the immiscible-fluid discrete-volume-forming tube can be stationary and well 1030 can be raised and lowered to position the tip in the aqueous sample fluid and oil, alternately. As shown in FIG. 10A, oil 1036 has a higher density than aqueous sample fluid 1034. In the embodiment shown in FIG. 10B, a lighter oil 1050 covers aqueous sample fluid 1034, and aqueous sample fluid 1034 floats on top of heavier oil 1036.

In some embodiments, such as those shown in FIGS. 10C and 10D, a plurality of wells 1030 can be positioned in a receptacle 1040 provided with a respective plurality of through-holes 1042. In each through-hole 1042 is provided a well 1030, for example, a vial well as depicted in FIGS. 10A and 10B. Instead of through-holes, in some embodiments the receptacle can comprise recesses (not shown) in which wells 1030 can be disposed and the receptacle can be free of through-holes. In the embodiment shown in FIGS. 10C and 10D, through-holes are used to receive wells 1030 and through-holes comprise open upper ends that intersect with bottom wall 1046 of a recess 1044 formed in receptacle 1040. As shown in FIG. 10C, each well 1030 can be provided with an aqueous sample fluid 1034 disposed therein, and after all wells 1030 are placed in respective through-holes 1042, a layer of a sealing fluid 1050 can be introduced into recess 1044 until the level of the sealing fluid 1050 rises above the open upper ends of wells 1030 and flows into wells 1030. As such, sealing fluid 1050 can seal the aqueous sample fluids in wells 1030 thereby preventing evaporation and contamination of the aqueous sample fluids. In some embodiments, the sealing fluid can comprise an oil, for example, mineral oil or a polydimethylsiloxane oil, that is immiscible with the aqueous sample fluids. As shown in FIG. 10C, sealing fluid 1050 can be filled into recess 1044 until a level is attained that rises above open upper ends 1032 of wells 1030 and a continuous sealing overlay is provided.

As shown in FIG. 10D, where reference numerals which are the same as those shown in FIG. 10C represent the same features as described with reference to FIG. 10C, each well 1030 contains both a heavier or more dense oil 1036 at the bottom thereof and a lighter or less dense aqueous sample fluid 1034 floating on top of oil 1036. In the embodiment shown in FIG. 10D, lighter oil, used as a sealing fluid 1050, covers open upper ends 1032 of wells 1030 to seal wells 1030 with aqueous sample fluids 1034 and oil 1036 therein. As in the embodiment shown in FIG. 10C, lighter oil can be used to prevent evaporation of aqueous sample fluids 1034 and to prevent contamination of wells 1030.

As depicted in FIG. 11, receptacles 1040 such as shown in FIGS. 10C and 10D can be in the form of a substrate 1156. As depicted in FIG. 11, a recess can be provided in substrate 1156 in the form of a trough 1160. As depicted in FIG. 11, through-holes 1042 shown in FIGS. 10C and 10D can be in the form of through-holes 1158 intersecting with the bottom wall 1162 of trough 1160. Substrate 2 can comprise, for example, polytetrafluoroethylene, other polymeric, polyolefinic, or other non-reactive or inert material. For example, as shown in FIG. 11, wells such as 0.2 ml PCR tubes can be inserted into through-holes 1158 in trough 1160. A light sealing fluid, for example, a light oil, can then be added to trough 1160 until a level is achieved that forms a continuous oil overlay covering the open upper ends of wells disposed in through-holes 1158. In some embodiments, the oil liquid overlay can be as deep as trough 1160 formed in substrate 1156. The continuous overlay can be useful in preventing evaporative loss of the aqueous sample fluid and reducing or eliminating the risk of contamination. An immiscible-fluid-discrete-volume-forming tube distal tip positioning unit can be provided to maneuver an intake tip of an immiscible-fluid-discrete-volume-forming conduit into one or more different wells held in trough 1160 of substrate 1156. The positioning unit can comprise appropriate servomotors or another translation device to affect movement of the intake tip. The positioning unit can be designed for controlled movement in one, two, three, or more directions. The continuous overlay can be made deeply enough such that the distal tip of the immiscible-fluid-discrete-volume-forming conduit can be moved from well to well without ever having to rise above and out of the overlay. As a result, the immiscible-fluid-discrete-volumes formed can be free of air bubbles and contamination. It will be obvious to one skilled in the art that the relative motion required to bring the distal tip into contact with a particular liquid can be accomplished by moving only the intake tip, as described above, or only substrate 1156, or both the intake tip and substrate 1156.

According to various embodiments of the present teachings, the ability to independently control the amount of liquid to be aspirated offers the flexibility of generating different immiscible-fluid-discrete-volume sizes. As a result of immiscible-fluid-discrete-volume preparation according to various embodiments, various immiscible-fluid-discrete-volume sizes can be generated.

According to various embodiments, a rinse station can be provided for rinsing off the intake tip of an immiscible-fluid-discrete-volume-forming conduit, for example, before and/or after each aqueous volume uptake procedure and/or or spacing fluid uptake procedure. In the embodiment depicted in FIGS. 12A and 12B, a system 1200 can be provided with a rinse station comprising an artesian well 1202. While a rinsing well is depicted in FIGS. 12A and 12B, it is to be understood that other rinsing devices can be instead be provided to rinse off the intake tip of an immiscible-fluid-discrete-volume-forming conduit between uptake procedures. Ultrasonic cleaning stations and pressurized fluid spray stations can be among alternatives that can be used instead of a rinsing well station as depicted.

As shown in FIGS. 12A and 12B, system 1200 can include an intake tip positioning unit 1204 that can be provided with appropriate drive means to move an intake tip 1300 in three dimensions, for example, along an X axis, along a Y axis, and along a Z axis. Positioning unit 1204 can be programmed and/or manipulated to move intake tip 1300 into contact with various fluids retained in a sample tray 1222. For example, sample tray 1222 can be provided with multiple wells 1224 that can each independently retain an aqueous sample, an aqueous solution or mixture of reagents, a combination thereof, or a spacing fluid. Sample tray 1222 can be removably mounted on a platform 1230 onto which artesian well 1202 can also be mounted.

During an immiscible-fluid-discrete-volume-forming procedure, positioning unit 1204 can position intake tip 1300 in a first well 1224 of sample tray 1222 and negative pressure from a source can be applied to the interior of intake tip 1300 to result in the uptake of a first fluid. Then, positioning unit 1204 can move intake 1300 to artesian well 1202 to rinse off intake tip 1300 before positioning unit 1204 moves intake tip 1300 into a different well of sample tray 1222 to uptake a second, different fluid that can be miscible or immiscible with the first fluid.

System 1200 can be provided with a rinse fluid supply unit 1206 comprising a pump and a conduit 1220 for delivering a rinse fluid to and through a central orifice 1232 of artesian well 1202. As rinse fluid supply unit 1206 forces rinse fluid through orifice 1232, the rinse fluid spills over an upper rim 1234 of artesian well 1202 flows down a conically-shaped surface into a moat 1212. Moat 1212 is provided with a drain 1214 that is operatively connected to a waste unit 1208 through a conduit 1216 and a waste tube 1218. Without taking up any rinse fluid, intake tip 1300 can be brought into contact with the rinse fluid rising up from artesian well 1202 so as to be rinsed off before and/or after a fluid uptake step. Use of relatively small lengths or amounts of oil or other spacing fluid which temporarily separate two aqueous volumes can prevent cross-contamination of reagent vials, and can also permit aqueous volumes to coalesce after they have been formed, in some embodiments, without further manipulation by the system or apparatus. Thus, for example, sample fluid can be introduced, then, after the introduction of a small volume of oil to prevent contamination, the primer set fluid can be introduced to coalesce with the sample fluid discrete volume.

To prevent uptake of air bubbles and/or entrapment of air bubbles, a tip design as shown in FIG. 13 can be utilized. As shown in FIG. 13, an immiscible-fluid-discrete-volume-forming conduit 1301 can be provided with an angled tip 1300 that is slanted at an angle $\theta$. Angle $\theta$ can be from about 15° to about 75°, for example, from about 30° to about 65°, and in some embodiments, from about 50° to about 70°. With such a design, aqueous immiscible-fluid-discrete-volumes 1302 can be formed in immiscible-fluid-discrete-volume-forming conduit 1301, spaced by spacing fluid 1304, and free of entrapped air.

Another method of making aqueous immiscible-fluid-discrete-volumes spaced by spacing fluid and dispersed in a zebra pattern can involve the use of a rocker mechanism system 1400 as shown in FIG. 14. As depicted, rocker mechanism system 1400 is provided with two intake or aspiration tips 1402 and 1404, each of which is operatively connected to a pumping system (not shown) and one or more immiscible-fluid-discrete-volume-forming conduits. Intake tips 1402 and 1404 can be rigidly fixed to movable plates 1406 and 1408, respectively. Plates 1406 and 1408 can be provided with bearings, for example, linear bearings, and tracks or rails that enable linear vertical movement of plates 1406 and 1408 along guide rails 1410 and 1412, respectively. Guide rails 1410 and 1412 can be rigidly fixed, for example, bolted, to a support platform 1450. A drive unit 1430 including appropriate gearing and pulleys, and can be provided to pivot a rocker arm axle 1414 about a central axis thereof. Affixed to rocker arm pivot 1414 is a rocker arm 1401 which translates the pivoting motion of rocker arm pivot 1414 to push rods 1416 and 1418. Although push rods 1416 and 1418 are generally rigid, they can comprise twisted aluminum bars that have some degree of flexibility and elasticity. Each of push rods 1416 and 1418 is connected at an upper end thereof to rocker arm 1401, and at a lower end thereof to faceplates 1406 and 1408. In operation, as drive unit 1430 causes the left-side of rocker arm 1401 to move in a downward direction, the right side of rocker arm 1401 moves in an upward direction, and vice versa. As such, and through a translation of motion, intake tips 1402 and 1404 alternate moving up and down such that as one of intake tips 1402 and 1404 moves up, the other of intake tips 1402 and 1404 moves down.

According to various embodiments, the rocking motion of rocker mechanism system 1400 can be synchronized with the positioning of one or more sample or reagent trays 1420 under intake tips 1402 and 1404. The one or more sample or reagent trays 1420 can be movable on an X-Y movable stage. Alternatively or additionally, rocker mechanism system 1400 can be mounted on an X-Y movable stage.

Although not shown, a second sample tray can be provided on a second X-Y movable stage underneath intake tip 1402. In some embodiments, one of intake tips 1402 and 1404 can be used to pull up aqueous samples from a respective sample tray and the other of intake tips 1402 and 1404 can be used to pull up reagents, for example, primer sets, from a respective reagent tray. After each sucking action to intake either an aqueous sample immiscible-fluid-discrete-volume or a reagent immiscible-fluid-discrete-volume, a spacing fluid can be disposed under the respective intake tip so that the respective intake tip can pull up the spacing fluid such that a zebra pattern can be formed in an immiscible-fluid-discrete-volume-forming conduit. Aqueous sample immiscible-fluid-discrete-volumes taken up by one of intake tips 1402 and 1404 can be combined with reagent immiscible-fluid-discrete-volumes taken up by the other of intake tips 1402 and 1404, downstream of intake tips 1402 and 1404, for example, using any of the rotary or merge valves described herein.

FIG. 15 depicts a system 1500 for generating a set of immiscible-fluid-discrete-volumes 1502 and subsequently pushing the set of immiscible-fluid-discrete-volumes 1502 into a downstream processing conduit 1504. System 1500 can be used to carry out a method wherein an immiscible-fluid-discrete-volume-forming conduit 1506, comprising an introduction tip 1508, is manipulated in a two fluid-containing vessel 1510 to form spaced apart aqueous immiscible-fluid-discrete-volumes having spacing fluid disposed between adjacent immiscible-fluid-discrete-volumes in the set. Immiscible-fluid-discrete-volume generation can involve, for example, the methods as generally described in connection with the embodiments of FIGS. 8, 9A, 9B, and 10A-10D described herein. A set of immiscible-fluid-discrete-volumes generated in immiscible-fluid-discrete-volume-forming conduit 1506 can be pulled through a Y-junction body 1512 and into a temporary holding conduit 1514 by negative pressure created in temporary holding conduit 1514 via a syringe pump 1516, although other suitable types of pumps can be used. According to various embodiments, rather than a Y-junction configuration, a rotary valve can be used. By reversing the action of syringe pump 1516, a set of immiscible-fluid-discrete-volumes 1502 that has been pulled into temporary holding conduit 1514 can then be pushed through and out of the temporary holding conduit 1514, through Y-junction body 1512, and downstream into processing conduit 1504.

As shown in FIG. 15, each of conduits 1504, 1506, and 1514 can be connected to Y-junction body 1512 through a ferrule, such as ferrule 1518 as shown. In some embodiments, Y-junction body 1512 can comprise a valve-free junction 1520, as shown. In other embodiments, Y-junction body 1512 can be provided with a valve, for example, a multi-channel diverter valve such as valve 2700 shown in FIGS. 27 and 28 herein.

Using the system shown in FIG. 15, many different sets or batches of aqueous immiscible-fluid-discrete-volumes can be generated, temporarily held, and pushed into a downstream processing tube. For example, if the holding tube accommodates 100 aqueous immiscible-fluid-discrete-volumes spaced apart therein by spacing fluid, and 1000 immiscible-fluid-discrete-volumes are desired, 10 processes can be carried out wherein, for example, the temporary holding conduit 1514 is filled with a set of 100 immiscible-fluid-discrete-volumes, a diverter and/or valve in the Y-junction body 1512 is switched to cause a fluid communication with a downstream processing conduit, and each set of 100 immiscible-fluid-discrete-volumes are pushed through the Y-junction body 1512 into fluid processing conduit 1504, one set at a time. Automated control of valving, if provided, within the Y-junction body 1512 can facilitate the synchronization of valve actuation so that when syringe pump 1516 applies positive pressure to push fluid, the set of immiscible-fluid-discrete-volumes in temporary holding tube 1514 can only exit the Y-junction body 1512 to the downstream fluid processing conduit 1504. According to various embodiments, this type of pressure and valving control can also control or regulate aspiration. According to various embodiments, this action does not, for instance, have to occur within the body of the valve.

In order to have great control over very small fluid volumes, a conventional syringe pump can be used as syringe pump 1516, and in some embodiments, gearing can be implemented to gear down the otherwise conventional syringe pump to accommodate small movements of finite volumes of fluid. In some embodiments, a reciprocating pump can be used with appropriate gearing to provide both negative pressure and positive pressure, alternating.

According to various embodiments, an immiscible-fluid-discrete-volume can be generated in an immiscible-fluid-discrete-volume-forming conduit, and spaced apart by spacing fluid, according to any of the various methods described herein. To minimize and/or eliminate the formation of air bubbles in an immiscible-fluid-discrete-volume-forming conduit, and to minimize or eliminate merging of adjacent spaced-apart immiscible-fluid-discrete-volumes, methods of pushing a pattern of immiscible-fluid-discrete-volumes and spacing fluid through a conduit can be used after the immiscible-fluid-discrete-volumes are generated. In so doing, a pattern of immiscible-fluid-discrete-volumes can be moved through a processing conduit without the use of negative pressure. An exemplary system for pushing a pattern of immiscible-fluid-discrete-volumes through a conduit, after the pattern is formed, is depicted in FIGS. 16 and 17.

As shown in FIG. 16, a method is provided that can involve the generation of a relatively small number of immiscible-fluid-discrete-volumes in a pattern, spaced apart from one another by an average distance by a spacing fluid, which set of immiscible-fluid-discrete-volumes can then be separated from a subsequent set of immiscible-fluid-discrete-volumes to achieve a separation distance between sets that is greater than the average distance between immiscible-fluid-discrete-volumes in a single set. Once each set of immiscible-fluid-discrete-volumes is generated, the set can be pushed, rather than pulled, into a main flow path or main processing conduit, using positive pressure, thereby reducing and/or eliminating the creation of air bubbles or merging of adjacent immiscible-fluid-discrete-volumes in the processing conduit. A system 1600, as depicted in FIG. 16, can be used to carry out such a method. In some embodiments, such a system can prevent the slugs from passing through a tee or valve which causes them to change direction, negating a need for a valving structure, thereby preserving the integrity of the slugs.

As shown in FIG. 16, system 1600 can include a pump 1602 operatively connected to a selector valve 1604 that can be manipulated to perform a number of actions in an immiscible-fluid-discrete-volume-forming conduit 1601. As shown in FIG. 16, selector valve 1604 is operatively connected to ports 1606 and 1608 which can be used as an inlet port and an outlet port, respectively, depending upon a desired action selected. Immiscible-fluid-discrete-volume-forming conduit 1601 is provided with valves 1616 and 1618 adjacent ports 1606 and 1608, respectively.

FIG. 16 shows a total of 11 method steps that can be used to carry out an immiscible-fluid-discrete-volume-forming operation as described above, and depicts the various states of valves 1616 and 1618, and the direction of flow through ports 1606 and 1608, in each step. In the first step shown at the top of FIG. 16, both valves 1616 and 1618 are closed and an intake tip 1603 of immiscible-fluid-discrete-volume-forming conduit 1601 is positioned within a spacing fluid vessel 1612. Next, valve 1616 is opened while valve 1618 remains closed, and pump 1602 is actuated to draw fluid into port 1608. The drawing action is timed with an alternating disposition of intake tip 1603 back-and-forth between spacing fluid vessel 1612 and an aqueous immiscible-fluid-discrete-volume fluid vessel 1614. The alternating submersion of intake tip 1603 into the spacing fluid in vessel 1612 and the aqueous immiscible-fluid-discrete-volume fluid in vessel 1614, as described elsewhere herein, generates a pattern of aqueous immiscible-fluid-discrete-volumes in the immiscible-fluid-discrete-volume-forming conduit 1601, separated from one another by spacing fluid. As an example of such an uptake technique, reference is made to FIGS. 8, 9A, 9B, and 10A-10D described herein and the accompanying descriptions thereof. The pattern of spaced aqueous immiscible-fluid-discrete-volumes in immiscible-fluid-discrete-volume-forming conduit 1601 is referred to herein as a zebra pattern. In some embodiments, two fluids that are miscible with each other, for example, an aqueous sample and an aqueous solution of primers, can be sequentially sipped, in between sips of a spacing fluid, to form an immiscible-fluid-discrete-volume containing both sample and primers, and bounded at both ends by spacing fluid.

After a first set of aqueous immiscible-fluid-discrete-volumes is formed in conduit 1601, for example, 15 spaced-apart aqueous immiscible-fluid-discrete-volumes, tip 1603 is then held in spacing fluid vessel 1612 for a period of time sufficient to enable the uptake of a large spacing fluid spacer following the first set of 15 aqueous immiscible-fluid-discrete-volumes, although any number of immiscible-fluid-discrete volumes can be included in each set, for example, 50, 100, or 150 volumes. The large spacer can be used to separate the first set of aqueous immiscible-fluid-discrete-volumes from a subsequent set of aqueous immiscible-fluid-discrete-volumes, as shown in the third and fourth steps depicted in FIG. 16.

After two complete sets of aqueous immiscible-fluid-discrete-volumes are generated in immiscible-fluid-discrete-volume-forming conduit 1601, intake tip 1603 is held in spacing fluid 1612 and valve 1616 is closed such that the first set of aqueous immiscible-fluid-discrete-volumes, but not the second set of aqueous immiscible-fluid-discrete-volumes, is located along conduit 1601 between port 1606 and 1608, as shown in the fifth step of the process identified in FIG. 16 as the first "Loaded" step. Once the first set of aqueous immiscible-fluid-discrete-volumes is loaded as shown in the fifth step, valve 1618 is opened and pump 1602 is configured along with selector valve 1604 to push spacing fluid through port 1606 into conduit 1601, and through and past valve 1618, as shown in the sixth step identified as the "Push a Batch" step. Once the first set of immiscible-fluid-discrete-volumes passes valve 1618, valve 1618 is closed and the first set of immiscible-fluid-discrete-volumes is ready for down-stream processing as shown in the seventh step identified as the "ready" step. Next, as depicted in steps 8-11, the second set of immiscible-fluid-discrete-volumes is pulled through open valve 1616 until it is positioned between ports 1606 and 1608, while at the same time a third set of immiscible-fluid-discrete-volumes is generated by the alternating disposition of intake tip 1603 in vessels 1612 and 1614. As shown in the ninth step identified as the "Loaded" step, once the second set of immiscible-fluid-discrete-volumes is positioned between ports 1606 and 1608, valve 1616 is closed and the second set of immiscible-fluid-discrete-volumes is pushed through valve 1618 (step 10 "Push a Batch") in the same manner that the first set of immiscible-fluid-discrete-volumes was pushed in the sixth step ("Push a Batch") described above. The method described in connection with FIG. 16 can be repeated so that multiple sets of immiscible-fluid-discrete-volumes can be pushed into a down-stream processing conduit under positive pressure, with each set being spaced apart from a subsequent set by a relatively large spacing fluid spacer.

An alternative method to that shown in FIG. 16 is depicted in FIG. 17 wherein a pump 1702, selector valve 1704, ports 1706 and 1708, and valves 1716 and 1718, are shown. In the method shown in connection with FIG. 17, the intake tip of the immiscible-fluid-discrete-volume-forming conduit can be disposed initially in a rinse fluid retained in vessel 1720 prior to being disposed alternating in a spacing fluid vessel 1712 and an aqueous immiscible-fluid-discrete-volume fluid vessel 1714. As shown in FIG. 17, the negative pressure used to initially uptake the spacing fluid and aqueous immiscible-fluid-discrete-volumes is drawn through upstream port 1706 as opposed to being drawn through downstream port 1708. Another difference between the system and method shown in FIG. 17 relative to the system and method shown in FIG. 16 is that a first set of aqueous immiscible-fluid-discrete-volumes is moved all the way to a ready position, identified as the sixth step shown ("Ready"), before a second set of immiscible-fluid-discrete-volumes is generated as shown in the seventh step identified as ("Suck a Batch"). According to various embodiments, selector valve 1704 can be oriented to the waste conduit, such that extra fluid that had been drawn into syringe 1702 can be expelled from syringe 1702 so that syringe 1702 can draw additional fluid thereinto. This syringe purging can be performed at any time, for example, after step 2 and before step 7. The length of an aqueous volume generated by embodiments illustrated in FIG. 17 can, for example, in one regard, be twice as long as aqueous volumes generated according to embodiments shown in FIG. 16.

As can be understood with reference to FIGS. 15, 16, and 17, the present teachings provide, in some embodiments, a method comprising: applying a negative pressure to a conduit system comprising an intake tip; contacting the intake tip with a first fluid and a second fluid that is immiscible with the first fluid, while applying the negative pressure, to draw the first fluid and the second fluid into the conduit system and form a set of discrete volumes of the first fluid spaced apart from one another by the second fluid, the set moving in a first direction in the conduit system; and thereafter, applying a positive pressure to the conduit system to push the set of discrete volumes in the conduit system. In some embodiments, the method can comprise applying a positive pressure that causes the set to move in the first direction. In some embodiments, the method can comprise applying a positive pressure that causes the set to move in the conduit system in a second direction that is opposite the first direction. In some embodiments the method can comprise applying the negative pressure to the conduit system until the set moves past a first diverter and the method can further comprise then changing a position of the diverter before applying the positive pressure, for example, to change the pathway of the set. According to various embodiments, it is not necessary to change the position of the diverter, but it is necessary to actuate additional valves to set the direction of the fluid. In some embodiments, the method can comprise applying the negative pressure to the conduit system until the set moves past a valve and a port, and the method can further comprise then closing the valve, and furthermore, the applying of positive pressure can comprise applying a positive pressure through the port. In some embodiments, the method can comprise applying the negative pressure with a reversible pump, and reversing the action of the reversible pump to apply the positive pressure. In some embodiments, the contacting further comprises applying an electro-wetting force to move at least one of the first fluid and the second fluid to a location adjacent the intake tip. According to various embodiments, two or more additional pumps can be provided to output a set of slugs generated by the systems shown in FIGS. 15, 16, and 17, so as to move the set of slugs into a processing system, for example, a processing system as described in connection with FIGS. 1A and 1B.

According to various embodiments of the present teachings, a method is provided that comprises: alternately introducing a first fluid and a second fluid, that is immiscible with the first fluid, into a conduit, to form a set of immiscible discrete volumes of the second fluid, each immiscible discrete volume of the set being separated from one or more other immiscible discrete volumes of the set by the first fluid, the set comprising a first end and a second end; moving the set of immiscible discrete volumes in a first direction by withdrawing from the conduit, some of the first fluid from the first end of the set; and moving the set in the first direction by adding to the conduit, more first fluid at the second end of the set. In some embodiments, the method can involve processing a first fluid that comprises an oil and a second fluid that comprises an aqueous liquid, for example, an aqueous sample that is immiscible in the oil. In some embodiments, the method can further comprise moving the set past a valve in the conduit and closing the valve before moving the set in the first direction by adding to the conduit more first fluid at the second end of the set. In some embodiments, closing a valve can comprise rotating a rotary valve as described herein, for example, in connection with FIGS. 23-28.

According to some embodiments, electro-wetting or opto-electro-wetting can be used to manipulate one or more reagent or aqueous sample so that a small volume, for example, from about 10 nanoliters (nl) to about 100 nl of reagent or sample can be introduced into the uptake tip of an immiscible-fluid-discrete-volume-forming conduit. Using electro-wetting, a single reagent or a plurality of different reagents can be moved from a supply or reservoir to a tip pick-up location on an electro-wetting plate such that, for example, movement of the uptake tip of an immiscible-fluid-discrete-volume-forming conduit can be minimized or avoided all together. In an exemplary embodiment, a bulk supply of different reagents can be disposed on different areas, reagents, recesses, wells, or zones of an electro-wetting plate. In some embodiments, the different reagents can be covered with a layer of oil to prevent evaporation and contamination thereof.

From the embodiment shown in FIG. 18, an electro-wetting reagent manipulation system 1800 is shown and comprises an electro-wetting plate 1802 on which a reagent droplet 1804 has been manipulated and moved by electro-wetting action to a pick-up location 1806 on electro-wetting plate 1802. Reagent drop 1804 traversed a reagent transfer pathway 1808 moving from one independently controlled electro-wetting location or spot 1810 to another through an appropriate application of charge to the spots 1810 controlled by an electro-wetting pathway control unit 1822. While a single pathway 1808 is shown, it is to be understood that a variety of pathways are provided on electro-wetting plate 1802 such that reagents from any of reagent supply locations 1812, 1814, 1816, 1818, and 1820 can be moved to pick-up location 1806. At pick-up location 1806, reagent drop 1804 can be taken up into an immiscible-fluid-discrete-volume-forming conduit 1824 through the distal intake tip 1826 of the immiscible-fluid-discrete-volume-forming conduit 1824 which can be in close proximity to, or in contact with, pick-up location 1806. According to various embodiments, an opto-electro-wetting system can be used to transfer the reagents, rather than an electro-wetting system.

Through application of a voltage or voltage gradient at any one of reagent locations 1812, 1814, 1816, 1818, and 1820, reagents at such location can be pulled toward the right-side edge of the location to be in close proximity to a first independently controllable electro-wetting spot 1828 along respective reagent transfer pathway 1808. Further details about generating such a voltage and the manipulation of fluid droplets by electro-wetting can be found, for example, in U.S. Pat. No. 6,629,826 B2 to Yoon et al., U.S. Pat. No. 6,958,132 to Chiou et al., and U.S. Pat. No. 6,911,132 to Pamula et al., each of which is incorporated herein by reference.

In some embodiments, all reagent moving or transfer, and storage of bulk reagents, on electro-wetting plate 1802, can be done under an oil or spacing fluid overlay. According to various embodiments, a cover can be implemented at a small fixed distance spaced from the electro-wetted surface, to generate a voltage field. According to various embodiments, two electrodes can be implemented, one positioned below the aqueous volumes or reagents, the other above. According to various, the upper electrode can be a ground plane. According to various embodiments, the upper or lower electrodes can be fabricated from indium tin oxide (ITO), so that the electrode is transparent. According to various embodiments employing a cover plate, the use of oil can be eliminated, and greater accuracy can be achieved. The bulk reagent locations 1812, 1814, 1816, 1818, and 1820, can be provided with a higher cover-spacing distance, that is, a portion of the cover can be spaced further from such electro-wetting surface than in other areas of the system, so that more bulk reagent can be accommodated. In some embodiments, each reagent transfer pathway can optionally be washed or rinsed between a fluid manipulation process. In some embodiments, two or more reagent droplets or portions can be transferred from two or more of the reagent locations, and merged together, for example, at pick-up location 1806, so that a combination of reagents can simultaneously be introduced through intake tip 1826 and into immiscible-fluid-discrete-volume-forming conduit 1824.

According to various embodiments, and as illustrated in FIG. 19, the present teachings comprise a multi-conduit fluid manipulator 1900. Multi-conduit fluid manipulator 1900 can comprise a head 1902, comprising conduits 1904, 1906, 1908, and 1910, disposed thereon. Head 1902 can be rotated such that each conduit can be pointed in a first direction, for example, downward, such as toward a multi-well plate 1912. By rotating head 1902, the orientation of the conduits can be altered such that different fluids from, for example, multi-well plate 1912, can be aspirated into, or dispensed from, each of the conduits.

In some embodiments, multi-conduit fluid manipulator 1900 can comprise movement mechanisms 1914 and 1916. Movement mechanisms 1914 and 1916 can function to manipulate head 1902 in X, Y, and Z directions. Multi-conduit fluid manipulator 1900 can comprise a mirror 1918. Mirror 1918 can be used to detect the relative positions of conduits 1904, 1906, 1908, and 1910. In particular, mirror 1918 can be used to detect which conduit is in position for aspirating and/or dispensing fluids from, for example, multi-well plate 1912. According to various embodiments, mirror 1918 can also be used to detect aqueous volumes within each of the conduits as it is rotated into position.

FIG. 20 depicts a system 2000, according to various embodiments, for processing fluids. System 2000 can comprise a multi-conduit fluid manipulator 2002, as previously described in reference to FIG. 19. System 2000 can comprise conduits 2004, 2006, 2008, and 2010, with each conduit providing a fluid communication between system 2000 and multi-conduit fluid manipulator 2002.

Primers and/or samples can be aspirated by multi-conduit fluid manipulator 2002 from a multi-well plate 2014, or the like. Conduits 2004 and 2006 can provide fluid communications for primers and samples respectively, aspirated by multi-conduit fluid manipulator 2002. Conduit 2008 can provide a fluid communication between multi-conduit fluid manipulator 2002 and a service fluid pump 2012. Service fluid pump 2012 can supply oil, cleaning fluid, and or rinsing fluid to multi-conduit fluid manipulator 2002. Service fluid pump 2012 can also withdraw waste fluids from multi-conduit fluid manipulator 2002, and deposit the waste fluids in a waste reservoir (not shown).

In some embodiments, system 2000 can comprise a conduit 2010 that can provide a fluid communication for samples processed by system 2000 to be moved to multi-conduit fluid manipulator 2002. Multi-conduit fluid manipulator 2002 can dispense processed samples onto multi-well plate 2014.

Figure 21A:
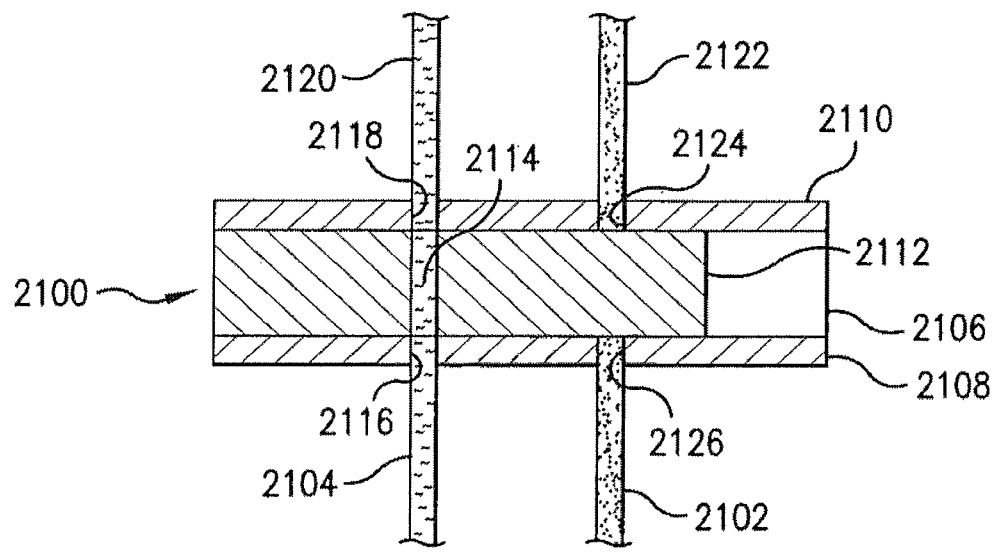

Another system for forming aqueous immiscible-fluid-discrete-volumes spaced by spacing fluid, in a conduit, is depicted in FIGS. 21A-F. As shown, the system 2100 comprises an aqueous fluid supply conduit 2104 and a spacing fluid supply conduit 2102 which deliver aqueous fluid and spacing fluid, respectively, to a housing 2106. While the aqueous fluid is described as being aqueous, it is to be understood that the system can be used to form immiscible-fluid-discrete-volumes of any first fluid separated from one another by an immiscible second fluid. Each of supply lines 2102 and 2104 can be operatively connected through a respective delivery unit (not shown) that can comprise, for example, a pump and a fluid reservoir. Housing 2106 houses a slider 2112 therein, which is configured for sliding movement in housing 2106. Slider 2112 is provided with a through-hole 2114 that, in the position shown in FIG. 21A, is aligned with aqueous fluid supply conduit 2104. Any suitable drive unit can be provided for effecting sliding movement of slider 2112 in housing 2106, for example, a programmable drive unit. Slider 2112 is snugly seated in housing 2106 and causes a sealing action, for example, to seal off spacing fluid supply conduit 2102, when positioned as shown in FIG. 21A. According to various embodiments, a sealing action can also be achieved, for example, using a rotating motion.

Housing 2106 is provided with an upper wall 2110 and a lower wall 2108. Lower wall 2108 is provided with through-holes 2126 and 2116 to accommodate and/or provide a fluid communication with spacing fluid supply conduit 2102 and aqueous fluid supply conduit 2104, respectively. Upper wall 2110 is provided with through-holes 2118 and 2124 to accommodate and provide fluid communication with a waste conduit 2120 and an aqueous immiscible-fluid-discrete-volume conduit 2122, respectively. In the position shown in FIG. 21A, aqueous fluid has been moved upwardly through aqueous fluid supply conduit 2104 to fill through-hole 2114 of slider 2112 with aqueous fluid. The through-holes through the sliders and walls of system 2100 can be considered a part of the processing conduits described herein.

Figure 21B:
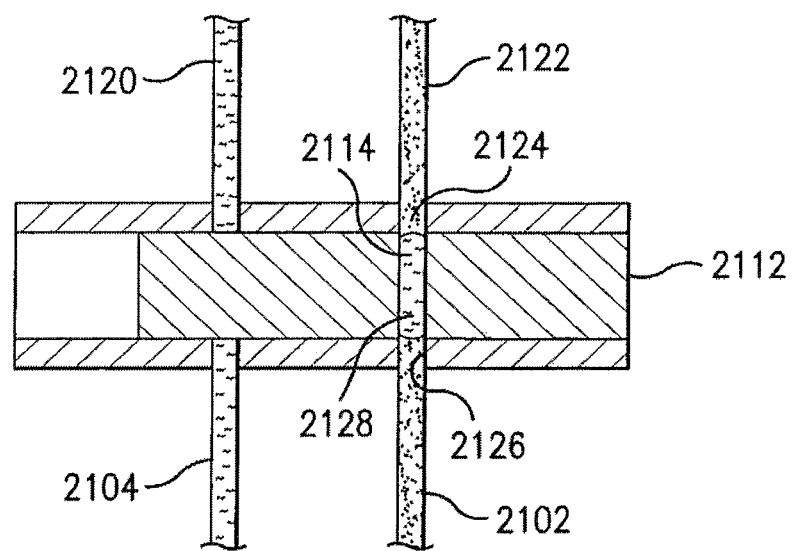
Figure 21C:
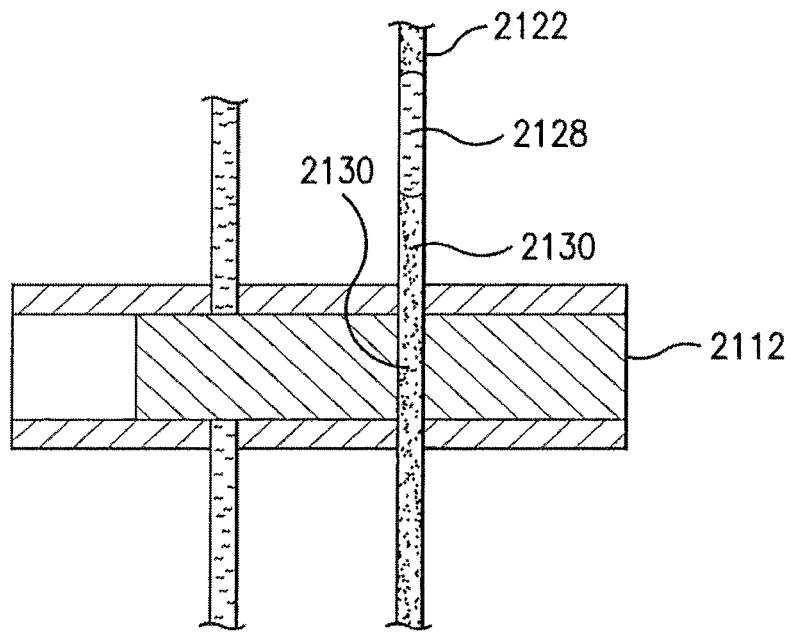
Figure 21D:
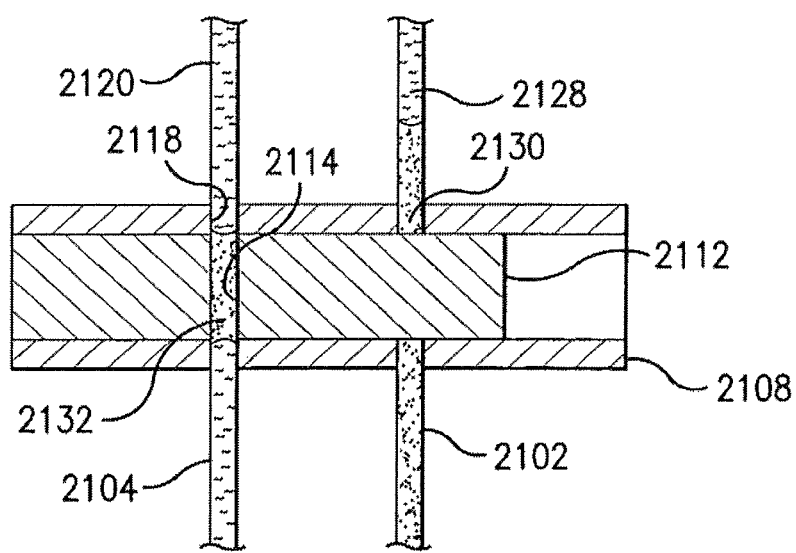
Figure 21E:
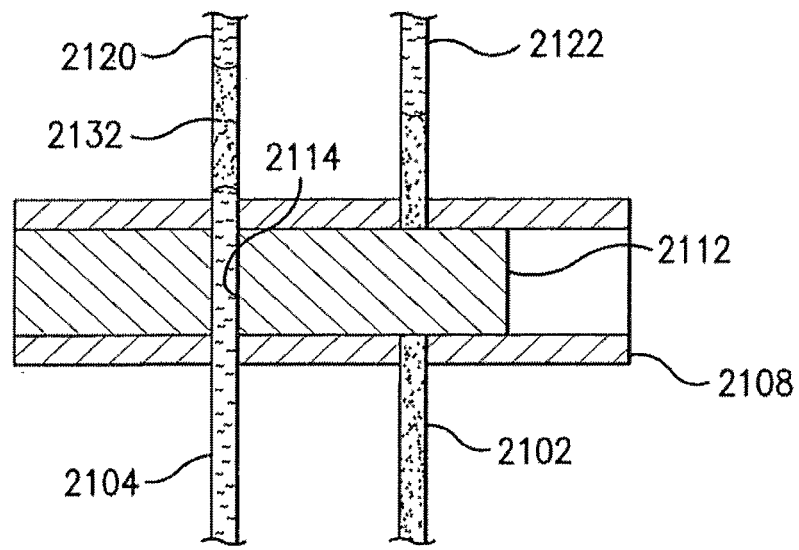

In the next step of a method using system 2100, slider 2112 is shifted to be the right-side position shown in FIG. 21B. As shown in FIG. 21B, in the right-side position slider 2112 seals off aqueous fluid supply conduit 2104 waste conduit 2120. Furthermore, when in the right-side position shown, through-hole 2114 of slider 2112 lines up with spacing fluid supply conduit 2102 and immiscible-fluid-discrete-volume conduit 2122, as well as with respective through-holes 2126 and 2124. Next, spacing fluid is moved upwardly through the spacing fluid supply conduit 2102 to force the amount of aqueous fluid identified as 2128 out of through-hole 2114 and into immiscible-fluid-discrete-volume conduit 2122, as shown in FIG. 21C. Enough spacing fluid is moved through-hole 2114 to completely displace aqueous immiscible-fluid-discrete-volume fluid 2128 from through-hole 2114 and to move at least some of spacing fluid 2130 into immiscible-fluid-discrete-volume-conduit 2122, so that through-hole 2114 is guaranteed to always be completely filled. Subsequently, slider 2112 is moved back to the left-side position shown in FIG. 21D so that through-hole 2114 of slider 2112 can then be again aligned with aqueous fluid supply conduit 2104 and waste conduit 2120. The spacing fluid carried-over from the process shown in FIG. 21C, into through-hole 2114, is identified as fluid 2132. Thereafter, as shown in FIG. 21E, aqueous immiscible-fluid-discrete-volume fluid is moved into through-hole 2114 to completely displace spacing fluid 2132 from through-hole 2114 and to push spacing fluid 2132 that had been in through-hole 2114 into waste conduit 2120. In so doing, through-hole 2114 again becomes filled with the aqueous fluid. Enough aqueous fluid is moved through-hole 2114 to completely displace spacing fluid 2130 from through-hole 2114 and to move at least some of aqueous fluid 2128 into waste conduit 2120, so that through-hole 2114 is guaranteed to always be completely filled.

Figure 21F:
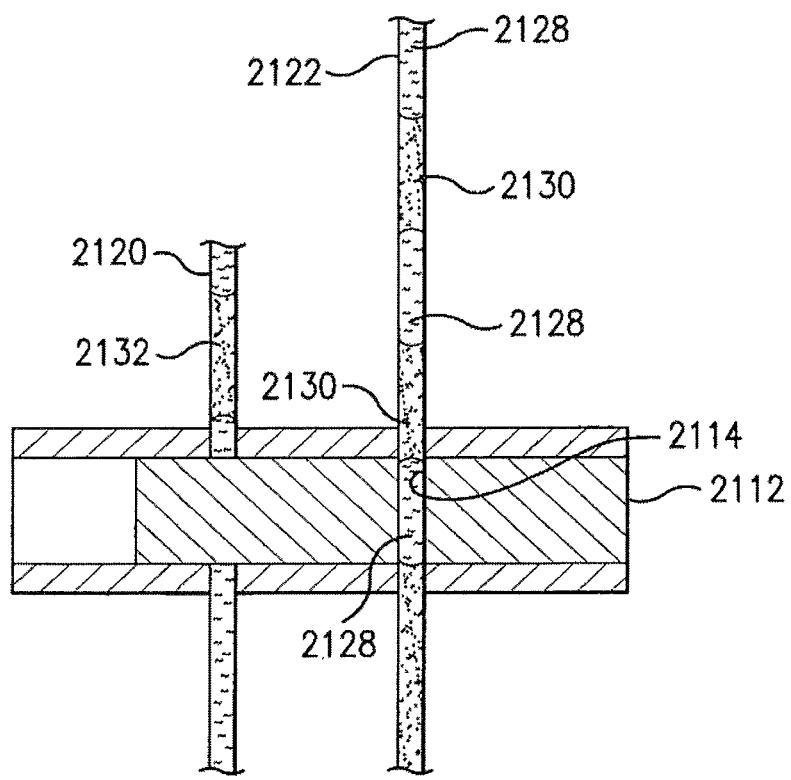

In a next step of the process, slider 2112 is shifted to the right-side position again, as shown in FIG. 21F. Another volume of aqueous fluid 2128 in through-hole 2114 can then be moved into immiscible-fluid-discrete-volume conduit 2122 such that spacing fluid 2130 in immiscible-fluid-discrete-volume conduit 2122 spaces apart aqueous immiscible-fluid-discrete-volumes 2128 from one another, as shown. By timing the sliding motion of slider 2112 with the pumping action of delivery units for the aqueous fluid supply conduit 2104 and spacing fluid supply conduit 2102, a zebra pattern of aqueous immiscible-fluid-discrete-volumes can be formed in immiscible-fluid-discrete-volume conduit 2122, as shown in FIG. 21F. In some embodiments, each aqueous immiscible-fluid-discrete-volume 2128 can comprise the same volume of fluid as the others, which can each also be equal to the volume of fluid that can be held in through-hole 2114, providing a repeatable volume, discrete-volume forming system.

A similar system to that shown in FIGS. 21A-F, is depicted in FIGS. 22A and 22B as system 2200, with at least the exception, however, that two sliders 2202 and 2204 are provided in a housing 2206. As shown in FIG. 22A, each slider 2202 and 2204 has a pair of through-holes. In the slider positions shown in FIG. 22A, the left-side through-holes in sliders 2202 and 2204 are aligned with each other, with a first aqueous fluid supply conduit 2212, and with a first immiscible-fluid-discrete-volume conduit 2224. The left-side through-holes are also aligned with respective through-holes through a bottom wall 2210 and a top wall 2208 of housing 2206. Similarly, the right-side through-holes of sliders 2202 and 2204 are aligned with each other, with a second fluid supply conduit 2216, and with a second immiscible-fluid-discrete-volume conduit 2228, as well as being aligned with respective through-holes in bottom wall 2210 and top wall 2208. System 2200 also comprises a spacing fluid supply conduit 2114 and an aqueous immiscible-fluid-discrete-volume conduit 2226, which communicate with housing 2206 through respective through-holes in walls 2210 and 2208 as shown. According to various embodiments, this permits use of a dual syringe with a single actuator.

As seen in FIG. 22A, first aqueous fluid supply conduit 2212 carries a first aqueous fluid 2218 into system 2200, second aqueous fluid supply conduit 2216 carries a second fluid 2222 to system 2200, and spacing fluid supply conduit 2214 carries a spacing fluid 2220 to system 2200.

Once the through-holes through sliders 2202 and 2204 are filled with the first and second aqueous fluids, as depicted in FIG. 22A, slider 2202 is shifted by appropriate drive means to assume a right-side position and slider 2204 is shifted with appropriate drive means to assume a left-side position, as depicted in 22B. As can be seen in FIG. 22B, by shifting the positions of the sliders relative to the positions shown in FIG. 22A, left-side through-hole 2230 of slider 2202 and right-side through-hole 2232 of slider 2204 become aligned with one another and aligned with spacing fluid supply conduit 2214 and immiscible-fluid-discrete-volume conduit 2226.

In situations where first aqueous fluid 2218 and second aqueous fluid 2222 are miscible with each other, the immiscible-fluid-discrete-volume 2234 of first aqueous fluid and the volume 2236 of second fluid can mix together to form a single, larger, aqueous immiscible-fluid-discrete-volume that can be moved into immiscible-fluid-discrete-volume conduit 2226 by spacing fluid driven through spacing fluid supply conduit 2214. In some embodiments, first aqueous fluid 2218, for example, can comprise polymerase chain reaction primers, sequencing reaction primers, fluorescent markers or labels, or the like reagents, and second aqueous fluid 2222 can comprise, for example, a sample fluid including a target nucleic acid sequence to be processed. In some embodiments, the thickness of the sliders and/or the diameters or other dimension of the through-holes, can be varied so as to provide different volumes of different fluids. These methods can provide precise metering of fluids.

As can be seen from FIGS. 21A-21F and 22A-22B, the present teachings provide a method comprising: flowing a first fluid into a through-hole of a slider housed in a slider housing and positioned at a first position; shifting the slider from the first position to a second position relative to the slider housing, to align the through-hole of the slider with an output conduit; and forcing the first fluid from inside the through-hole out of the through-hole and into the output conduit, with a second fluid that is immiscible with the first fluid. In some embodiments, the method can further comprise forcing some of the second fluid through the through-hole in the slider and into the output conduit adjacent the first fluid. In some embodiments, the method can further comprise: shifting the slider back to the first position; filling the through-hole with a second portion of the first fluid; shifting the slider from the first position back to the second position, to again align the through-hole of the slider with the output conduit; and forcing the second portion of the first fluid from inside the through-hole out of the through-hole and into the output conduit, with more of the second fluid, to form a discrete-volume of the second fluid surrounded by the first fluid.

FIGS. 21A-21F and 22A-22B also illustrate that the present teachings provide a system comprising: a housing; a slider arranged in the housing for sliding movement therein between at least a first position and a second position, the slider comprising a through hole; a first fluid supply conduit operatively connected to a first end of the through-hole when the slider is in the first position; a immiscible-fluid-discrete-volume-forming conduit operatively connected to a second, opposite end of the through-hole when the slider is in the first position; a second fluid supply conduit operatively connected to the first end of the through-hole when the slider is in the second position; an immiscible-fluid-discrete-volume-forming conduit operatively connected to the second, opposite end of the through-hole when the slider is in the second position; a supply of a first fluid operatively connected to the first fluid supply conduit; and a supply of a second fluid operatively connected to the second fluid supply conduit, wherein the second fluid and the first fluid are immiscible with respect to one another. In some embodiments, the supply of the first fluid can comprise a supply of spacing fluid, such as an oil, and the supply of second fluid can comprise a supply of an aqueous liquid, for example, an aqueous sample or aqueous reagents.

According to various embodiments, controllable valves can be used for permitting, interrupting, or otherwise controlling, fluid flow through one or more of the capillaries, tubes, orifices, through-holes, and the like conduits described herein. Exemplary controllable valves can include, but are not limited to, valves comprising a stator (or body) and rotor (or plug) structure, for example, any of the structures shown in FIGS. 23-28. According to various embodiments, controllable valves can also be used to split aqueous volumes into two equal portions.

Figure 23:
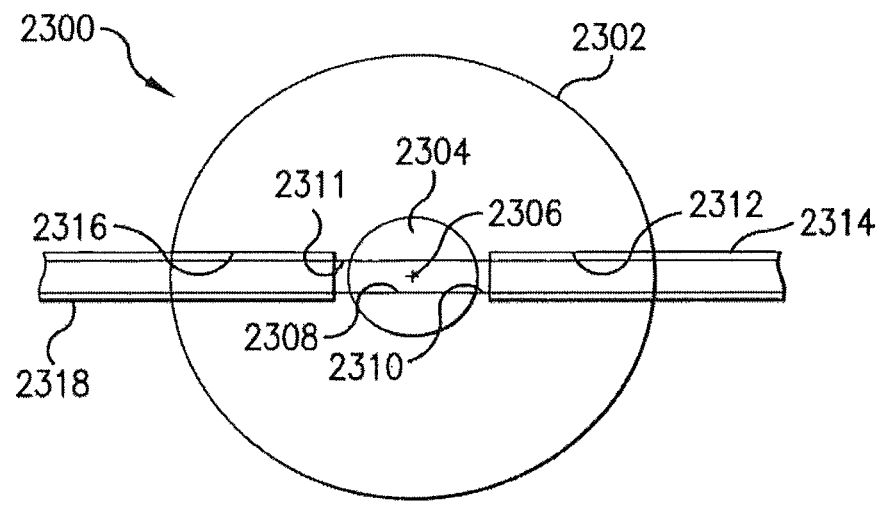
Figure 25:
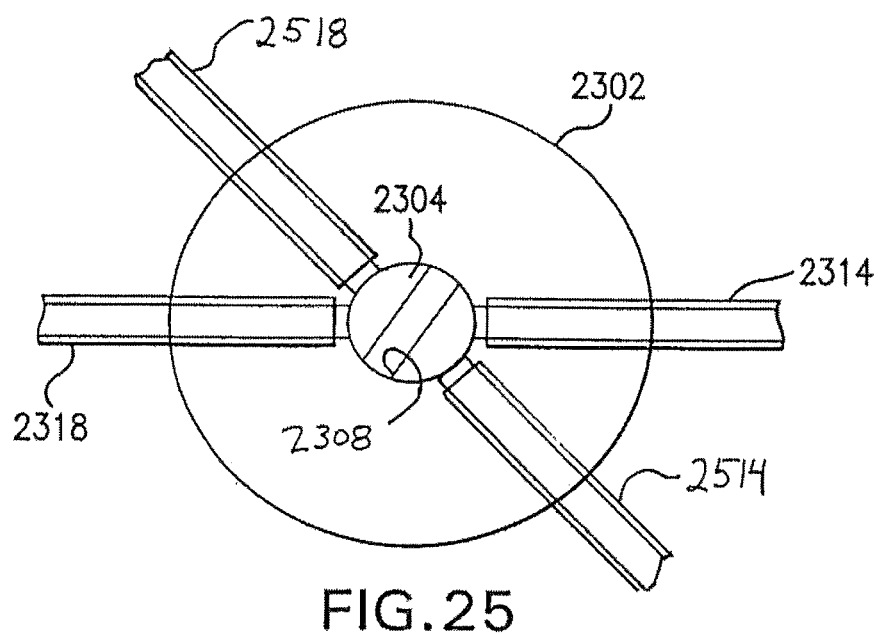

As shown in FIG. 23, valve 2300 can comprise a stator 2302, and a rotor 2304. Rotor 2304 can rotate, for example, about a central axis of rotation 2306, to orient the rotor such that valve 2300 is in an open state (as shown in FIG. 23), in a closed state (as shown in FIG. 25), or in an intermediate state. In the open state shown in FIG. 23, a central bore or through-hole 2308 through rotor 2304 is aligned with bores or through-holes 2310 and 2311 formed in stator 2302. Through-hole 2310 in stator 2302 can be aligned with a larger recess 2312 in stator 2302, in which recess 2312 and first conduit 2314, for example, a tube, can snugly fit and/or be adhered or otherwise connected. Likewise, through-hole 2311 can be aligned with and in fluid communication with a larger recess 2316 also in stator 2302. Recess 2316 can accommodate a second conduit 2318 fit, adhered, or otherwise connected to stator 2302. In some embodiments, each of through-holes 2308, 2310, and 2311, and each of recesses 2312 and 2316, has a circular cross-section although other cross-sections can be used.

As shown in FIG. 25, rotation of rotor 2304 can interrupt fluid communication between conduits 2314 and 2318 and rotation of rotor 2304 can form a fluid communication through two different conduits 2514 and 2518. A programmable drive unit can be provided to actuate rotation of rotor 2308. By filling through hole 2308 with a first fluid, for example, flowing through conduits 2314 and 2318, and then rotating rotor 2304, with a portion of the first fluid captured in through-hole 2308, to form a communication with conduits 2514 and 2518, the portion of first fluid captured in through-hole 2308 can be disposed into a flow of a second fluid through conduits 2514 and 2518, for example, wherein the second fluid is immiscible with the first fluid. Repeated operations of such action can result in the formation of a plurality of immiscible-fluid-discrete-volumes spaced apart from another by an immiscible spacing fluid, similar to the methods of formation described in connection with the slider system shown in FIGS. 21A-21F herein.

Figure 24:
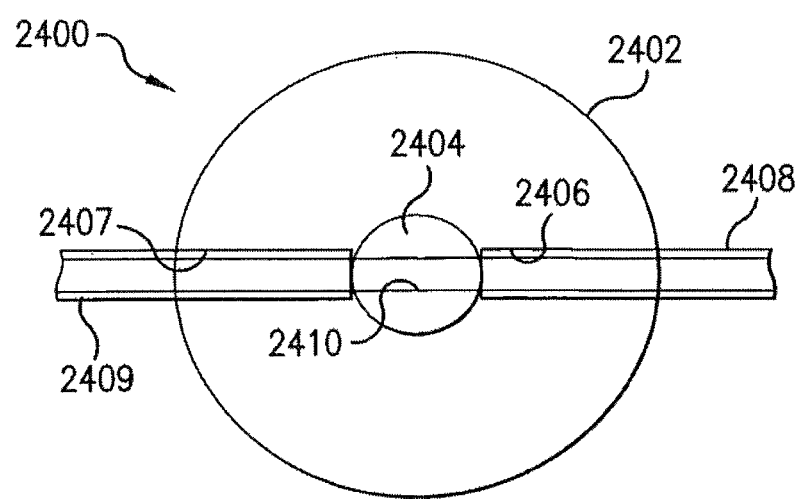

In valve 2400 shown in FIG. 24, the combination of a smaller diameter through-hole and a larger diameter recess in each side (left and right as shown) of a stator 2402 has been replaced with single through-holes 2406 and 2407 on opposing sides of a rotor 2404. In the embodiments shown in FIG. 24, conduits 2408 and 2409 are accommodated, respectively, and fit snugly within, through-holes 2406 and 2407, for example, adhered, such that the ends of conduits 2408 and 2409 closest to rotor 2404 abut rotor 2404. Valve 2400 is shown in an open position with through-hole 2410 of rotor 2404 being aligned with and sharing the same cross-sectional dimensions and shape as the interiors of conduits 2408 and 2409.

Figure 26:
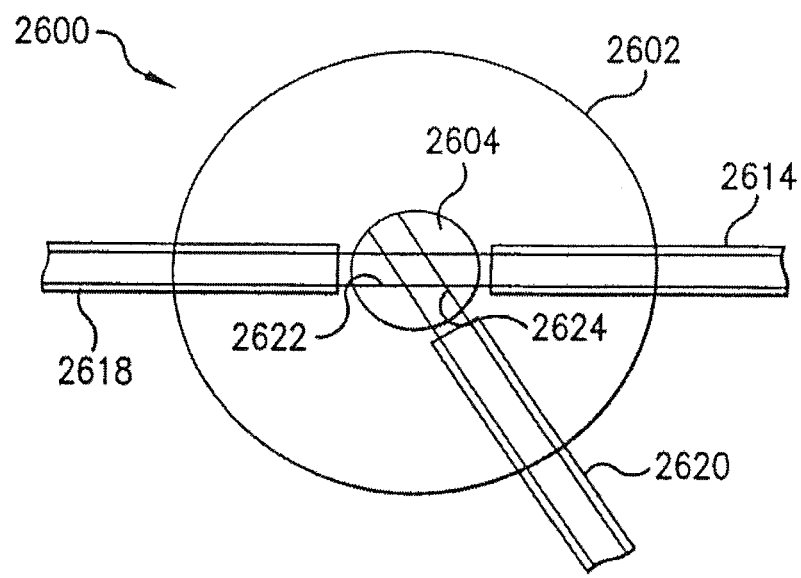

In the valve embodiment shown in FIG. 26, a valve 2600 comprises three through passages in stator 2602, which accommodate conduits 2614, 2618, and 2620. Rotor 2604 is provided with two intersecting through-holes 2622 and 2624. Depending upon the orientation of rotor 2604, for example, determined by rotation about a central axis of rotation, valve 2600 can assume a closed position, a straight-line open position, or the Y-junction position shown. When utilized in a Y-junction position such as shown in FIG. 26, one or more fluids entering the junction in the middle of rotor 2604 from conduit 2614 can merge with one or more miscible and/or immiscible fluids entering the junction from conduit 2620, such that a resulting combined flow of fluid can be made to move inside conduit 2618 in a direction away from the intersection.

In some embodiments, a first fluid to be divided into immiscible-fluid-discrete-volumes, for example, an aqueous slug fluid, can enter the junction from either of conduits 2614 or 2620, and an immiscible spacing fluid can enter the junction through the other of conduits 2614 and 2620, to generate immiscible-fluid-discrete-volumes of the first fluid spaced by the spacing fluid. In some embodiments, reagents or additional components can be merged into existing fluids or aqueous immiscible-fluid-discrete-volumes entering the intersection, for example, such that the size and/or number of reagents in an immiscible-fluid-discrete-volume can be increased at the intersection. By turning rotor 2604 about 45° counterclockwise, a fluid communication can be provided between only conduit 2614 and 2618, and fluid communication with conduit 2620 can be interrupted.

Figure 27:
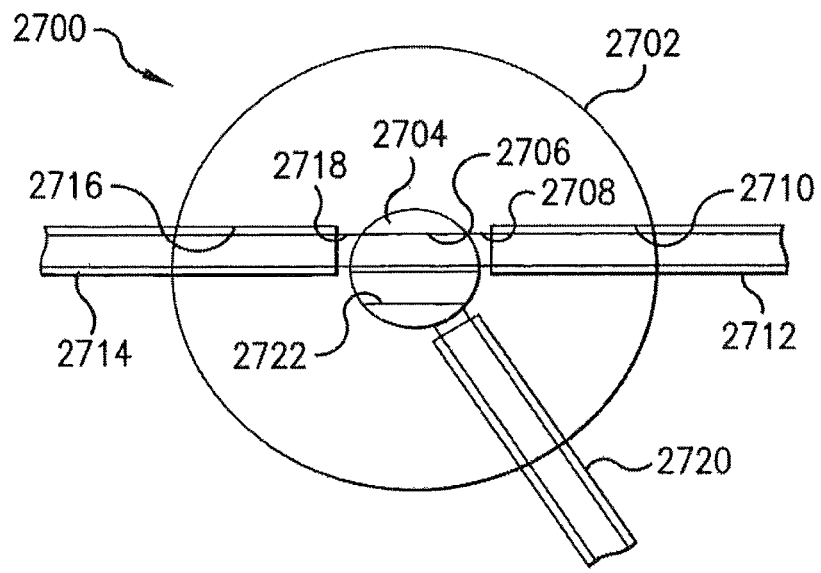
Figure 28:
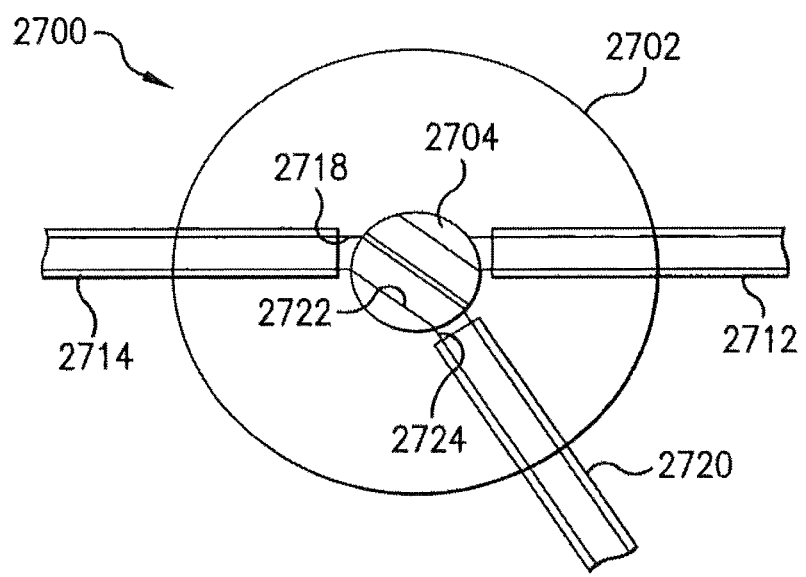

Another controllable valve that can be implemented in many of the systems and methods described herein, is the valve shown in FIGS. 27 and 28. Valve 2700 comprises a stator 2702 and a rotor 2704 that comprises two through-holes 2706 and 2722. In a first orientation of rotor 2704, as shown in FIG. 27, through-hole 2706 is aligned with through-holes 2708 and 2718 of stator 2702 and provides a fluid communication between conduit 2712 and conduit 2714. In FIG. 27, through-hole 2722 in rotor 2704 is in a closed, non-operative, position.

As shown in FIG. 28, by rotating rotor 2704, through-hole 2722 can be aligned with through-hole 2718 and through-hole 2724 in stator 2702 such that conduit 2714 is in fluid communication with conduit 2720 and fluid communication to conduit 2712 is interrupted.

As can be seen from FIGS. 23-28, a method is provided that comprises merging together at an junction of a first conduit and a second conduit a first fluid and a second fluid, the first fluid comprising a spacing fluid and the second fluid comprising an immiscible-discrete-volume-forming fluid that is immiscible with the first fluid, such that a set of immiscible-fluid-discrete-volumes of the second fluid are formed in a third conduit in fluid communication with the first conduit and the second conduit, wherein each immiscible-fluid-discrete-volume of the set is spaced apart from other immiscible-fluid-discrete-volumes by the first fluid, and at least one of the first fluid, the second fluid, and the set of immiscible-fluid-discrete-volumes flows through a rotary valve comprising a stator and a rotor. According to various embodiments, a stator/rotor combination can be used to transport spacing fluid or aqueous volumes in two different directions, without the aqueous volumes having to undergo a significant change in direction. In some embodiments, at least a portion of each of the first conduit, the second conduit, and the third conduit is disposed in the rotor, and the junction comprises an junction of the three portions in the rotor. In some embodiments, the rotor can comprise at least two independent, non-intersecting through-holes formed therein, wherein one of the at least two through-holes is in fluid communication with the first conduit, and another of the at least two through-holes is in fluid communication with the second conduit. According to various embodiments, additional holes can be bored at an offset, such that multiple fluids can be transferred at a time using a single valve.

As shown in FIG. 29, according to various embodiments a valve can be provided that has a slider 2908 in a housing 2910 that moves to either form a three-way junction between three conduits 2902, 2904, and 2906, or to interrupt fluid communication between conduits 2902 and 2904, and thus, to interrupt fluid communication between either conduit 2902 or conduit 2904, and conduit 2906.

Through the use of various combinations of the valves shown in FIGS. 23-29, any of a variety of fluid processing pathways can be effectuated in a multi-pathway system such as the multi-pathway systems described herein. According to various embodiments illustrated in FIGS. 23-29 and otherwise, any of the valves described herein can also be a linear offset valve, or other valve mechanism.

As shown in FIG. 30, according to various embodiments of the present teachings, fluid transport of liquid samples, primers, separation fluid such as oil, or other fluid components can be effected using an electro-wetting device 3000. According to various embodiments as shown in FIG. 30, electro-wetting device 3000 can comprise opposed plates 3002, which can be, for example, a pair of glass plates separated by a small gap 3014. Opposed plates 3002 made of other material can also be used. The electro-wetting device 3000 can also comprise a set of sample/primer tracks 3004 for the receipt, transport, and mixing of samples and/or primers under electro-wetting control. In general, according to various embodiments, each of opposed plates 3002 can comprise electrodes 3012 facing each other across gap 3014 between opposed plates 3002, and forming the pathways of sample/primer tracks 3004 by electro-wetting action. (According to various embodiments as illustrated, only one of the pair of opposed electrodes is shown for ease of illustration.) According to various embodiments, sample/primer tracks 3004 can comprise generally short, parallel straight tracks as illustrated. According to various embodiments, electrodes 3012 can be coated with a material such as Teflon™ to change surface energy, such that the aqueous volumes do not wet the surface without the modification of the surface energy enabled by the electro-wetting field. According to various embodiments, the gap 3014 can be filled with oil 3016.

Electro-wetting device 3000, in general, effects fluid transport by electro-wetting action. Discussion of aspects of electro-wetting phenomena can, for example, be found in the afore-mentioned U.S. Pat. No. 6,629,826 B2, to Yoon et al., U.S. Pat. No. 6,958,132 to Chiou et al., and U.S. Pat. No. 6,911,132 to Pamula et al. In general, when electrodes 3012 of electro-wetting device 3000 are energized by an electric field, the normally hydrophobic surfaces of the opposed plates 3002 become hydrophilic due to the influence of the applied electric field. Under such conditions, an aqueous drop or other liquid volume or film that is centered over a hydrophobic region, but in contact with the hydrophilic area under influence of the applied electric field, will move due to hydrophilic attraction at the contact line until that drop is centered over the hydrophilic area, thereby effecting fluid transport. It will be appreciated that while electrodes 3012 are illustrated in FIG. 30 as outlining a series of straight fluid pathways or tracks caused by electro-wetting action that generally form a grid pattern, in various embodiments the sample/primer tracks 3004 can be formed in other patterns, such as curved, non-gridded, or other patterns or pathways.

According to various embodiments, sample and/or primer liquid drops or other liquid volumes can be drawn by electro-wetting action from sample/primer tracks 3004 into a center track 3010. The center track 3010 can be in fluid communication with a master mix track 3006. Each of center track 3010 and master mix track 3006 can be defined by electrodes positioned to induce electro-wetting effects along the respective tracks. Master mix track 3006 can supply and/or transport a sample drop, primer drop, combined sample/primer drop, or other liquid volume for mixing with further reagents or materials, for example, for PCR or other reactions. According to various embodiments, generally, relatively smaller sample and primer volumes are combined with a larger master-mix volume, to create an input aqueous volume or slug. Master-mix track 3006 is thus, according to various embodiments, generally larger and devoted to the single master-mix reagent. According to various embodiments as shown in FIG. 30, the resulting solution consisting of mixed sample, primer, and/or other reagents as mixed, can then be driven by electro-wetting action to an exit track 3008. The output liquid drop or volume delivered to exit track 3008 can, for example, be communicated to an output tube or other port for further detection, electrophoresis, or other processes. When the drops are immersed in a non-aqueous spacing fluid that is immiscible with the aqueous volume or slug, the aqueous volume or slug can be in the form of an immiscible-fluid-discrete-volume.

According to various embodiments in one regard, the sample, primers, or other liquid material can be introduced to electro-wetting device 3000 using a single tip pipettor or other device which communicates those liquids to a series of ports 3018 or other inlets on electro-wetting device 3000 and/or which communicates with sample/primer tracks 3004 or other areas. According to various embodiments, the pipettor can be a multi-tip device that delivers fluid to input ports on 9 or 4.5 mm centers, in either a one-dimensional array or a two-dimensional array. If a small number of samples will be used for a reaction run, the samples can remain in the set of ports 3018 for the duration of the run. Primers can be pipetted into remaining ports 3018 and then combined with each of the samples under electro-wetting control. After completion of the desired combination reaction, ports with the primers can be rinsed out and refilled with other primers, until the run is complete. According to various embodiments, M×N zip code primers are used and a rinsing operation is omitted, wherein the M×N zip code primers can be, for example, those described in U.S. patent application Ser. No. 11/507,735 to Lee et al., filed Aug. 22, 2006, entitled "Apparatus, System, and Method Using Immiscible-Fluid-Discrete-Volumes", which is incorporated herein in its entirety by reference. According to various embodiments, when the number of samples or number of primers is small, none of the primers or samples need be pipetted out of their source well plates more than one time per run. If the number of samples or primers is larger than the number of ports 3018, then either primers or samples can be pipetted several times during a reaction run, but, for example, not as often as the number of drops that will be generated and extracted through exit track 3008. According to various embodiments, the, electro-wetting device 3000 can be configured such that there are, for example, two areas with 384 input ports to accommodate a full standard-sized tray of samples, and a full standard-sized tray of primers. Other numbers and configurations of input ports can be used.

FIG. 31 depicts the same device as shown in FIG. 30 but with fluids contained therein. Primer and sample drops 3116 can be variously introduced at the ends of short, parallel sample/primer tracks 3004 of electro-wetting device 3000, and driven under influence of an electric field applied between electrodes formed in opposed plates 3002, between which oil 3016 is disposed, into a center track 3010. The primers and samples driven together in this manner form combined drops 3112. The combined drops 3112 themselves can be driven by electro-wetting action along center track 3010 to a position adjacent to master mix track 3006 containing master mix 3114. Master mix 3114 can contain further materials or reagents, such as reagents or material for PCR, sequencing reactions, fluorescence detection assays, or other reactions or processes. The master mix 3114 can combine with the combined drops 3112 to form output drops 3118 that can be driven by electro-wetting action through exit track 3008 for removal and delivery, for example to PCR or other downstream processes.

As illustrated in FIG. 32, according to various embodiments, sample/primer tracks 3202 can be associated with, and in one regard, defined by, a set of electrodes 3210 in an electro-wetting device 3200. According to various embodiments as illustrated in FIG. 32, the set of electrodes 3210 may be formed in a pattern having a set of jagged edges between adjacent electrode areas, to facilitate the transition of a drop of primer or sample from one electrode to another. According to other various embodiments, the set of electrodes 3210 can be formed without the use of jagged or irregular edges. According to various embodiments illustrated in FIG. 32, a set of primer/sample drops 3214 can be driven by electro-wetting action to the area of center track 3208, and caused to combine into combined drop 3212 by contacting and merging into each other. According to various embodiments, primer/sample drops 3214 can be of the same size or of different sizes. Once combined into a combined drop 3212, the combined drop 3212 can be driven by electro-wetting action along center track 3208 to other areas of electro-wetting device 3200, for example to combine with master mix materials, or to be processed in other ways. According to various embodiments, electro-wetting device 3200 illustrated in FIG. 32, and other electro-wetting devices illustrated herein, can instead comprise opto-electro-wetting devices as, for example, described in the aforementioned U.S. Pat. No. 6,958,132 to Chiou et al., which is incorporated herein in its entirety by reference.

According to various embodiments, the electric field strength and other parameters of electro-wetting device 3200 are adjusted so that a number of parallel electrodes all work in the exact same fashion to produce drops of identical size. In various embodiment in this regard, each of primer/sample tracks 3202 can be configured to form a drop that is larger than the size desired, for example approximately twice the size desired. According to various embodiments, this enlarged drop can be transported around desired pathways by energizing pairs of electrodes at the same time. According to various embodiments, enlarged drops formed in this manner can be transported to one location on electro-wetting device 3200, where the enlarged drop can be split into a drop or drops of the same or consistent size, plus a remainder as appropriate. The remainder can re returned to an on-plate reservoir. Because electro-wetting can effect fluid transport at comparatively high velocity, incorporating additional tracks, steps or pathways for fluid samples to traverse generally does not have a significant effect on processing throughput.

As illustrated in FIG. 33, according to various embodiments, a processed sample drop 3306 generated by an electro-wetting device 3300 can be aspirated or otherwise introduced into the opening of an immiscible-fluid-discrete-volume-forming tube 3304, to form a sequence of processed sample plugs, slugs, or other defined volumes. According to various embodiments, oil or another immiscible fluid can be maintained in the gap between the opposed plates 3302 whenever a sample drop 3306 is not present. In such configurations, oil or other immiscible fluid can be drawn in after the sample drop by aspirating a volume of liquid greater than the volume of the sample drop 3306, so that oil or other immiscible fluid is drawn in behind the sample drop. According to various embodiments in a further regard, electro-wetting device 3300 can be operated by continuously drawing material into immiscible-fluid-discrete-volume-forming tube 3304 using a syringe pump, or other vacuum or pressure-forming device, for example, that operates at a constant speed. If a sample drop is not present at the final electrode aligned with an output port 3308 that communicates the drop to immiscible-fluid-discrete-volume-forming tube 3304, oil or other immiscible fluid can be drawn in. When a sample drop 3306 is moved to the final electrode area, the drop can be pulled into immiscible-fluid-discrete-volume-forming tube 3304. Timing the transfer of a sequence of sample drops evenly can result in a sequence of evenly spaced drops separated by oil or other spacing fluid formed in immiscible-fluid-discrete-volume-forming tube 3304. Sample drop 3306 can be moved into position for uptake into immiscible-fluid-discrete-volume-forming tube 3304 comparatively quickly using electro-wetting action, and surface tension holds sample drop 3306 together once it begins to be pulled into the aperture of immiscible-fluid-discrete-volume-forming tube 3304. According to various embodiments, the field which permits the sample drop 3306 to wet the surface can be de-activated to permit sample drop 3306 to more easily enter the immiscible-fluid-discrete-volume-forming tube 3304, after the sample drop 3306 is positioned in the appropriate location.

According to various embodiments in one regard, it may be noted that causing fluid transport of sample drops and other liquids using electro-wetting action, in general, depends on two closely spaced electrodes positioned on opposite surfaces. Therefore, the top plate of opposed plates 3302 can not have an electrode in the area taken up by an output port 3308 that communicates with immiscible-fluid-discrete-volume-forming tube 3304. According to various embodiments, the final electrode (not shown) of electro-wetting device 3300 can therefore be shaped in a torus or donut-like shape, with the aperture of immiscible-fluid-discrete-volume-forming tube 3304 in the center of the final electrode hole. Sample drop 3306 will cover the final electrode when moved into position for uptake into immiscible-fluid-discrete-volume-forming tube 3304, and the electrode can be turned off as soon as sample drop 3306 is finished moving. Sample drop 3306 can be pulled into immiscible-fluid-discrete-volume-forming tube 3304 after the oil left in the center hole is removed.

As shown in FIG. 34, according to various embodiments of the present teachings, an electro-wetting device 3400 having a paired input port 3404 can accept primer and/or sample liquid from an external syringe pump via paired input port 3404, rather, for example, than drawing from an on-board supply reservoir. According to various embodiments, this configuration can be used with M×N zip code primers as described elsewhere herein, where a small set of primers is used for all reactions. According to various embodiments, a single pump can be used for all deliveries, as in, for example, the commercially available Hydra™ robot pump available from Wanner Engineering, Inc. of Minneapolis Minn. According to various embodiments as illustrated in FIG. 34, drops of primer and sample received via paired input port 3404 can be separated or singulated for delivery to a set of primer/sample tracks 3412 using electro-wetting action, and merged in a center track of electro-wetting device 3400. The merged sample/primer drops can then be moved one at a time to an output port 3406 and/or output port 3408, where the merged drops can be aspirated along with an amount of surrounding oil into an immiscible-fluid-discrete-volume-forming tube or other device. According to various embodiments as shown, fine pitch adjustment screws 3410 can allow the relative positioning of the various supporting plates to be adjusted.

FIG. 35 is a side view of the same device depicted in FIG. 34, according to various embodiments of the present teachings. As shown, electro-wetting device 3400 can include an oil reservoir 3512 beneath a bottom frame 3510 thereof. Oil reservoir 3512 can store oil or other immiscible fluid that can be used to generate spaced-apart immiscible-fluid-discrete-volumes that can be removed via output port 3406, as well as to cover reagents as they are moved on the electro-wetting device 3400. According to embodiments as shown, primer and sample can be introduced via paired input port 3404. The sample and primer drops can be subjected to merging or other transport operations using sample/primer tracks 3412, along with collection, mixing and other electro-wetting tracks. Other transport configurations can be used.

As shown in FIG. 36, according to various embodiments of the present teachings, liquid sample 3608 can be stored in sample reservoirs 3610, for extraction and processing in an electro-wetting device 3600. According to various embodiments as illustrated in one regard, sample reservoirs 3610 can comprise comparatively narrow, deep spaces to enable introduction and storage of significant volumes of sample, primer, or other liquid. Creating sample reservoirs, for example, in the form of wide drops trapped between opposed plates of unused areas of an electro-wetting device would require a large surface area to create a reservoir with a significant volume. According to various embodiments, sample reservoirs used to store samples should be small and comparatively closely spaced, so that a relatively high density of them can be achieved in a reasonably-sized system, including for automation purposes. According to various embodiments, sample reservoirs can be covered with a layer of oil to prevent evaporation.

According to embodiments as shown in FIG. 36, sample reservoirs 3610 can be formed in a bottom plate 3604 which is covered by a top plate 3602. Top plate 3602 can have formed therein through-holes 3606, communicating with the sample reservoirs 3610. Through-holes 3606 can receive sample, primer, or other liquid by pipette, syringe, or other introduction. Sample reservoirs 3610 can communicate with primer/sample tracks 3612 to extract smaller volumes of sample 3608, primer or other liquid under electro-wetting control.

As shown in FIG. 37, according to various embodiments of the present teachings, one or more sample reservoir drop 3706 can be introduced in respective sample reservoirs 3712 formed in a bottom plate 3704 of an electro-wetting device 3700. Bottom plate 3704 can also have an oil conduit 3710 for the introduction of oil formed therein. According to various embodiments as illustrated, the sample reservoir drop 3706 can be introduced via through-holes 3708 formed in a top plate 3702 of electro-wetting device 3700, through-holes 3708 communicating with sample reservoirs 3712. Once sample reservoir drop 3706 is formed in one of sample reservoirs 3712, surface tension on sample reservoir drop 3706 prevents the perimeter of sample reservoir drop 3706 from spontaneously flowing into the narrow gap of oil conduit 3710. According to various embodiments, through-holes 3708 formed in top plate 3702 create a voltage field causing preferential wetting of the edge where the respective tracks are located, assuring access to the full volume of reagent. If the surface is coated with polytetrafluoroethylene or other anti-stick and/or hydrophobic coating material, there will be no wetting except where the tracks and field exist.

As shown in FIG. 38, according to various embodiments of the present teachings, an electro-wetting device 3800 can employ a set of sample reservoir wells 3812 to store one or more sample reservoir drops 3810 for extraction and processing under electro-wetting control. According to embodiments as shown, electro-wetting device 3800 can comprise an oil input port 3802 into which oil or other immiscible or spacing fluid can be introduced, along with an oil return port 3804 for removing of oil or other immiscible or spacing fluid. According to various embodiments as illustrated, oil that is introduced through oil input port 3802 fills the gap between opposed plates of electro-wetting device 3800. The oil filling the volume between the opposed plates can be continuously recirculated, to generate a prevailing current of oil. Since smaller sample drops extracted from sample reservoir drops 3810 can be moved comparatively rapidly from one electrode to another through the circulating oil, an extracted sample drop can be held in place against the prevailing oil current. The prevailing oil current can push large sample reservoir drops 3810 against a side of sample reservoir wells 3812 in which they reside. The pressure of the circulating oil current and the surface tension of sample reservoir drops 3810 can thereby balance, preventing the sample reservoir drop 3810 from being pulled out of sample reservoir well 3812 entirely due to frictional circulation forces.

According to various embodiments as likewise illustrated in FIG. 38, electro-wetting device 3800 illustrated therein can also comprise a waste diversion electrode 3808 and a waste port 3806. Waste diversion electrode 3808 can be used to draw residual or satellite droplets and other contaminants out of the system through waste port 3806 by electro-wetting action, before those contaminants merge with sample or primer drops. According to various embodiments, waste diversion electrode 3808 can also be used to draw off a cleaning solution added between different samples and/or primers which are used in a single reservoir, to minimize risk of cross-contamination. According to various embodiments in another regard, the circulating oil can recirculate through a reservoir or trap, where contaminants can, for instance, float to a top surface of the oil or be trapped in a filter. According to various embodiments, the final outlet point for delivery of the processed sample/primer drop can be shielded from the circulating oil current, to avoid disturbing the transfer of the finished drop to an immiscible-fluid-discrete-volume-forming tube or other output point. According to various embodiments, there can be multiple output ports which can be configured, for example, to interface with to more than one system as described herein with respect to FIGS. 1A and 1B.

As shown in FIG. 39, according to various embodiments of the present teachings, a bottom electro-wetting plate 3902, suitable for use in various electro-wetting devices described herein, can comprise electrodes 3904. According to various embodiments, electrodes 3904 can terminate in contact pads 3906 arranged along a bottom edge of electro-wetting plate 3902, to connect to wires for receiving electrical energy to generate electro-wetting fields. According to various embodiments described herein, an opto-electro-wetting device can be used in place of an electro-wetting device. According to embodiments using an opto-electrowetting device, the plate electrodes do not need to have fixed paths but can be, for example, an array of small elements covering any desired pattern, or completely covering the bottom or other surface of the device for maximum flexibility.

According to various embodiments of the present teachings, electro-wetting action can be used to effect other types of fluid flow control. For example, electro-wetting action can be used to implement an adder tee. According to embodiments, an electro-wetting adder tee can comprise at least one inlet port, one or more adder ports, and one or more outlet ports, for fluids, such as immiscible-fluid-discrete-volumes separated by a spacing fluid, to be received and mixed. According to various embodiments, a main inlet and the one ore more outlet ports can be connected by a track of electrodes. One or more adder ports can be connected to this track with a further set of electrodes that meet at a tee junction. According to various embodiments, the one or more adder ports can be used to introduce reagents to immiscible-fluid-discrete-volumes received in the adder tee. Sample drops or other liquid drops that are received in the main inlet port are quickly moved to the junction point of the adder track, where in the sample drop can be combined with a drop or drops received from one or more of the adder ports. Each of the one or more adder ports can each have more than one set of electrodes that are of different sizes, so that they are optimized for different mix ratios. According to various embodiments, the perimeter of the glass plates forming the adder tee can be sealed.

According to various embodiments, an electro-wetting adder tee formed in this manner can advantageously function without a limit on the mix ratios at which it can operate. Further, an electro-wetting adder tee can programmably operate at diverse mix ratios without a need for mechanical changes, since various electrode combinations can be activated under software control. Further, an electro-wetting adder tee according to various embodiments can include a waste port or track for rinsing or washing, and can operate to reposition sample immiscible-fluid-discrete-volumes or other discrete volumes passing through the tee, to even out the spacing between them. According to various embodiments, such a tee can also be used as a splitter to split aqueous volumes.

According to various embodiments; for example, electrodes along the adder track can be used as storage buffers to even out the flow rate of the sample immiscible-fluid-discrete-volumes or other discrete volumes. The oil or other immiscible or spacing fluid that enters the tee flows around the sample or other aqueous drops, since the fluids are not constrained by tubing. The total volume of liquid flowing into the outlet port moves at a constant rate. If liquid drops are transferred to the outlet port at even time intervals, the spacing of the sample immiscible-fluid-discrete-volumes or other separated liquid volumes will be uniform, even if the spacing or separation of the sample and other liquids received at the inlet port or ports and adder ports was not equal.

According to various embodiments of the present teachings in another regard, an electro-wetting adder tee can be energized with direct current or with alternating current, or with a combination of both. According to various embodiments, if electrodes of an electro-wetting adder tee are energized using alternating current, the electrodes can be used to sense the presence of a drop, as well as to move the drop, since the presence of an aqueous sample drop or other discrete liquid volume will change the capacitance of the electrode circuit. According to various embodiments, the electrodes of an electro-wetting adder tee can be energized by patterned light sources in an opto-electro-wetting system, rather than individual electrode switches with their associated wiring. According to various embodiments, the use of patterned light sources can permit arbitrary track patterns to be generated, permitting greater flexibility in reagent volume and methods of use.

As seen from the descriptions of FIGS. 30-39, the present teachings can provide, in some embodiments, a system comprising: an immiscible-fluid-discrete-volume-forming conduit comprising an intake end; an electro-wetting device comprising one or more electro-wetting pathways for transporting one or more immiscible-fluid-discrete-volumes, and an output site along at least one of the one or more tracks; and a positioning unit for positioning the intake tip adjacent or at the output site. In some embodiments, the system can further comprise a negative pressure source operatively connected to the immiscible-fluid-discrete-volume-forming conduit.

As seen from the descriptions of FIGS. 30-39, the present teachings can provide, in some embodiments, a method comprising: transporting a first droplet of a first fluid along an electro-wetting pathway of an electro-wetting device; merging the first droplet with a second of a second fluid that is miscible with the first fluid, to form an immiscible-fluid-discrete-volume; and drawing the immiscible-fluid-discrete-volume into an immiscible-fluid-discrete-volume-forming conduit. In some embodiments, the method can further comprise, prior to the drawing step, first drawing a third fluid into the immiscible-fluid-discrete-volume-forming conduit, wherein the third fluid is immiscible with the immiscible-fluid-discrete-volume. In some embodiments, the method can even further comprise drawing more of the third fluid into the immiscible-fluid-discrete-volume-forming conduit after drawing the immiscible-fluid-discrete-volume into the immiscible-fluid-discrete-volume-forming conduit.

Figure 40:
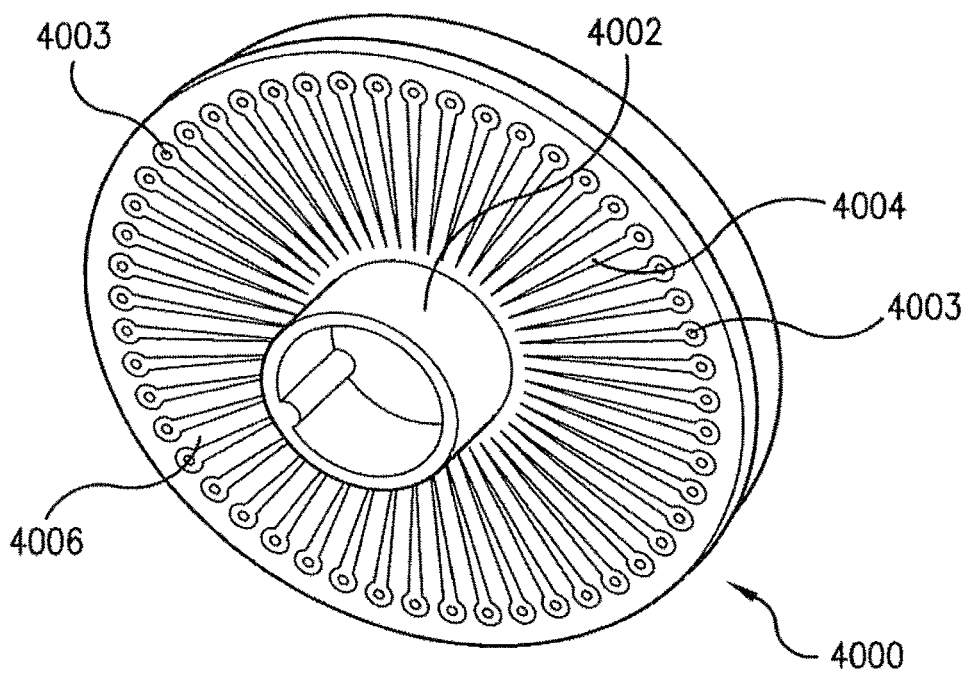

As shown in FIG. 40, according to various embodiments of the present teachings, a sequence of aqueous samples and immiscible spacer fluid volumes can be generated using an immiscible-fluid-discrete-volume-forming generator 4000. According to various embodiments, immiscible-fluid-discrete-volume-forming generator 4000 can comprise a carousel mechanism. According to various embodiments as shown in FIG. 40, immiscible-fluid-discrete-volume-forming generator 4000, which is shown in bottom view, can comprise a drive hub 4002, which can be connected to a rotary motor or other drive mechanism. Immiscible-fluid-discrete-volume-forming generator 4000 can also comprise pump cavities 4004 on one surface thereof to conduct aqueous, primer, or other samples or liquids to an immiscible-fluid-discrete-volume-forming conduit or other output. According to various embodiments as shown, each cavity of pump cavities 4004 can comprise a set of long, generally tapered conduits that can be provided with a narrower width and smaller cross-section adjacent a radially inward portion of the cavity, relative to the width and cross-section of the cavity in a region more radially outward. Immiscible-fluid-discrete-volume-forming generator 4000 can further comprise a film 4006, for example, an elastic or adhesive film, affixed to a surface of immiscible-fluid-discrete-volume-forming generator 4000, and covering and sealing the pump cavities 4004. According to various embodiments, pump cavities 4004 can be actuated by a plunger or other actuator mechanism to drive the delivery of sample or other fluids, as described herein.

Figure 41:
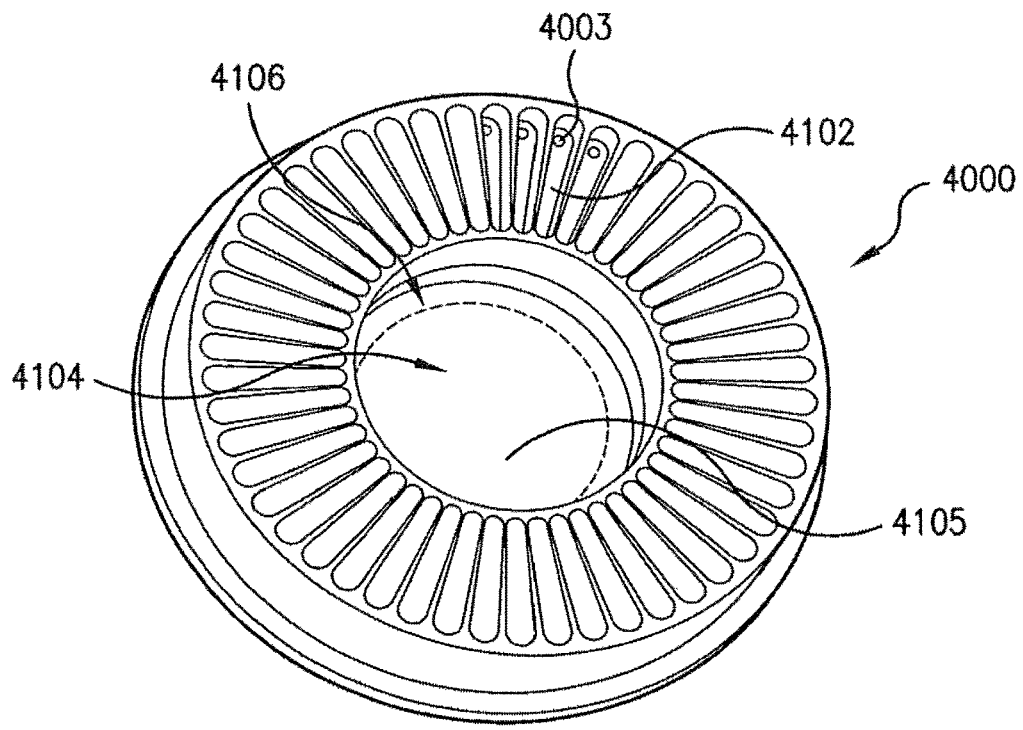

As shown in FIG. 41, according to various embodiments of the present teachings, immiscible-fluid-discrete-volume-forming generator 4000 can comprise reservoir wells 4102 formed in a slotted, radial fashion in a top portion of immiscible-fluid-discrete-volume-forming generator 4000. According to various embodiments as shown in FIG. 41, immiscible-fluid-discrete-volume-forming generator 4000, which is shown in top view, can comprise an oil reservoir 4104, in which separation oil, or other immiscible spacer fluid, can be introduced and stored. At a bottom surface 4105 of the cavity in which oil reservoir 4104 is defined, immiscible-fluid-discrete-volume-forming generator 4000 can comprise nozzles 4106. Nozzles 4106 can comprise through-holes, or other conduits or channels, extending to a bottom surface of immiscible-fluid-discrete-volume-forming generator 4000, to communicate with sample, primer, or other liquid or liquids stored in reservoir wells 4102. While reservoir wells 4102 are illustrated as formed in a generally extended slot configuration, other shapes or configurations for reservoir wells 4102 can be used.

As shown in FIG. 42, according to various embodiments of the present teachings, a immiscible-fluid-discrete-volume-forming generator 4000 can, again, comprise pump cavities 4004 formed on a bottom surface thereof, and covered by a film 4006 sealing the pump cavities 4004. According to various embodiments as shown, the pump cavities 4004 can communicate with reservoir wells 4102 via fluid conduits 4003, the reservoir wells 4102 being configured to be able to store comparatively larger volumes of sample, primer, or other liquids for immiscible-fluid-discrete-volume generation. According to various embodiments as shown in FIG. 42, liquid in individual pump cavities 4104 can be driven and extracted from those cavities in desired volumes by actuation of one or more actuators 4206. Actuators 4206 can comprise a plunger mechanism 4208, such as a hydraulic plunger or linear motor-driven plunger mechanism, or other actuator mechanism. It will be noted that while FIG. 42 illustrates two actuators labeled 4206, that those elements represent one actuator with the second, outermost actuator being an illustrative phantom. When one or more of actuators 4206 contact film 4204 underneath one of the pump cavities 4004, the film 4006 can be compressed and a pressure on the liquid contained therein be exerted. Pressure or displacement caused by action of the one or more actuators 4206 thus drives a volume of sample, primer, or other liquid out of pump cavities 4004 for delivery via nozzles 4106 or other outlet ports to a immiscible-fluid-discrete-volume-forming conduit.

As shown in FIG. 43, according to various embodiments, a immiscible-fluid-discrete-volume-forming generator assembly 4300 can comprise a turret motor 4302 capable of rotating immiscible-fluid-discrete-volume-forming base assembly 4314, and other components. According to various embodiments as shown in FIG. 43, the immiscible-fluid-discrete-volume-forming generator assembly 4300 can be equipped with fluid lines for communicating samples, primer, and other working materials into and out of immiscible-fluid-discrete-volume-forming generator assembly 4300. According to various embodiments as illustrated in FIG. 43, the fluid input and output lines can comprise a immiscible-fluid-discrete-volume-forming conduit 4304 and an oil resupply conduit 4306. The oil resupply conduit 4306 can communicate with oil reservoir 4308 containing a volume of oil 4310, such as mineral oil, or other oil or immiscible spacing or separation fluid. Immiscible-fluid-discrete-volume-forming generator assembly 4300 can further comprise an oil level sensor 4312, for example, an optical or float switch sensor, configured to detect a level of oil 4310 in oil reservoir 4308. Oil level sensor 4312 can thereby signal a pump or other supply mechanism to supply oil 4310 via oil resupply conduit 4306, upon detection of an oil level falling below a predetermined threshold. According to various embodiments in this regard, the sample, primer, or other liquid samples released for uptake into immiscible-fluid-discrete-volume-forming conduit 4304 can be generated and combined under a bath of oil 4310, preventing evaporation, contamination, and permitting the generation of oil spacer volumes by aspiration of a desired amount of oil after intake of the aqueous drop.

As shown in FIG. 44, according to various embodiments of the present teachings, immiscible-fluid-discrete-volume-forming generator 4000 can comprise one or more actuators 4402 that contact film 4504 that seals pump cavities 4506, thereby driving out a liquid drop 4508, such as a sample, primer, combined sample/primer, or other drop, via nozzle 4106. According to various embodiments, the drop 4508 can be released in an area adjacent to a lower aperture 4416 of immiscible-fluid-discrete-volume-forming conduit 4410. According to various embodiments, aperture 4416 can be aligned over nozzle 4106 by rotation of drive hub 4002 by a motor or other mechanism. According to various embodiments as shown, the aperture 4416, nozzle 4106 and drop 4508 can be immersed in oil 4107.

As shown in FIG. 45, according to various embodiments of the present teachings, immiscible-fluid-discrete-volume-forming generator 4000 can generate a liquid drop 4508, such as a sample, primer, combined sample/primer, or other liquid drop, by actuation of actuator 4502 against film 4504 that seals pump cavities 4506 containing sample, primer, or other liquid. According to embodiments as shown in FIG. 45, drop 4508 can be released or expelled via nozzle 4106 for uptake into immiscible-fluid-discrete-volume-forming conduit 4410 through a surrounding bath of oil 4107. According to various embodiments, nozzle 4106 can extend through bottom surface 4105 of reservoir 4104. According to various embodiments of the present teachings in one regard, oil 4107 can be heavier than the drop 4508, which can, for example, be aqueous, and drop 4508 can be released from nozzle 4106 with some degree of vertical momentum due to the mechanical pressure delivered by actuator 4402.

Drop 4508 can float due to buoyancy through intervening oil 4107 located between nozzle 4106 and lower aperture 4416 of immiscible-fluid-discrete-volume-forming conduit 4410. Drop 4508 can contact the aperture 4416 of the immiscible-fluid-discrete-volume-forming conduit 4510 and lodge in the inner diameter thereof. According to various embodiments, drop 4508 can be further drawn into immiscible-fluid-discrete-volume-forming conduit 4510 by a syringe pump (not shown) which pulls a vacuum on the content of immiscible-fluid-discrete-volume-forming conduit 4510. This pumping action can draw drop 4508 into the interior bore of immiscible-fluid-discrete-volume-forming conduit 4510. According to various embodiments, the pumping action can continue to draw in a volume of oil 4107 behind drop 4508, the volume of oil 4107 being determined by the total volume pulled by the syringe or other vacuum or pumping mechanism. According to various embodiments, more than one drop 4508 can be formed and allowed to float to contact aperture 4416 of immiscible-fluid-discrete-volume-forming conduit 4510 before the syringe pump or other pumping mechanism is actuated. The multiple drops can then merge, and can be drawn into immiscible-fluid-discrete-volume-forming conduit 4510 as a single liquid volume. According to various embodiments, aperture 4416 of immiscible-fluid-discrete-volume-forming conduit 4510 is not withdrawn from the surrounding oil 4107 until the end of a processing run. According to various embodiments, a separate, lightweight oil can be dispensed over the top of the contents of the various reservoirs or cavities holding sample, oil or other liquid in immiscible-fluid-discrete-volume-forming generator 4000, to eliminate contamination and evaporation of the liquid contents. In some embodiments the top surface can be sealed and a pressure pump can be used.

As shown in FIG. 46, according to various embodiments, a immiscible-fluid-discrete-volume-forming conduit 4602 having an aperture 4608 can receive liquid drops from multiple conduits, supply lines, or other conduits emerging from a plate or substrate. According to various embodiments, the multiple supply conduits can, as illustrated, comprise a sample conduit 4604 and a primer conduit 4606. Other numbers of conduits, and other types of liquids supplied by those conduits, can be used. According to various embodiments, the gap between the aperture 4608 and the sample conduit 4604 and primer conduit 4606 can be immersed in oil or other immiscible spacer fluid. For clarity, the oil or other immiscible fluid is not shown in FIG. 46.

As shown in FIGS. 47A-47E, according to various embodiments of the present teachings, a sample conduit 4706 and a primer conduit 4708 can be positioned beneath a immiscible-fluid-discrete-volume-forming conduit 4702, having an aperture 4704 at a distal tip thereof. According to various embodiments, the gap between aperture 4704 and sample conduit 4706 and primer conduit 4708 can be immersed in oil or other immiscible fluid (the oil or other immiscible fluid is not shown in FIGS. 47A-47E for clarity). According to various embodiments shown in FIG. 47A, the sample conduit 4706 can release a sample drop 4710 into the gap between aperture 4704 and sample conduit 4706. As shown in FIG. 47B, sample drop 4710 can float by buoyancy in the surrounding oil to a position in contact with the mouth of aperture 4704. As shown in FIG. 47C, while sample drop 4710 is lodged in or positioned against aperture 4704, primer conduit 4708 can release a primer drop 4712 into the surrounding oil.

According to various embodiments, the primer drop 4712 can likewise float through the surrounding oil to contact and merge with sample drop 4710 lodged in aperture 4704. As shown in FIG. 47D, sample drop 4710 and primer drop 4712 merge into a combined drop 4714 of larger size, also lodged in the area of aperture 4704. As shown in FIG. 47E, after generation of combined drop 4714, a syringe pump (not shown) or other pumping or vacuum mechanism can be activated to draw combined drop 4714 into the inner bore of immiscible-fluid-discrete-volume-forming conduit 4702. According to various embodiments, the combined drop 4714 can be fully drawn into immiscible-fluid-discrete-volume-forming conduit 4702, for instance, as an elongated liquid volume, after which time the syringe pump or other pumping mechanism can continue to operate to drawn in an additional volume of oil behind the combined drop 4714 to create an alternating sequence of aqueous and spacer immiscible-fluid-discrete-volumes, or other liquid volumes. The process illustrated in FIG. 47A-47E of alternately releasing sample drop 4710 and primer drop 4712 can be repeated to generate a sequence of combined drops 4714 separated by an oil or other immiscible spacing fluid, the entire sequence being of a desired length. According to various embodiments, sample drop 4710 and primer drop 4712 need not be strictly alternated in liquid volumes of equal length of number. According to various embodiments, additional different liquids can be released from sample conduit 4706 and primer conduit 4708 or other conduits or supply lines as an immiscible-fluid-discrete-volume sequence is generated. According to various embodiments, a master-mix solution as described herein can, for example, be added from a single conduit.

According to various embodiments, drops of sample and primer can be introduced for mixing into an immiscible-fluid-discrete-volume sequence using additional mechanisms. For example, according to embodiments as illustrated in FIG. 48, a immiscible-fluid-discrete-volume-forming generator can contain only primer reservoirs storing primer liquid for delivery through a primer conduit 4814, releasing a primer drop 4810 to float through a surrounding oil 4820 to lodge in an aperture 4804 of a immiscible-fluid-discrete-volume-forming conduit 4802. According to various embodiments as shown in FIG. 48, the immiscible-fluid-discrete-volume-forming device itself may not contain a reservoir to store the sample liquid to be introduced. Instead, according to various embodiments as shown, sample liquid 4808 can be introduced by a separate pipette 4806 positioned beneath aperture 4804 in the surrounding oil 4820, to expel a sample drop 4812 from a tip of the pipette 4806. Pipette 4806 can be, for example, positioned and actuated under robotic control. Sample drop 4812 once released from pipette 4806 can float through the surrounding oil 4820, and contact and merge with primer drop 4810 to form a combined drop (not shown) for intake into immiscible-fluid-discrete-volume-forming conduit 4802. According to various embodiments, pipette 4806 can be used to introduce liquids, other than sample material, for combination in immiscible-fluid-discrete-volume-forming conduit 4802. In the embodiment shown, immiscible-fluid-discrete-volume-forming conduit 4802 is disposed in a reservoir comprising a bottom wall 4816 having a top surface, wherein a hole is formed in bottom wall 4816 to accommodate primer conduit 4814.

Another embodiment for preparing aqueous immiscible-fluid-discrete-volumes spaced apart by spacing fluid in an immiscible-fluid-discrete-volume-forming conduit is depicted in FIGS. 49 and 50. As shown in FIG. 49, a cartridge 4900 is provided that houses a spool 4902 of film 4904 that has been pre-spotted with various reagents that have been dried down. The pre-spotted reagents on film 4904 can be in the form of individual spots 4906, for example, arranged in rows and/or in an array. Film 4904 can comprise an polyolefin film or other plastic film material and can be, for example, generally hydrophobic, except in the vicinity of each spot 4906 where the film can be relatively hydrophilic. In some embodiments, the dried down reagents constituting each spot 4906 can themselves be hydrophilic such that a drop of aqueous sample contacted spot 4906 can tend to cling to spot 4906 due to the hydrophilic nature of spot 4906.

As shown in FIG. 49, a pipettor 4912 can be manually, automatically, or robotically implemented to dispose a drop of water, aqueous sample, or an aqueous reagent, to each spot 4906 as film 4904 is pulled off of spool 4902. In some embodiments, after a row of spots 4906 is re-wetted by respective drops of fluid from pipettor 4912, a next row of spots 4906 is pulled off of spool 4902 and exposed for re-wetting. Due to the hydrophilic nature of each spot 4906 and the generally hydrophobic nature of the remaining surface of film 4904, each re-wetted spot can remain isolated from adjacent re-wetted spots.

After the aqueous fluid, sample, and/or reagent, from pipettor 4912 reconstitutes the dried down reagents of a row of spots, the row of spots is submerged in an oil or spacing fluid that is immiscible with the aqueous-based reconstituted spots.

As can be seen in both FIGS. 49 and 50, a roller 4910 can be provided in cartridge 4900 to guide film 4904 off of spool 4902, into oil or spacing fluid bath 4908, and up and out of cartridge 4900. The oil or spacing fluid in bath 4908 can be immiscible with the reconstituted spots 4906 and can cover, isolate, protect, and prevent evaporation of reconstituted spots 4906 while they are submerged. While submerged in bath 4908, reconstituted spots 4906 can be drawn into an immiscible-fluid-discrete-volume-forming conduit 4914 while the tip of such conduit is immersed in bath 4908. By continually drawing fluid into immiscible-fluid-discrete-volume-forming conduit 4914 and contacting the intake tip of conduit 4914 with each successive reconstituted spot of a row, a zebra pattern of aqueous immiscible-fluid-discrete-volumes spaced by spacer fluid can be formed in immiscible-fluid-discrete-volume-forming conduit 4914. In some embodiments, after an entire row of submerged reconstituted spots is drawn into immiscible-fluid-discrete-volume-forming conduit 4914, film 4904 can be advanced to line-up the next row of reconstituted spots 4906 with the intake tip of immiscible-fluid-discrete-volume-forming conduit 4914.

In an exemplary embodiment, each dried down spot 4906 on film 4904 constitutes a different reagent or set of reagents relative to the other dried-down spots on the film. As such, a large number of assays can be performed on an aqueous sample solution administered by pipettor 4912 drop-by-drop to the various drops, as such an aqueous sample reconstitutes and mixes with the various dried-down spots 4906. In some embodiments, each dried down spot can comprise, for example, a pair of oligonucleotide primers, such as a forward primer and a reverse primer, that can effect replication of a target stretch of nucleic acid bases that encompass a target nucleic acid sequence. In some embodiments, each dried-down spot 4906 can instead, or additionally, comprise a label or marker, for example, a reporter dye, so that, for example, a detectable polymerase chain reaction can be carried out in each aqueous immiscible-fluid-discrete-volume which is drawn into immiscible-fluid-discrete-volume-forming conduit 4914. It is to be understood that any of a variety of reagents can be included in each dried-down spot 4906 and each dried-down spot can be the same as or different than one or more other dried-down spots.

As can be appreciated from FIGS. 40-50 and the descriptions thereof provided herein, the present teaching can provide a device comprising: a substrate and an elastically deformable bottom cover. The substrate can comprise a bottom wall having a central axis of rotation and a lower surface, an annular wall extending upward from the bottom wall and defining a central reservoir radially inward with respect to the annular wall, a plurality of through-holes each extending through the bottom wall in the central reservoir, a plurality of radial reservoirs formed in the substrate and disposed radially outward with respect to the annular wall, each radial reservoir comprising at least one sidewall and a bottom, and a plurality of through-holes, at least one extending through the bottom of each radial reservoir. In some embodiments, the elastically deformable bottom cover is attached to the lower surface of the bottom wall and spaced-apart from portions of the lower surface of the bottom wall such that a respective radial fluid channel is provided between each through-hole in the central reservoir and a respective through-hole of the plurality of through-holes in the radial reservoirs. In some embodiments, the central reservoir contains a first fluid, and at least a first radial reservoir of the plurality of radial reservoirs contains a second fluid that is immiscible in the first fluid. In some embodiments, the elastically deformable bottom cover is configured to create positive pressure in the radial fluid channel between the first radial reservoir and the respective through-hole in the central reservoir when the elastically deformable bottom cover is pushed upwardly adjacent the radial fluid channel such that second fluid in the radial fluid channel is forced through the through-hole in the central reservoir and into the central reservoir. According to various embodiments, a system is provided that comprises such a device and: a rotatable support comprising a holder for holding the device; a drive unit for rotating the rotatable support, while holding the device, about the central axis of rotation; and a plunger configured to press against the bottom cover. In some embodiments, the system can further comprise a negative pressure source and a conduit, the conduit being operatively connected to the negative pressure source and comprising an intake tip positioned in the central reservoir.

As can also be appreciated with reference to FIGS. 40-50, the present teachings provide a method that can comprise: forming a first droplet of a second fluid in a first fluid, wherein the first fluid and the second fluid are immiscible with respect to one another and have different densities; moving at least one of the first droplet and an intake tip of a conduit relative to one another such that the first droplet is disposed adjacent the intake tip; and drawing the first droplet and an amount of the first fluid through the intake tip and into the conduit. In some embodiments, the method can further comprise: forming in the first fluid a second droplet of a third fluid that is miscible with the second fluid; and merging the second droplet with the first droplet, before the drawing step, wherein the drawing comprises drawing the merged first droplet and second droplet through the intake tip and into the conduit. In some embodiments, the first fluid is disposed in a container having a bottom, and the second droplet is formed by ejecting second fluid from a through-hole in the bottom, wherein the second fluid is less dense than the first fluid, and the first droplet rises in the first fluid. In some embodiments, the second fluid has a greater density than the first fluid, the droplet of the second fluid is formed on a film, and the method further comprises submersing the film in the first fluid.

The present teachings also provide a method comprising: providing a device wherein the device comprises a substrate and the substrate comprises: a bottom wall having a central axis of rotation and a lower surface; an annular wall extending upward from the bottom wall and defining a central reservoir radially inward with respect to the annular wall; a first through-hole extending through the bottom wall in the central reservoir; a radial reservoir formed in the substrate and disposed radially outward with respect to the annular wall, the radial reservoir comprising at least one sidewall and a bottom; and a second through-hole extending through the bottom of the radial reservoir. The device can further comprise an elastically deformable bottom cover attached to the lower surface of the bottom wall and spaced-apart from a portion of the lower surface of the bottom wall such that a respective radial fluid channel is provided between the first through-hole and the second through hole, wherein the central reservoir contains a first fluid, the radial fluid channel comprises a second fluid, the second fluid is less dense than the first fluid, the first fluid and the second fluid are immiscible with respect to one another. Using such a device, the method can comprise forcing the elastically deformable bottom cover upwardly toward the lower surface of the bottom wall to create positive pressure in the respective radial fluid channel that forces a droplet of the second fluid to exit the first through-hole and enter the central reservoir.

In some embodiments, the method can further comprise drawing the droplet of the second fluid and surrounding first fluid into an intake tip of a conduit.

According to various embodiments, FIG. 51 illustrates an assay plate 5100, that can be used to combine one or more samples with one or more volumes of reagents. Assay plate 5100 can comprise reservoirs for retaining a sample, for example, sample reservoirs 5106 and 5108. Assay plate 5100 can comprise one or more reservoirs for retaining reagents. For example, assay plate 5100 can comprise reagent reservoirs 5104, and 5102. Assay plate 5100 can comprise an output conduit 5118. Assay plate 5100 can comprise one reagent conduit for each reagent reservoir. Each reagent conduit can provide a fluid communication between each reagent reservoir and output conduit 5118. For example, assay plate 5100 can comprise reagent conduits 5116 and 5124, which can each provide a fluid communication between reagent reservoirs 5102 and 5104, and output conduit 5118, respectively. Assay plate 5100 can comprise a sample conduit for each sample reservoir. Each sample conduit can provide a fluid communication between a sample reservoir and output conduit 5118. For example, assay plate 5100 can comprise a sample conduit 5114 which can provide a fluid communication between sample reservoir 5108 and output conduit 5118.

Discrete amounts of sample can be pumped from each sample reservoir, through a particular sample conduit, and into output conduit 5118. Similarly, reagents can be pumped from an reagent reservoir, through a particular reagent conduit, and into output conduit 5118. For example, reagents can be pumped from reagent reservoir 5104, through reagent conduit 5124, and into output conduit 5118. Similarly, a sample or portion thereof can be pumped from sample reservoir 5108, into sample conduit 5114, and then into output conduit 5118. Discrete volumes of sample, reagents, and/or the slugs can be separated by the use of a spacing fluid disposed in output conduit 5118. The spacing fluid can be immiscible with the reagents and/or samples.

According to some embodiments, discrete amounts of reagents and sample can be pumped into output conduit 5118, and then be made to flow, for example the discrete amounts of sample and/or reagents can be made to flow in the direction of arrow 5112. Discrete amounts of reagents and sample can be combined in output conduit 5118. For example, reagents can be pumped from reagent reservoir 5102, through reagent conduit 5116, and into output conduit 5118 while, simultaneously, a discrete amount of sample is moved from sample reservoir 5108, through sample conduit 5114, and into output conduit 5118. As the discrete amount of sample and reagents emerge from their respective conduits, they can be joined into a single slug 5110. A slug can comprise a discrete amount of a sample and reagents. Alternatively, for example, a discrete amount of reagents can be moved from reagent reservoir 5104, through reagent conduit 5124, into output conduit 5118, and moved along output conduit 5118 in the direction of arrow 5112. As the discrete amounts of reagents move along output conduit 5118, the reagents will align with each downstream sample conduit. When the discrete amount of reagent and a selected sample conduit are aligned, a discrete amount of sample can be pumped from the respective sample reservoir, through the sample conduit, and joined with the discrete amount of reagents. In this way, different reagents can be combined into slugs with different samples. Alternatively, a discrete amount of sample can be moved into conduit 5118 and later joined with a discrete amount of reagent to form a slug.

Assay plate 5100 can comprise a substrate 5120 that is capable of acting as a magnetohydrodynamic (MHD) pump. The magnetohydrodynamic forces generated by substrate 5120 can be used to move discrete portions of a particular reagent, or a particular sample, into output conduit 5118. In this way, the output of each reservoir into output conduit 5118 can be independently controlled. Further disclosures of MHD pumps and materials can be found at, for example, U.S. Pat. No. 6,146,103 for micromachined magnetohydrodynamic actuators and sensors to Abraham P. Lee and Asuncion V. Lemoff, patented Nov. 14, 2000, which is incorporated herein, by reference, in their entireties.

According to various embodiments, FIG. 52 illustrates a system 5200 for forming slugs. System 5200 can comprise reagent reservoirs 5202, 5204, and 5206. System 5200 can comprise sample reservoirs 5208, 5210, and 5112. System 5200 can comprise carrier fluid conduits 5214 and 5216. Carrier fluid conduit 5214 can be in fluid communication with reagent supply reservoirs 5202, 5204, and 5206. Similarly, carrier fluid conduit 5216 can be in fluid communication with sample supply conduits and sample supply reservoirs 5208, 5210, and 5212. The sample system 5200 can comprise an output conduit 5218. Output conduit 5218 can be in fluid communication with each of the reagent reservoirs and sample reservoirs, the sample reservoirs and the reagent reservoirs can comprise MHD pumps. While six reservoirs are illustrated, it is to be understood that any number of reservoirs can be integrated for use. It is also to be understood that any combination of reagent and sample reservoirs can be integrated for use.

Discrete amounts of reagents present in the reagent reservoirs and discrete amounts of sample present in the sample reservoirs can be input into output conduit 5218. Discrete amounts of reagents and/or sample can be moved down output conduit 5218, in the direction of arrow 5220. The timing of the addition of the reagents and/or sample into the output conduit can be controlled such that the reagents and samples can be combined into a slug, for example, slug 5222. Carrier fluid can be moved to output conduit 5218 via any of the reagent reservoirs or sample reservoirs.

According to some embodiments and array of sample withdrawing conduits can be used to withdraw a number of different fluids, from a number of different sample wells, into the fluid processing system. As an array of conduits moves from one fluid to the next, contamination or carryover of the fluids can become a problem. Related art methods of cleaning an array of conduits include running a stream or water or water/ethanol mixture across the array. This type of system often results in inconsistencies in the cleaning process. For example, a first row of conduits can be cleaned relatively well, but a last row of conduits can retain contamination. Some related art methods of cleaning attempt to reverse the flow of cleaning fluid part way through the cleaning procedure, but this can often result in contamination of conduits in the center of an array. In some related art cleaning methods the cleaning mixture is moved axially with respect to each conduit, but this often requires a higher pressure, resulting in splashing of the conduit with contaminated cleaning fluid. FIG. 53 depicts such a cleaning device.

According to various embodiments, and as illustrated in FIG. 54, a cleaning or rinsing vessel is disclosed which overcomes the problems of the related art. A conduit 5402 can be inserted into a rinsing or cleaning vessel 5400. Cleaning vessel 5400 can comprise a gasket 5406, comprising a flexible material. For example, gasket 5406 can comprise rubber, plastic, or any other suitable flexible material. Cleaning vessel 5400 can comprise an inlet 5408. Inlet 5408 can be annular. Cleaning vessel 5400 can comprise a cleaning reservoir 5412 having an open bottom.

Conduit 5402 can be inserted into cleaning vessel 5400, with the tip of conduit 5402 being disposed in cleaning reservoir 5412. Gasket 5406 is shown in an open configuration, allowing conduit 5402 to be inserted into cleaning vessel 5400, without making any contact with any part of cleaning vessel 5400 itself.

According to some embodiments, FIG. 55 depicts cleaning vessel 5400, wherein gasket 5406 is in a closed configuration. In the closed configuration, gasket 5406 can create a seal around conduit 5402. The closed configuration of gasket 5406 can result from a cleaning fluid 5410 being forced under pressure into inlet 5408, and then up to and against gasket 5406. Cleaning fluid 5410 can comprise a water and ethanol mixture. The pressure of the cleaning fluid against gasket 5406 can force the gasket into the closed position. When the gasket is closed, cleaning fluid 5410 can be forced to flow around and down conduit 5402, into cleaning reservoir 5412, and then out of the open bottom of cleaning reservoir 5412. The movement of cleaning fluid 5410 around and down conduit 5402 can function to clean the conduit.

According to some embodiments, pressurized air can be applied to inlet 5408. The pressurized air can be used to maintain pressure on gasket 5406, thereby keeping gasket 5406 in the closed position. The air can function to dry and/or remove any cleaning fluid from conduit 5402. Stopping the application of pressurized air can result in gasket 5406 returning to the open position. When gasket 5406 is in the open position, conduit 5402 can be readily removed from cleaning vessel 5400, without having any contact therewith. When gasket 5406 is in the closed position, cleaning fluid is prevented from splashing into other parts of the conduit.

Other embodiments of the present teachings will be apparent to those skilled in the art from consideration of the present specification and practice of the present teachings disclosed herein. It is intended that the specification and examples be considered as exemplary only and not be limiting. All cited references, patents, and patent applications are incorporated in their entireties herein by reference.

What is claimed is:
1. A method comprising:
   suctioning discrete volumes of aqueous fluid and a spacing liquid into a first conduit such that the discrete volumes of aqueous fluid are carried and separated by the spacing liquid, the spacing liquid being disposed between the discrete volumes of aqueous fluid in the first conduit, and the spacing liquid being immiscible with the discrete volumes of aqueous fluid;
   transferring a first set and a second set of the discrete volumes of aqueous fluid separated by the spacing liquid from the first conduit to a second conduit;
   transferring the first set of discrete volumes of aqueous fluid separated by the spacing liquid from the second conduit to a third conduit;
   processing the first set of discrete volumes of aqueous fluid in the third conduit;
   holding in the second conduit the second set of the discrete volumes of aqueous fluid transferred to the second conduit while the first set of discrete volumes of aqueous fluid is transferred to and processed in the third conduit;
   after holding in the second conduit, transferring the second set of discrete volumes of aqueous fluid from the second conduit to the third conduit; and processing the second set of discrete volumes of aqueous fluid in the third conduit.

2. The method according to claim 1, wherein the processing comprises thermally cycling the first set and the second set of discrete volumes of aqueous fluid in a thermal cycling nucleic acid sequence amplification process.

3. The method according to claim 2, wherein the processing further comprises detecting a fluorescence of the first set and the second set of discrete volumes of aqueous fluid in a fluorescence detection process.

4. The method according to claim 1, wherein the processing comprises detecting a fluorescence of the first set and the second set of discrete volumes of aqueous fluid in a fluorescence detection process.

5. The method according to claim 1, wherein the discrete volumes of aqueous fluid and the spacing liquid are suctioned from a vessel into the first conduit.

6. The method according to claim 1, wherein suctioning the discrete volumes of aqueous fluid and the spacing liquid into the first conduit comprises filling an inner cross-sectional area of the first conduit with the spacing liquid disposed between discrete volumes of aqueous fluid.

\* \* \* \* \*